US012753158B2

(12) United States Patent
De Benedictis

(10) Patent No.: US 12,753,158 B2
(45) **Date of Patent: *Oct. 6, 2026**

(54) HYPERBRANCHED POLYGLYCEROL POLYGLYCIDYL ETHER AND ITS USE AS CROSSLINKER FOR POLYSACCHARIDES

(71) Applicant: BIOPOLIMERI S.R.L., San Vito Dei Normanni (IT)

(72) Inventor: Vincenzo Maria De Benedictis, San Vito Dei Normanni (IT)

(73) Assignee: BIOPOLIMERI S.R.L., San Vito Dei Normanni (IT)

( * ) Notice: Subject to any disclaimer, the term of this patent is extended or adjusted under 35 U.S.C. 154(b) by 1011 days.

This patent is subject to a terminal disclaimer.

(21) Appl. No.: 17/763,196

(22) PCT Filed: Sep. 30, 2020

(86) PCT No.: PCT/EP2020/077342

§ 371 (c)(1),
(2) Date: Mar. 23, 2022

(87) PCT Pub. No.: WO2021/064006

PCT Pub. Date: Apr. 8, 2021

(65) Prior Publication Data

US 2022/0380329 A1 Dec. 1, 2022

(30) Foreign Application Priority Data

Oct. 1, 2019 (EP) .................................... 19200803

(51) Int. Cl.

*A61K 8/73* (2006.01)
*A61K 31/738* (2006.01)
*A61Q 19/08* (2006.01)
*C07D 303/27* (2006.01)
*C08B 15/00* (2006.01)
*C08B 33/04* (2006.01)
*C08B 37/08* (2006.01)

(52) U.S. Cl.

CPC ............ *C07D 303/27* (2013.01); *A61K 8/731* (2013.01); *A61K 8/732* (2013.01); *A61K 8/735* (2013.01); *A61K 31/738* (2013.01); *A61Q 19/08* (2013.01); *C08B 15/005* (2013.01); *C08B 33/04* (2013.01); *C08B 37/0072* (2013.01)

(58) Field of Classification Search

CPC ................................ C08G 65/00; C08G 65/08
See application file for complete search history.

(56) References Cited

U.S. PATENT DOCUMENTS 9,408,797 B2 * 8/2016 Njikang ................. A61Q 19/08
2004/0127698 A1 7/2004 Tsai et al.
2009/0214604 A1 8/2009 Alvarez Lorenzo et al.
2016/0346433 A1 12/2016 Bon Betemps et al.
2017/0020799 A1 1/2017 Brillouet et al.

FOREIGN PATENT DOCUMENTS

EP 1550469 A1 7/2005
JP 2009167389 A * 7/2009
KR 102201482 B1 1/2021
WO WO 2013/079889 A1 6/2013
WO WO 2021/064006 A1 4/2021

OTHER PUBLICATIONS

Chen, S et al., Chemical Engineering Journal, "Synthesis and application of epoxy-ended hyperbranched polymers", 2018, vol. 343 , pp. 283-302 (Year: 2018).*
Horibe et al., Google English Translation of JP2009167389, 2009, 20 page translation (Year: 2009).*
International Search Report and Written Opinion mailed Feb. 18, 2021 for International Application No. PCT/EP2020/077342, 14 pages.
He et al: "Ultrasonicaton-assisted rapid determination of epoxide values in polymer mixtures containing epoxy resin," Analytical Methods 2014; vol. 6(12), pp. 4257-4261.
Yui et al: "Inflammation responsive degradation of crosslinked hyaluronic acid gels," Journal of Controlled Release 1992; vol. 22, pp. 105-116.
International Search Report and Written Opinion mailed Sep. 27, 2022 for International Application No. PCT/EP2022/068056; 17 pages.
Academic Press Dictionary of Science and Technology 1992, p. 531.
De Smedt et al., "Viscoelastic and transient network properties of hyaluronic acid as a function of the concentration", Biorheology 1993; vol. 30, pp. 31-41, 11 pages.
Levy et al., "Determination of thermodynamic dissociation constants of local anaesthetic amines: influence of ionic strength" J. Pharm. Pharmacol. 1972; vol. 24, pp. 841-847,7 pages.
Tetzlaff, "The pharmacology of local anesthetics", Regional Anesthesia, Anesthesiology Clinics of North America; Jun. 2000; vol. 18(2), pp. 217-233, 17 pages.
Valette et al., "Elaboration of epoxy foam by radical induced cationic frontal polymerization (RICFP): A proof of concept", Journal of Photochemistry and Photobiology A Chemistry, May 2023, vol. 442(32), 8 pages.

* cited by examiner

*Primary Examiner* — Bahar Craigo
(74) *Attorney, Agent, or Firm* — SQUIRE PATTON BOGGS (US) LLP

(57) ABSTRACT

The present invention relates to a hyperbranched polyglycerol polyglycidyl ether having a molecular weight from 750 to 15.000 Da; and an epoxy equivalent weight from 183 to 7.000 g/eq. It also relates to a crosslinked polysaccharide obtainable by crosslinking the polysaccharide with the hyperbranched polyglycerol polyglycidyl ether. The present invention also relates to processes for their preparation and their uses in therapy, cosmetic, agriculture and food field.

13 Claims, No Drawings

HYPERBRANCHED POLYGLYCEROL POLYGLYCIDYL ETHER AND ITS USE AS CROSSLINKER FOR POLYSACCHARIDES

CROSS-REFERENCE

The present application is a national-phase filing under 35 U.S.C. § 371 of International Application No. PCT/EP2020/077342 (filed Sep. 30, 2020), which claims the benefit of European Patent Application 19200803.5 (filed Oct. 1, 2019), both of which applications are incorporated herein by reference in their entirety.

This application claims the benefit of European Patent Application 19200803.5 filed on Oct. 1, 2019.

The present invention relates to a hyperbranched polyglycerol polyglycidyl ether. In particular, to hyperbranched polyglycerol polyglycidyl ether having a molecular weight from 750 to 15.000 Da; and an epoxy equivalent weight from 183 to 7.000 g/eq. It also relates to a crosslinked polysaccharide obtainable by crosslinking the polysaccharide with the hyperbranched polyglycerol polyglycidyl ether, a process for their preparation and their uses in food, pharmaceutical, cosmetic and agriculture industries.

BACKGROUND ART

Carbohydrates also known polysaccharides are the most abundant, easily accessible, cheap biomolecules and renewable resource on the earth, with an annual formation rate surpassing the world production rate of synthetic polymers by some orders of magnitude. They are sustainable materials synthesized by the sun's energy and fully biodegradable. Polysaccharides are present in all living organisms and are designed by nature to carry out various specific functions.

Besides their potential uses as key chemical raw materials and energy production, polysaccharides have been recognized to play a key role in a wide variety of complex biological processes. They are involved to a large extent in mediating recognition processes through their interactions with proteins and other biological entities; and cellular recognition processes including cell growth regulation, differentiation, adhesion, cancer cell metastasis, cellular trafficking, inflammation by bacteria and viruses, and immune response.

One of the most known polysaccharides is cellulose. Cellulose is a component of at least a third of advanced plants and therefore, it is unquestionably the most abundant naturally occurring reproducible organic compound. In its simplest form, cellulose is composed of β-1,4-linked glucan chains that can be arranged in different ways giving rise to different forms of cellulose. Its chemical structure corresponds to the following formula:

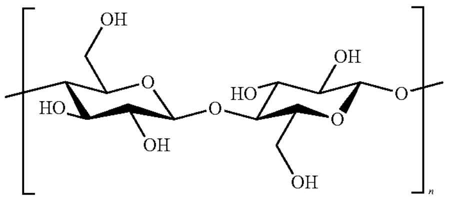

In nature, cellulose is produced in a hierarchical manner with the glucan chains associating with each other to form crystalline and non-crystalline regions that are assembled into higher-order structures such as the microfibril. Cellulose is generally obtained as the cellulose I crystalline form in which the glucan chains are aligned parallel to each other. Two forms of the native crystalline polymer, cellulose, Iα, and Iβ, have been shown to be present in differing amounts obtained from different sources.

Particularly, sodium carboxymethylcellulose (NaCMC) is defined as the sodium salt of a carboxymethyl ether of cellulose obtained directly from natural strains of fibrous plant material. The NaCMC molecule is a polymer with a base of β-D-glucose units, whose free hydroxyl groups are partially substituted by carboxymethyl groups. Its chemical structure corresponds to the following formula wherein R is H or $CH_2CO_2Na$:

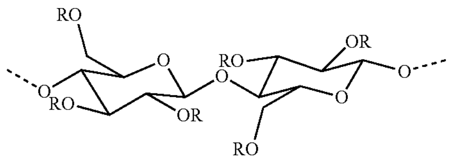

The cellulose derivative NaCMC was first used as a substitute for starch and natural gums. Large volumes of this cellulose derivative are used in paper, textile processing, detergents, drilling fluids, and protective coatings. The purified grade, known as cellulose gum, is used extensively in the food, pharmaceutical, and cosmetic industries.

Another commonly used polysaccharide is starch, which is abundant and naturally occurring. It is found in the leaves of all green plants and in the seeds, fruits, stems, roots, and tubers of most plants. Most starches are composed of two kinds of polysaccharides, a linear α-(1→4) linked glucan, called amylose, and an α-(1→4) linked glucan with 4.2 to 5.9% α-(1→6) branch linkages, called amylopectin. The chemical structure of the amylose and amylopectin units correspond to the following formulae respectively:

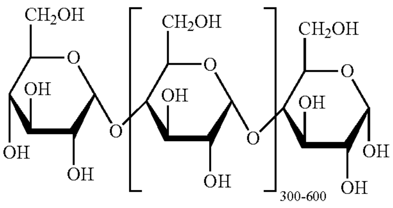

amylose

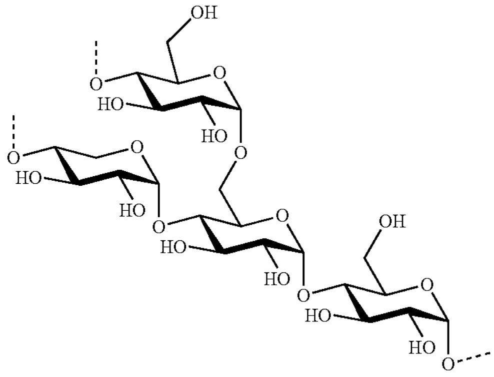

amylopectin

Starch results as an end-product of photosynthesis and serves as the chemical storage form of the energy of the sun on the Earth. It is estimated that 60-70% of the caloric intake by humans comes from starch. All starches are stored in plants as water-insoluble particles or granules in the chloroplasts in leaves and in amyloplasts in other plant tissues. The granules are relatively dense particles of compact molecules, with semi-crystalline properties.

The major category of enzymes that hydrolyse the α-(1→4) linkages of starch is the α-amylases. These enzymes are ubiquitous and are produced by bacteria, fungi, plants, and animals. In mammals, there are two specific sources, the salivary glands that secrete the enzyme into the mouth and the pancreas that secretes the enzyme into the small intestine. The α-amylases are endo-acting enzymes that attack the interior parts of the polymeric starch chains, producing a rapid drop in viscosity. Because of these properties, they are sometimes called liquefying enzymes. When α-amylases encounter a starch chain and hydrolyse an α-(1→4) linkage, they also produce low molecular weight maltodextrins by a process called multiple attack on one of the two chains that were initially cleaved. Starch is a common ingredient used widely in many food and non-food applications. However, the application of native starches is often limited because of shortcomings in their physiochemical properties such as low shear resistance and thermal stability, thermal decomposition and high retrogradation tendency.

Starch is used as additive for food processing, food starches are typically used in foods as thickeners, extenders, emulsion stabilizers and are exceptional binders in processed meats. In the pharmaceutical industry, starch is also used as an excipient, as tablet disintegrant, as binder and plasma volume expander. Starch can be chemically modified to allow the starch to function properly under conditions frequently encountered during processing or storage, such as high heat, high shear, low pH, freeze/thaw and cooling. Resistant starch is a kind of starch that escapes digestion in the small intestine of healthy individuals. It is used as an insoluble dietary fiber in processed foods and as a dietary supplement for its health benefits. Resistant starch helps to improve insulin sensitivity, increases satiety and improves markers of colonic function.

Furthermore, another branched polysaccharide is glycogen which is a multibranched polysaccharide of glucose that serves as a form of energy storage in animals, fungi, and bacteria. The polysaccharide structure represents the main storage form of glucose in the body, glycogen is the analogue of starch, with a structure like amylopectin, but more extensively branched and compact.

Finally, hyaluronic acid (HA), also called hyaluronan or sodium hyaluronate is an anionic non-sulphated glycosaminoglycan (GAG). HA is a linear high molecular weight polysaccharide that consists of repeating monomers of D-glucuronic acid and N-acetyl-D-glucosamine, linked via alternating β-(1→4) and β-(1→3) glyosidic bonds. Its chemical structure corresponds to the following formula:

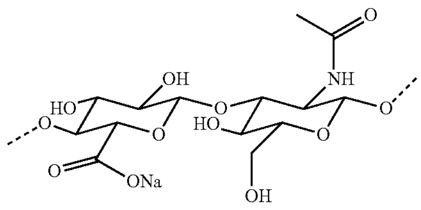

HA is widely distributed throughout the human body, it is a component of connective, epithelial and neuronal tissues and it forms a major element in the extracellular matrix (ECM), including the brain ECM, where its deficiency or lack can be the cause of epileptic disorders. It is present in almost all biological fluids including synovial fluid and the vitreous humour of the eye. It acts as a lubricant and shock absorber, particularly in the joints, preventing cellular damage induced by physical stress to which the cartilages are constantly subjected, helping to keep them healthy. The largest amount of HA is found in the skin that contains more than 50% of the total content within the body. In normal state, HA is present as a free polymer, however in some tissues, it is linked to different proteins to give proteoglycans or to specific cell receptors.

The main function of HA is to create volume and provide lubricants to tissues, maintaining an open, hydrated and stable extracellular space in which cells and other ECM components, such as collagen and elastin fibbers are firmly maintained. HA is also involved in cellular activity, where is responsible for the regulation of cell adhesion, cell migration and cell proliferation. In particular, high molecular weight HA exhibits anti-angiogenic and anti-inflammatory properties, whereas low molecular weight fragments (<100 kDa) have the opposite biological activity; they are inflammatory, immuno-stimulatory and angiogenic. It has been widely disclosed the functions of HA and HA fragments in wound healing, as well as in tumour growth and cancer proliferation, during which CD44 cell receptors are overexpressed. Due to the unique biological properties of HA which are very similar of that in human tissues, it has gained great attention and interest over the years. These properties have allowed HA to be used in different biomedical applications such as wound-healing, lubricant in osteoarthritis, tissue augmentation and as carrier for drug delivery system. However, native HA has very limited applications due to its poor mechanical properties and in vivo rapid degradation.

It has been disclosed in the state of the art that polysaccharides can be widely degraded. The degradation of polysaccharides, and particularly HA, can be viewed as a depolymerization process that is mediated by glycosidic bond cleavage; which mainly involves two mechanisms: the enzymatic degradation (selective and very rapid promoted by the specific enzymes hyaluronidases); and the oxidative degradation (non-selective and less rapid promoted by free radicals (ROS) and pro-oxidant enzymatic activities that could be present during inflammation of tissues). Furthermore, apart from the above-mentioned mechanisms, there is always a hydrolytic non-selective degradation mechanism due to the water and electrolytes in the tissues.

In particular, it is assumed that HA degradation is a highly organized and tightly controlled process to generate HA fragments of precisely defined size for the desired biological function. HYAL1 and HYAL2 are the most widely expressed hyaluronidases. HYAL2 (anchored on the cell membrane) cleaves high molecular weight HA (>1 MDa) into 20 kDa fragments and HYAL1 (found in lysosomes) subsequently cleaves these fragments further down to tetrasaccharides, which are then converted to monosaccharides by several enzymes of the hyaluronidase family (e.g., β-glucuronidase, β-N-acetylglucosaminidase). Because these degradation products are native to the human body, they follow the natural elimination process. As it is mentioned above, HA can also be naturally degraded in the organism by reactive oxygen species (ROS). The mechanism of HA degradation differs according to the ROS involved. Regardless of magnitude, disturbance to the tissue environment can activate the body's immune system, leading to a transient inflammatory reaction. Mechanical injury to the tissue caused by the penetration of a needle during filler injection can also lead to such a reaction. Due to the afore-mentioned degradative mechanisms, the in vivo turnover after injection of native polysaccharides is very short, such as hyaluronic acid that is less than 24 hours, depending on the specific enzymatic activity of the tissue in which it is implanted. Its in-vivo duration, and consequently its therapeutic effect, can however be further reduced following degradation by oxidative stress, due to the presence of ROS and pro-inflammatory enzymes.

To overcome these drawbacks in relation to the stability and biocompatibility of the polysaccharides, and particularly HA, several strategies for modulating the physical and mechanical properties of polysaccharides in order to enlarge the in vivo half-life of HA have been disclosed.

One of these strategies implies the preparation of cross-linked polysaccharides such as crosslinked-HA having an enhanced stability and longer residence time (i.e. a lower degradation rate). Several methods have been developed in the state in the art to produce cross-linked polysaccharide, and particularly crosslinked HA. The resultant crosslinked HA is a cross-linked HA hydrogel having a tridimensional (3D) network structure formed by covalent crosslink bonds that retains water within its network but does not dissolve in water.

Chemically cross-linked hydrogels are stable materials and show much higher resistant against enzymatic degradation than native HA due to the formation of bridges and intermolecular bonds between the HA chains and the cross-linker. Further, this 3D structure can also contribute to the resistance against oxidative degradation because their anti-inflammatory activity (polyols). The above-mentioned crosslinked HA hydrogels having the modification of the hydroxyl groups allows their used for the development of dermal fillers. In this line, several chemical cross-linkers have been disclosed in the state of the art as appropriate crosslinkers for the preparation of crosslinked polysaccharides, including methacrylamide, hydrazide, carbodiimide (EDC), divinyl sulfone (DVS), epichlorohydrin and some diepoxy compounds and diglycidyl ethers such as 1,2,7,8 diepoxyoctane, 1,4-butane diol diglycidyl ether (BDDE), poly (ethylene glycol) diglycidyl ether (PEGDE) and glycerol diglycidyl ether (GDE).

It is known in the state of the art that crosslinked polysaccharides (such as crosslinked HA hydrogels) with higher degrees of cross-linking are preferred because their higher longevity and mechanical strength in vivo. Stronger cross-linked HA hydrogel can also provide adequate force to lift the tissues and resist subsequent deformation. However, from a health perspective, incorporation of high contents of chemical cross-linkers in HA modification is not feasible. The excessive amounts of cross-linkers are often toxic for cells and tissues with which the hydrogel is in contact after implantation. In addition, an excessive amount of toxic cross-linker can interfere with cells differentiation and proliferation, and moreover can give unwanted reactions with other bioactive ingredients incorporated in the hydrogel matrix during its manufacturing (free polyols, antioxidants, amino acids, buffers, anaesthetics, drugs etc.).

Divinyl sulfone, (DVS) was the cross-linker agent used for the cross-linking of most dermal fillers on the market before the introduction of BDDE and is currently still used in some commercial products. Its ability as a cross-linking agent is attributed to the reactivity of activated vinyl groups present at the two ends of the molecule. The reaction takes place by addition on the double vinyl bond of the hydroxyl group, negatively charged in an alkaline environment (nucleophile), present on the polysaccharide chain with consequent formation of an ether bond. The reaction is a nucleophilic addition, and no molecule or group is released following the chemical reaction. However, the DVS cross-linked hyaluronic acid dermal fillers have shown some problems of enzymatic degradation, probably related to the presence of the sulfonic groups that act as enzyme inhibitors, therefore the fillers are difficult to remove by injection of hyaluronidase in case of adverse reactions after implantation. Consequently, DVS was gradually abandoned in favour of others crosslinkers such as BDDE. Furthermore, DVS is a foreign molecule, of synthetic origin and with a certain degree of toxicity superior even to BDDE, it is very volatile and irritating, and this makes it problematic even for dermal filler manufacturers.

1,4-butanediol diglycidyl ether (BDDE) and its reaction with HA has been disclosed in the state in the art. In particular, the HA solution was mixed with BDDE under alkaline conditions and an ether linkage was formed. This reaction involves epoxy ring opening process and it is carried out in an alkaline medium, where the epoxy ring reacts preferentially with the hydroxyl group to form ether bonds. BDDE is commonly used for the preparation of HA-based dermal fillers currently available on the market. Its ability to cross-link is attributed to the reactivity of the epoxy groups present at the two ends of the molecule. Although unreacted BDDE has been found to be mutagenic in the Drosophila model organism, a definitive carcinogenic effect has not been observed in mice. Despite this, and because of its mutagenic potential the amount of unreacted BDDE in dermal fillers must be maintained at trace amounts (i.e. residual level). This trace level has been determined to be safe after a Food and Drug Administration (FDA) safety risk assessment. On the other hand, hydrolysed BDDE is a diol-ether resulting from the hydrolysis of the epoxide groups in BDDE or the hydrolytic cleavage of cross-linked BDDE. However, the metabolism of hydrolysed BDDE is not described in the state of the art, it is understood to proceed through ether bond cleavage by a family of enzymes called cytochromes P450. On the contrary, both the native BDDE and the metabolized butanediol are foreign molecules, of synthetic origin (petroleum) and with a certain degree of toxicity.

Therefore, due to the potential toxicity of the BDDE and its metabolized derivative molecules, as well as the strict regulatory control of the amount of BDDE, BDDE has also been gradually substituted by other safety crosslinkers.

In order to provide safety crosslinkers for the preparation of safety crosslinked polysaccharides having improved physical and chemical properties, several studies disclosed the use of glycerol diglycidyl ether (GDE). GDE is a bis-substituted glycidyl ether of glycerol. In particular, the chemical structure of GDE can corresponds to the 1,3-GDE and 1,2-GDE as it is shown in the following formulae:

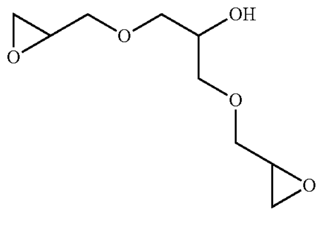

1,3-diglycidyl glycerol ether

-continued

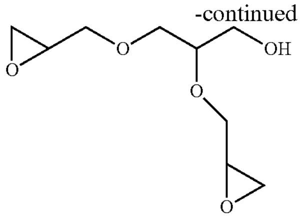

1,2-diglycidyl glycerol ether

However, in the state of the art, GDE has been erroneously called "polyglycerol polyglycidyl ether" or "polyglycerol diglycidyl ether" (PPE) because of the indetermination of its chemical structure, which is often commercially available as a mixture of the bis-substituted glycidyl ether of glycerol with the mono- and even the tri-substituted glycidyl ether of glycerol.

The use of GDE is especially advantageous because the glycerol is an endogenous molecule naturally present in all human tissues, both in circulating free form or bounded in form of triglycerides in adipose tissues or phospholipids of the cell membrane. In fact, glycerol is involved in the metabolic and catabolic processes of the body and is therefore a safe molecule. Therefore, despite the DVS and BDDE, the presence of GDE and/or its main degradation product (glycerol) does not imply potential toxicity problems. However, the main problem of the use of GDE is that for reducing the degradation rate of the resulting GDE crosslinked polysaccharides a high content of cross-linker is required.

However, crosslinked polysaccharides having a high cross-linking degree exhibit an unappropriated poor flow properties, due to the contribute of elasticity in addition to viscosity, and therefore they are difficult to extrude through thin needles, especially when used in injectable applications (fillers for aesthetic, treatment of osteoarthritis, etc.). In fact, it has been reported in the state in the art various complications and side effects correlated with the chemical cross-linkers used in HA stabilization, particularly for the HA fillers treated with excessive amounts of cross-linkers, such as undesirable pain in patients after application and poor handle for physicians. Any side effects or allergic reactions produced by HA-based fillers are thought to be caused by the cross-linkers, both unremoved during manufacturing and subsequent in vivo released after hydrogel hydrolyzation.

Thus, this field of study is currently receiving considerable attention and has become one of the major challenging issues in hydrogels manufacturing (i.e. crosslinking polysaccharide). However, when an amount of a cross-linker is reduced and consequently the crosslinking degree is reduced, the mechanical properties and/or the degradation resistance has been compromised. Furthermore, due to chemical reactions kinetics related issues, the low level of cross-linker may not quantitatively complete the chemical reaction in reasonable time, leading a grafting only without effective cross-linking of the polymer, or worse, leaving high amounts of free unreacted cross-linker in the hydrogel, which is difficult to remove and leads to high toxicity material, lowering safety of the product for the patient.

Therefore, from what it is known in the art, there is still the need to provide safety crosslinked polysaccharides having both a low amount of crosslinker and a low degree of crosslinking with adequate mechanical and enzymatic/oxidative degradation resistance.

SUMMARY OF INVENTION

The inventors of the present invention have surprisingly provided a safety crosslinked polysaccharide having appropriate mechanical properties, low enzymatic/oxidative degradation rate, and adequate biocompatibility for being used in in vivo applications.

In particular, the inventors have found that the hyperbranched polyglycerol diglycidyl ether (PPE) of the invention having a molecular weight from 750 to 15.000 Da; and an epoxy equivalent weight from 183 to 7.500 g/eq is useful as a crosslinking agent capable of reacting with the hydroxyl groups of the polysaccharide and allowing the preparation of the crosslinked polysaccharide of the invention having a low crosslinking degree; appropriate mechanical properties and degradation rate and being at the same time safety for its application into the skin.

Without being bound to any theory, the inventors attribute the mechanical properties and the degradation resistance of the PPE cross-linked polysaccharides of the present invention to a combination effect of the structure and amount of the hyperbranched PPE of the present invention, along with its cohesive properties deriving from covalent and not covalent interactions between the polysaccharide and the hyperbranched PPE of the invention. The interaction of the hyperbranched PPE of the invention with the polysaccharide create a dense three-dimensional HA network that holds the hydrogel matrix intact and limits the enzyme's ability to infiltrate the implant and degrade the three-dimensional HA network even at low cross-linking degree.

The hyperbranched PPE of the invention is prepared by a process which comprises a self-polymerization step of the starting material (i.e. GDE or non-hyperbranched PPE). The self-polymerization step implies submitting the GDE or non-hyperbranched PPE under such reaction conditions of temperature and time which allows having the appropriate molecular weight and epoxy equivalent weight as defined in the present invention.

Finally, the PPE crosslinked polysaccharides of the present invention exhibit a good flow properties, and therefore is easy to handle and extrude through thin needles, especially when used in injectable applications. Besides, the injection of the PPE crosslinked polysaccharides of the present invention render low or none pain perception by the patients during and after its application.

Then, the present invention provides a polysaccharide based hydrogel with a low degree of cross-linking, with low chemical modification and therefore molecularly and structurally very similar to native polysaccharide with the advantages of a high biocompatibility and safety profile. Surprisingly, even being low cross-linked, the polysaccharide-based hydrogel exhibits adequate mechanical properties and resistance to enzymatic and oxidative degradation with a high degree of cross-linking, with the advantage of a high longevity in vivo.

Thus, the first aspect of the invention relates to a hyperbranched PPE compound of formula (I), (I)

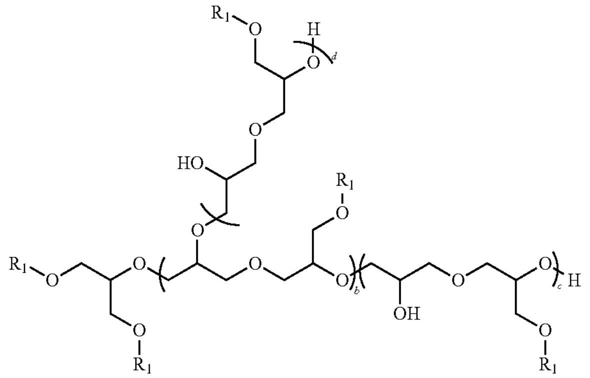

or alternatively,
a compound of formula (II)

$R_3$ is

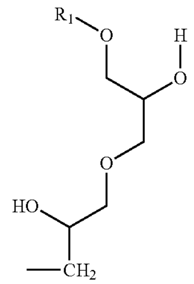

b is an integer selected from the group consisting of 1 to 70; c is an integer selected from the group consisting of 1 to 70; d is an integer selected from the group consisting of 1 to 70; having a molecular weight ($M_w$) from 750 to 15.000 Da measured by the method by liquid chromatography; and an epoxy equivalent weight from 183 to 7.000 g/eq measured by ultrasonication-assisted rapid titration with HCl.

The second aspect of the invention relates to a crosslinked polysaccharide of formula (III)

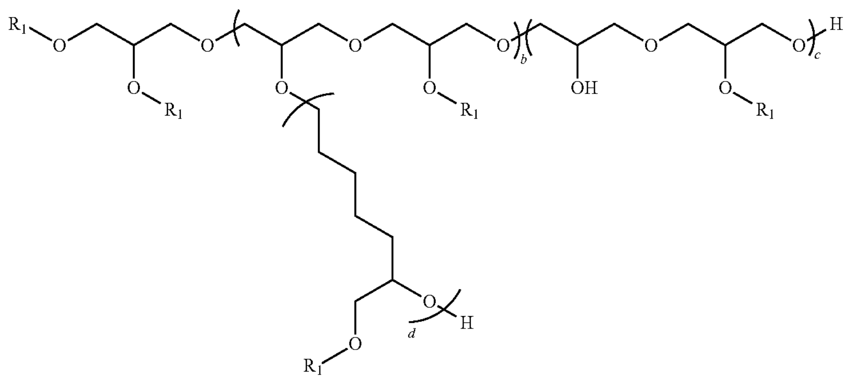

wherein each $R_1$ is independently selected from the group consisting of $R_2$ and $R_3$;

$R_2$ is

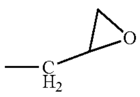

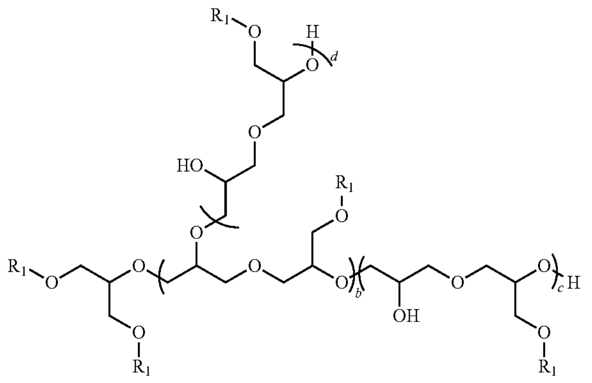

or alternatively, a crosslinked polysaccharide of formula (IV)

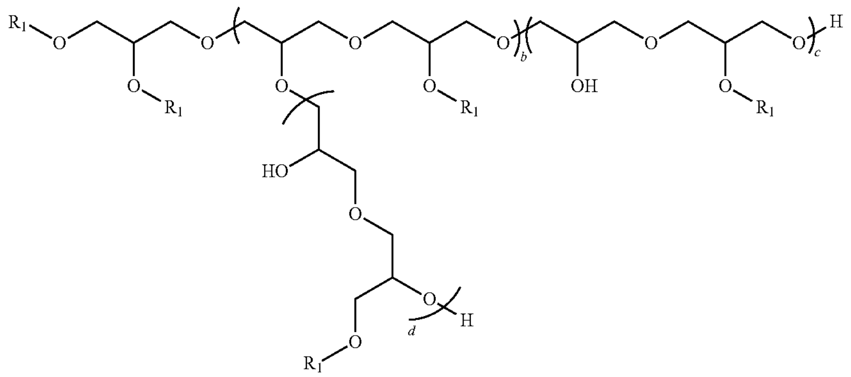

Wherein: each $R_1$ is independently selected from the group consisting of $R_2$, $R_3$, $R_4$ and $R_5$;

$R_2$ is

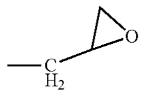

$R_3$ is

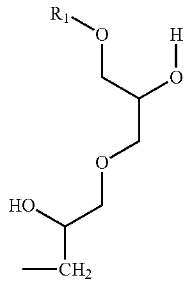

$R_4$ is

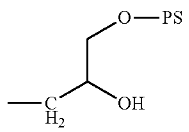

$R_5$ is

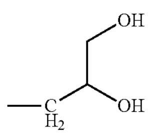

PS is a polysaccharide; and the crosslinked polysaccharide has a crosslinking percentage from 0.077 to 0.450%; particularly from 0.077 to 0.269%.

The third aspect of the invention relates to a process for the preparation of a compound (I) or alternatively of a compound of formula (II) of the first aspect of the invention; wherein: when the compound is a compound of formula (I), then the process comprises: a) providing an alkaline solution containing 1,3-glycerol diglycidyl ether; and b) maintaining the solution obtained in step a) at a temperature from 10 to 80° C. for a period of time from 1 min to 30 days; or alternatively, when the compound is a compound of formula (II), then the process comprises: c) providing an alkaline solution containing 1,2-glycerol diglycidyl ether; and d) maintaining the solution obtained in step c) at a temperature from 10 to 80° C. for a period of time from 1 min to 30 days.

The fourth aspect of the invention relates to a process for the preparation of the crosslinked polysaccharide of the second aspect of the invention, which comprises crosslinking the polysaccharide with a compound of formula (I); or alternatively with a compound of formula (II) as defined in the first aspect of the invention.

The fifth aspect of the invention relates to a composition comprising one or more of the crosslinked polysaccharides of the second aspect of the invention.

The sixth aspect of the invention relates to the use of the hyperbranched PPE of the first aspect of the invention as crosslinking agent.

And, finally, the use of the crosslinked polysaccharide of the second aspect of the invention in the field of pharmacy, cosmetic, food and agriculture.

In particular, it is part of the invention a crosslinked polysaccharide as defined in the second aspect of the invention wherein the polysaccharide is hyaluronic acid for use in therapy. And, the use of a crosslinked polysaccharide as defined in the second aspect of the invention wherein the polysaccharide is hyaluronic acid as dermal filler.

DETAILED DESCRIPTION OF THE INVENTION

All terms as used herein in this application, unless otherwise stated, shall be understood in their ordinary meaning as known in the art. Other more specific definitions terms as used in the present application are as set forth below and are intended to apply uniformly throughout the specification and claims unless an otherwise expressly set out definition provides a broader definition.

For the purposes of the present invention, any ranges given include both the lower and the upper endpoints of the range. Ranges given, such as temperatures, times, weights, and the like, should be considered approximate, unless specifically stated.

The term "percentage (%) by weight" refers to the percentage of each moiety or each ingredient in relation to the total weight.

As it is disclosed above, the first aspect of the present invention is a compound of formula (I); or alternatively a compound of formula (II).

The compound of formula (I) is obtained by submitting the 1,3-GDE or a non-hyperbranched PPE obtained from 1,3-GDE to the self-polymerization step as defined in the process of the invention. Alternatively, the compound of formula (II) is obtained by submitting the 1,2-GDE or a non-hyperbranched PPE obtained from 1,2-GDE to the self-polymerization step as defined in the process of the invention.

For the purpose of the invention, the PPE disclosed in the state of the art is a branched PPE but not a hyperbranched PPE. The branched PPE of the state of the art is prepared by reaction of glycerol and epichlorohydrin, whose molecular weight can be adjusted increasing the amount of epichlorohydrin. However, those processes do not comprise a self-polymerization step as the process of the present invention. As a result, the branched PPE of the state of the art (commercially available with the tradename Denacol®) is structurally different from the hyperbranched PPE of the present invention. In particular, the structures of the branched PPE disclosed in the state of the art, which fall outside the scope of the present invention are the following:

In an embodiment, the compound of formula (I) or alternatively the compound of formula (II) has a molecular weight from 800 to 7000 Da by liquid chromatography; and an epoxy equivalent weight from 195 to 700 g/eq measured by ultrasonication-assisted rapid titration with HCl. In an embodiment, the compound of formula (I) or alternatively the compound of formula (II) has a molecular weight from 900 to 4500 Da by liquid chromatography; and an epoxy equivalent weight from 200 to 600 g/eq measured, by ultrasonication-assisted rapid titration with HCl.

In an embodiment, the compound of formula (I) or alternatively the compound of formula (II) has a polydispersity index equal to or less than 1.8 measured by liquid chromatography. In an embodiment, the compound of formula (I) or alternatively the compound of formula (II) has a polydispersity index equal to or less than 1.6 measured by liquid chromatography, particularly by using a GPC instrument equipped with light scattering detector.

The term "polydispersity index", "heterogeneity index" and "dispersity" have the same meaning and are used interchangeable. They refer to a measure of the heterogeneity of sizes of molecules or particles in a mixture, particularly the distribution of the molecular mass in a given

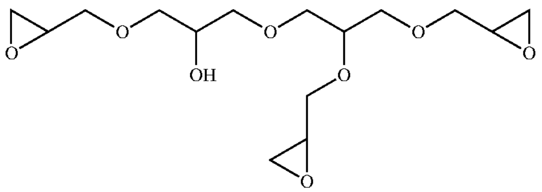

Denacol EX-421 MW = 334.37

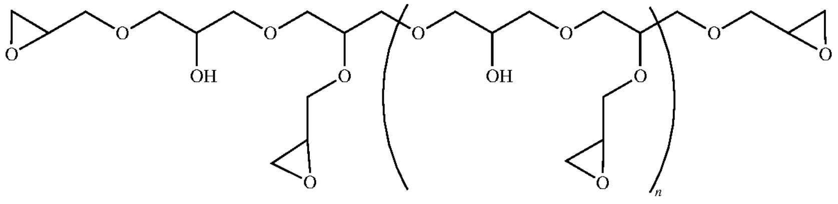

n = 1 Denacol EX-512 MW = 539
n = 2 Denacol EX-521 MW = 743

The compound of formula (I) or alternatively the compound of formula (II) has a molecular weight from 750 to 15.000 Da measured by liquid chromatography; and an epoxy equivalent weight from 183 to 7.500 g/eq measured by ultrasonication-assisted rapid titration with HCl.

The term "epoxy equivalent weight", "average EEW" and the abbreviation "EEW" have the same meaning and they are used interchangeable. The EEW is the weight of crosslinking agent, in grams, which contains one gram-equivalent of epoxy. EEW refers to the content of epoxy groups present in one gram of the crosslinking agents disclosed in the present invention and expressed in g/eq. The EEW was experimentally measured using the quantitative ultrasonication-assisted titration with HCl for the rapid determination of epoxides disclosed in the state of the art (He, Z., et al., "Ultrasonication-assisted rapid determination of epoxide values in polymer mixtures containing epoxy resin". Analytical Methods, 2014, vol. 6(12), pp. 4257-4261).

The measurement of the molecular weight and the polydispersity index were performed by liquid chromatography, particularly using a GPC instrument equipped with light scattering detector.

polymer sample. It is represented by the symbol Đ. For the purpose of the present invention, the polydispersity index refers to the molecular mass, which can be calculated using the following equation $$Đ_M = M_w/M_n$$

wherein $M_w$ is the weight-average molar mass and $M_n$ is the number-average molar mass.

The terms "molecular weight", "average molecular weight", "weight-average molar mass", "mass average molar mass", "average Mw" and the abbreviation "$M_w$" have the same meaning and they are used interchangeable. The mass average molar mass is calculated by the following equation:

$$M^{-}w = \sum i N i M i 2 \sum i N i M i$$

$$\overline{M}_w = \frac{\sum_i N_i M_i^2}{\sum_i N_i M_i}$$

-continued

{\displaystyle {\bar {M}}_{w} =

{\frac {\sum_{i}N_{i}M_{i}^{2}}{\sum_{i}N_{i}M_{i}}}} where N i {\displaystyle N_{i}} $N_i$ is the number of molecules of molecular mass M i {\displaystyle M_{i}} $M_i$. The mass average molecular mass can be determined by static light scattering, small angle neutron scattering, X-ray scattering, and sedimentation velocity.

The terms "number-average molar mass" and the abbreviation "Mn" have the same meaning and they are used interchangeable. Mn is a way of determining the molecular mass of a polymer. Polymer molecules, such as polysaccharides, even ones of the same type, come in different sizes (chain lengths, for linear polymers), so the average molecular mass will depend on the method of averaging. The number average molecular mass is the ordinary arithmetic mean or average of the molecular masses of the individual macromolecules. It is determined by measuring the molecular mass of n polymer molecules, summing the masses, and dividing by n. Mn is calculated by the following equation:

$$\overline{M}_n = \frac{\sum_i N_i M_i}{\sum_i N_i}$$

where N i {\displaystyle N_{i}} $N_i$ is the number of molecules of molecular mass M i {\displaystyle M_{i}} $M_i$. The number average molecular mass of a polymer can be determined by gel permeation chromatography, viscometry via the (Mark-Houwink equation), colligative methods such as vapor pressure osmometry, end-group determination or proton NMR.

Polymer's fragments with different molecular weight can be prior separated by liquid chromatography using GPC instrument and revealed or detected by mean of the equipped light scattering detector, before the evaluation of the weight-average molar mass "Mw" and the number-average molar mass "Mn" of each fragment, performed by the instrument itself and using standards with certified Mw.

In an embodiment, the hyperbranched PPE of the present invention is the compound of formula (I)-16:

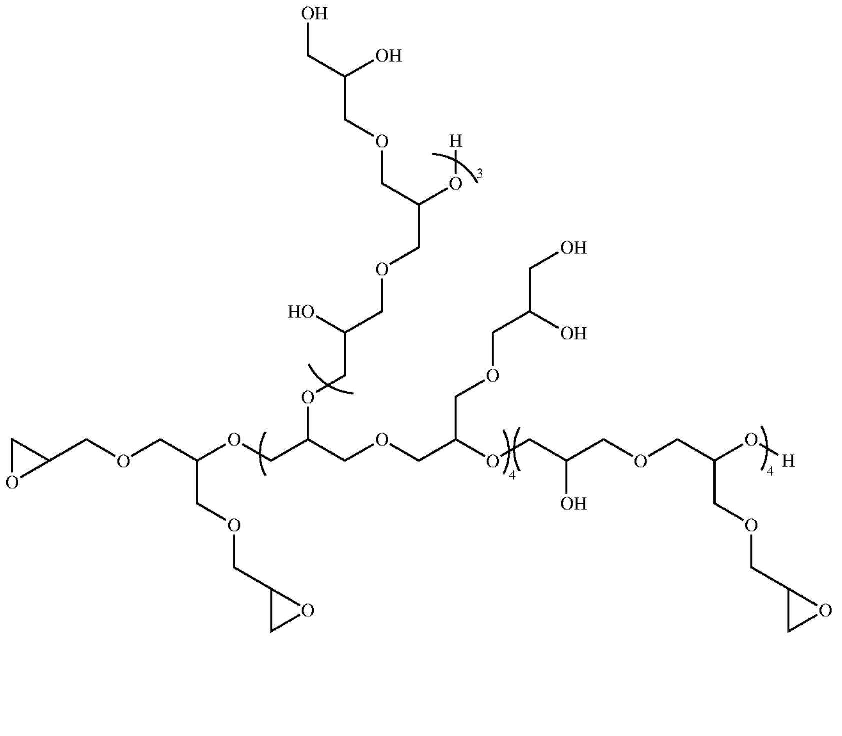

wherein the average Mw is 3530 g/mole; the average EEW is 589 g/eq and the Mw/Mn is 1.53.

In an embodiment, the hyperbranched PPE of the present invention is the compound of formula (I)-22:

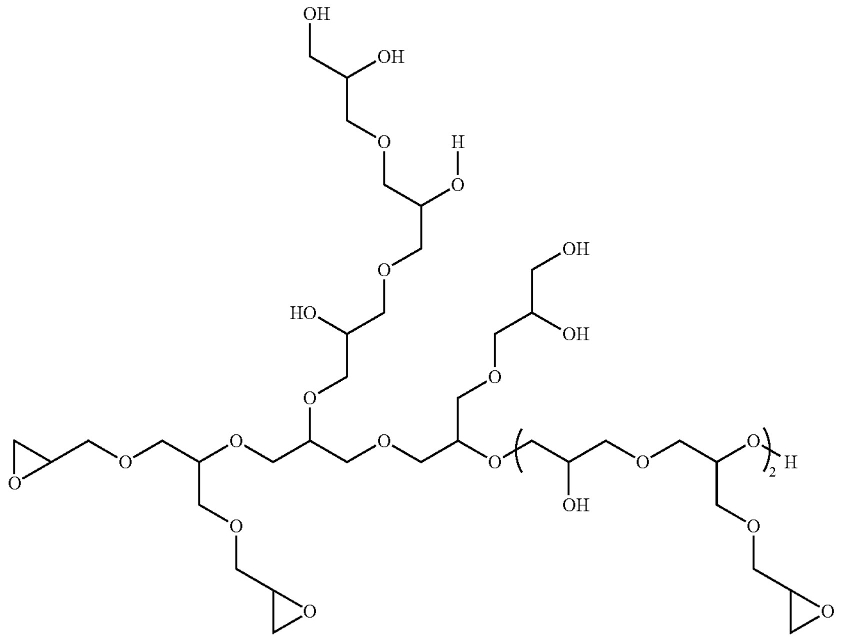

wherein the average Mw is 910 g/mole; the average EEW is 229 g/eq and the Mw/Mn is 1.36.

In an embodiment, the hyperbranched PPE of the present invention is the compound of formula (I)-23:

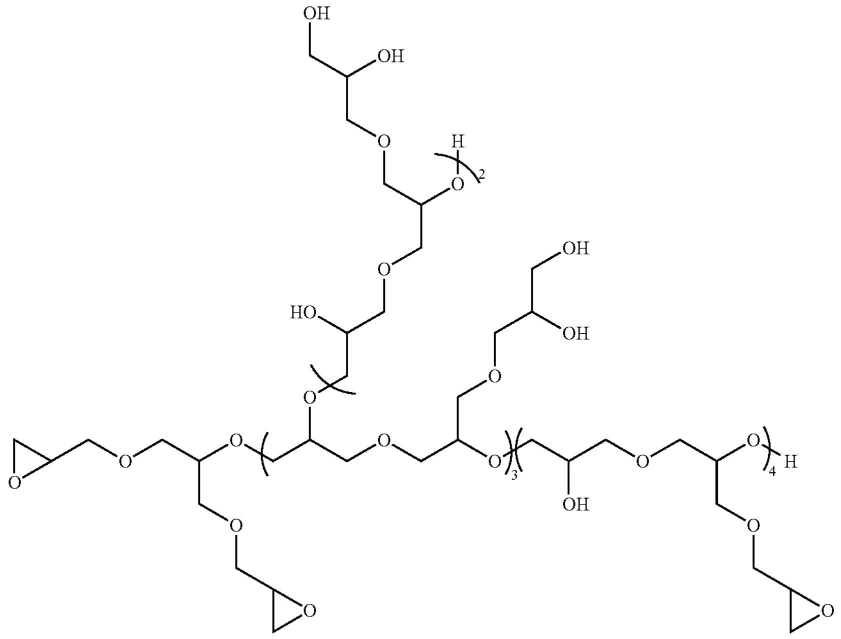

wherein the average Mw is 2400 g/mole; the average EEW is 404 g/eq and the Mw/Mn is 1.54.

In an embodiment, the hyperbranched PPE of the present invention is the compound of formula (I)-14:

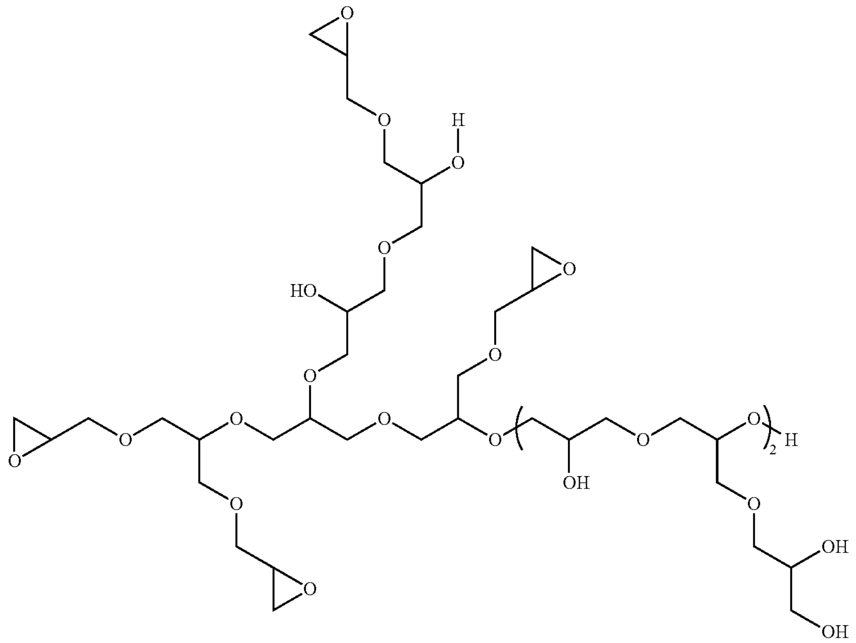
wherein the average Mw is 940 g/mole; the average EEW is 234 g/eq and the Mw/Mn is 1.36.
In an embodiment, the hyperbranched PPE of the present invention is the compound of formula (I)-28:
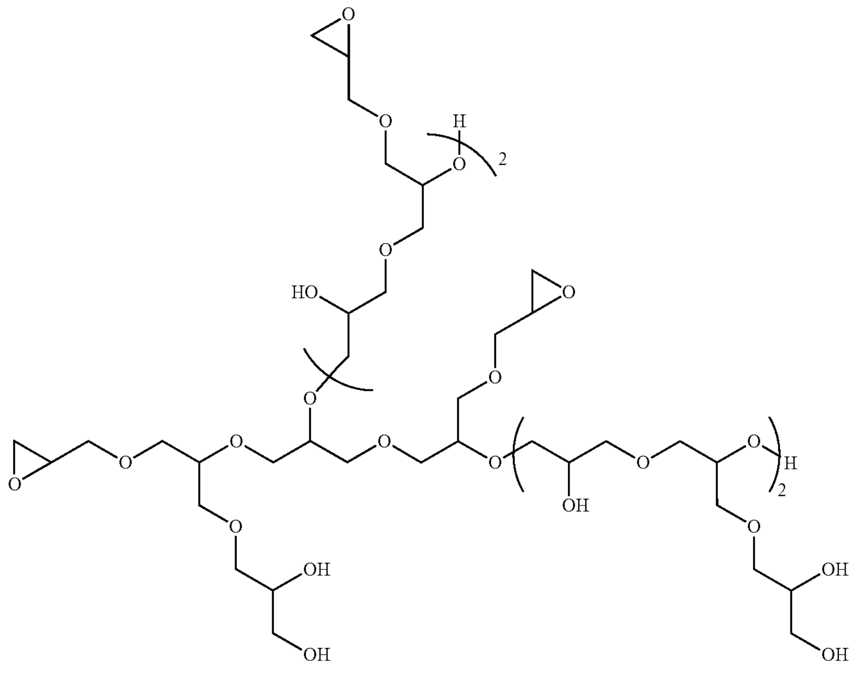
wherein the average Mw is 990 g/mole; the average EEW is 247 g/eq and the Mw/Mn is 1.37.
In an embodiment, the hyperbranched PPE of the present invention is the compound of formula (I)-26:

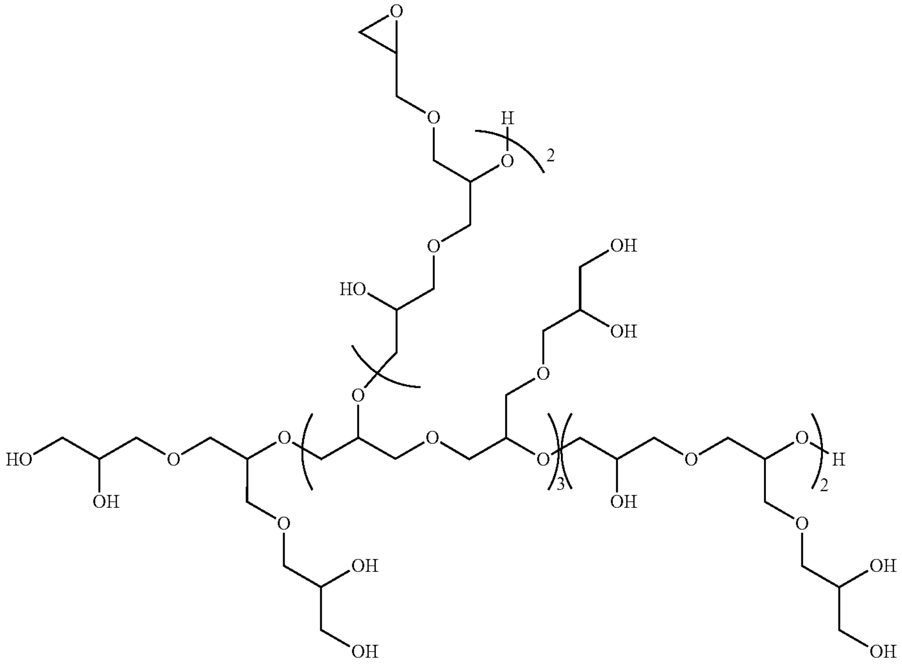

wherein the average Mw is 2200 g/mol; the average EEW is 365 g/eq and the Mw/Mn is 1.47.

In an embodiment, the hyperbranched PPE of the present invention is the compound of formula (I)-21:

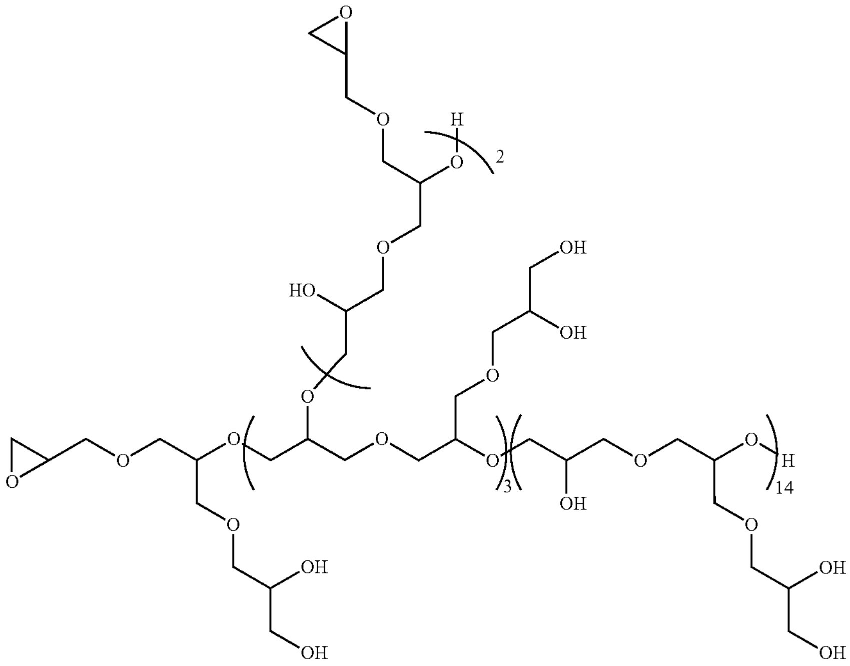

wherein the average Mw is 4200 g/mole; the average EEW is 585 g/eq and the Mw/Mn is 1.55.

Another aspect of the present invention is a process for the preparation of the compound of formula (I) or alternatively a compound of formula (II).

The process for the preparation of a compound of formula (I) of the present invention comprises:

a) providing an alkaline solution containing 1,3-glycerol diglycidyl ether (1,3-DGE); and b) maintaining the solution obtained in step a) at a temperature from 10 to 80° C. for a period of time from 1 min to 30 days;

The process for the preparation of a compound of formula (II) of the present invention comprises:

c) providing an alkaline solution containing 1,2-glycerol diglycidyl ether (1,2-DGE); and d) maintaining the solution obtained in step c) at a temperature from 10 to 80° C. for a period of time from 1 min to 30 days.

The 1,3-GDE and 1,2-GDE have been previously disclosed in the state of the art, and they are commercially available (cf. experimental section).

In an embodiment, the alkaline solution of step a) or alternatively of step c) comprises a base selected from the group consisting of physiologically acceptable alkaline metal or ammonium hydroxides (Na, K), alkaline earth metal hydroxides (Mg, Ca, Sr), physiologically acceptable heavy metal hydroxides (Fe, Al, Co, Cu, Se, Zn, Cr, Ni), physiologically acceptable quaternary ammonium cations hydroxides, physiologically acceptable heavy metal or ammonium hydrogen carbonate ($NH_4$, Fe, Al, Co, Cu, Se, Zn, Cr, Ni) and mixture thereof.

The term "physiologically acceptable" refers to a non-toxic material that is compatible with a biological system such as a cell, cell culture, tissue, or organism. Preferably, the biological system is a living organism, such as a mammal, particularly a human.

In an embodiment, the alkaline solution of step a) or alternatively of step c) comprises an alkaline metal or ammonium hydroxide selected from the group consisting of potassium hydroxide (KOH), sodium hydroxide (NaOH), ammonium hydroxide and a mixture thereof; particularly sodium hydroxide.

In an embodiment, the alkaline solution of step a) or alternatively of step c) comprises an alkaline earth metal hydroxide selected from the group consisting of magnesium hydroxide, calcium hydroxide, strontium hydroxide and a mixture thereof.

In an embodiment, the alkaline solution of step a) or alternatively of step c) comprises an heavy metal hydroxides selected from the group consisting of iron hydroxide, aluminium hydroxide, cobalt hydroxide, selenium hydroxide, tin hydroxide, chromium hydroxide, nickel hydroxide and a mixture thereof.

In an embodiment, the alkaline solution of step a) or alternatively of step c) comprises a quaternary ammonium hydroxides of formula $HONR_6R_7R_8R_9$ wherein each one of $R_6$, $R_7$, $R_8$ and $R_9$ is independently selected from the group consisting of ($C_1$-$C_8$) alkyl, or alternatively two of $R_5$, $R_6$, $R_7$ and $R_9$ form a ($C_5$-$C_6$) cycloalkyl ring.

In an embodiment, the alkaline solution of step a) or alternatively of step c) comprises heavy metal or ammonium hydrogen carbonate selected from the group consisting of iron hydrogen carbonate, aluminium hydrogen carbonate, cobalt hydrogen carbonate, Cupper hydrogen carbonate, selenium hydrogen carbonate, zinc hydrogen carbonate, chromium hydrogen carbonate, nickel hydrogen carbonate, ammonium hydrogen carbonate and a mixture thereof; particularly sodium hydrogen carbonate.

In an embodiment, the alkaline solution of step a) or alternatively of step c) comprises from 1 to 50 percent by weight of 1,3-GDE or alternatively of 1,2-GDE. In an embodiment, the alkaline solution of step a) or alternatively of step c) comprises an alkaline hydroxide and comprises from 1 to 50 percent by weight of 1,3-GDE or alternatively of 1,2-GDE. In an embodiment, the alkaline solution of step a) or alternatively of step c) comprises an alkaline hydroxide selected from the group consisting of potassium hydroxide (KOH), sodium hydroxide (NaOH) and a mixture thereof and comprises from 1 to 50 percent by weight of 1,3-GDE or alternatively of 1,2-GDE. In an embodiment, the alkaline solution of step a) or alternatively of step c) comprises sodium hydroxide (NaOH) and comprises from 1 to 50 percent by weight of 1,3-GDE or alternatively of 1,2-GDE.

In an embodiment, step a) or alternatively step c) of the process of the invention is performed at room temperature. The term "room temperature" refers to a temperature at about 25 to 35° C. In an embodiment, step a) or alternatively step c) of the process of the invention is performed in the presence of a solvent. In an embodiment, step a) or alternatively step c) of the process of the invention is performed in the presence of a solvent selected from the group consisting of water, ($C_1$-$C_4$) alkyl-OH, ($C_1$-$C_4$) alkyl-CO—($C_1$-C) alkyl, ($C_1$-$C_4$) alkyl-CO—O—($C_1$-$C_4$) alkyl, ($C_1$-$C_4$) alkyl-CN, and mixtures thereof. In an embodiment, step a) or alternatively step c) of the process of the invention is performed in the presence of a solvent selected from the group consisting of methanol, ethanol, 1-propanol, 2-propanol, acetone, acetonitrile, ethyl acetate and mixture thereof; particularly the solvent is water.

The term "alkyl" refers to a saturated straight, or branched hydrocarbon chain which contains the number of carbon atoms specified in the description or claims. Examples include, among others, the group methyl, ethyl, propyl, isopropyl, butyl, isobutyl, sec-butyl, and tert-butyl.

In an embodiment, step b) or alternatively step d) is performed by submitting the 1,3-GDE or alternatively the 1,2-GDE at a temperature from 10 to 80° C. for a period of time from 1 min to 30 days during which self-polymerization of GDE take places.

In an embodiment, step b) or alternatively step d) is performed by submitting the 1,3-GDE or alternatively the 1,2-GDE at a temperature in the range from 50 to 80° C. for a period from 1 minute to 500 minutes. In an embodiment, step b) or alternatively step d) is performed by submitting the 1,3-GDE or alternatively the 1,2-GDE at a temperature in the range from 50 to 80° C. for a period from 5 to 60 minutes.

In an embodiment, step b) or alternatively step d) is performed by submitting the 1,3-GDE or alternatively the 1,2-GDE at a temperature in the range from 10 to 40° C. for a period from 1 day to 30 days. In an embodiment, step b) or alternatively step d) is performed by submitting the 1,3-GDE or alternatively the 1,2-GDE at a temperature from 10 to 40° C. for a period from 2 day to 7 days.

It is also part of the present invention a compound of formula (I) or alternatively a compound of formula (II) obtainable by the process as defined above, which comprises the self-polymerization step b), or alternatively step d) as defined above.

For the purposes of the invention the expressions "obtainable", "obtained" and equivalent expressions are used interchangeably, and in any case, the expression "obtainable" encompasses the expression "obtained".

All embodiments disclosed above for the process for the preparation of the compound of formula (I) or alternatively the compound of formula (II) also apply to the compound of formula (I) or alternatively the compound of formula (II) obtainable by the process of the invention.

It is also part of the invention the use of the hyperbranched PPE of the invention as crosslinking agent.

The second aspect of the invention relates to a crosslinked polysaccharide of formula (III) or alternatively a crosslinked polysaccharide of formula (IV) having a crosslinking percentage from 0.077 to 0.450%. In an embodiment, the crosslinked polysaccharide of formula (III) or alternatively a crosslinked polysaccharide of formula (IV) having a crosslinking percentage from 0.077 to 0.360%. In an embodiment, the crosslinked polysaccharide of formula (III) or alternatively a crosslinked polysaccharide of formula (IV) having a crosslinking percentage from 0.077 to 0.269%.

In an embodiment, the crosslinked polysaccharide of formula (III) or alternatively a crosslinked polysaccharide of formula (IV) is one wherein the polysaccharide is hyaluronic acid as defined below and the crosslinking percentage is from 0.077 to 0.450%. In an embodiment, the crosslinked polysaccharide of formula (III) or alternatively a crosslinked polysaccharide of formula (IV) is one wherein the polysaccharide is hyaluronic acid as defined below and the crosslinking percentage is from 0.077 to 0.360%. In an embodiment, the crosslinked polysaccharide of formula (III) or alternatively a crosslinked polysaccharide of formula (IV) is one wherein the polysaccharide is hyaluronic acid as defined below and the crosslinking percentage is from 0.077 to 0.269%. In an embodiment, the crosslinked polysaccharide of formula (III) or alternatively a crosslinked polysaccharide of formula (IV) is one wherein the polysaccharide is hyaluronic acid as defined below and the crosslinking percentage is from 0.077 to 0.140%.In an embodiment, the crosslinked polysaccharide of formula (III) or alternatively a crosslinked polysaccharide of formula (IV) is one wherein the polysaccharide is hyaluronic acid as defined below and the crosslinking percentage is from 0.140 to 0.450%. In an embodiment, the crosslinked polysaccharide of formula (III) or alternatively a crosslinked polysaccharide of formula (IV) is one wherein the polysaccharide is hyaluronic acid as defined below and the crosslinking percentage is from 0.140 to 0.360%. In an embodiment, the crosslinked polysaccharide of formula (III) or alternatively a crosslinked polysaccharide of formula (IV) is one wherein the polysaccharide is hyaluronic acid as defined below and the crosslinking percentage is from 0.140 to 0.269%. In an embodiment, the crosslinked polysaccharide of formula (III) or alternatively a crosslinked polysaccharide of formula (IV) is one wherein the polysaccharide is hyaluronic acid as defined below and the crosslinking percentage is from 0.270 to 0.450%. In an embodiment, the crosslinked polysaccharide of formula (III) or alternatively a crosslinked polysaccharide of formula (IV) is one wherein the polysaccharide is hyaluronic acid as defined below and the crosslinking percentage is from 0.270 to 0.360%.

In an embodiment, the crosslinked polysaccharide of formula (III) or alternatively a crosslinked polysaccharide of formula (IV) is one wherein the polysaccharide is amylose starch as defined below and the crosslinking percentage is from 0.124 to 0.204%. In an embodiment, the crosslinked polysaccharide of formula (III) or alternatively a crosslinked polysaccharide of formula (IV) is one wherein the polysaccharide is amylose as defined below and the crosslinking percentage is from 0.155 to 0.182%. In an embodiment, the crosslinked polysaccharide of formula (III) or alternatively a crosslinked polysaccharide of formula (IV) is one wherein the polysaccharide is sodium carboxymethyl cellulose as defined below and the crosslinking percentage is from 0.140 to 0.204%.

In one embodiment, in the crosslinked polysaccharides of formula (III) and (IV), the amount of $R_2$ is lower than $R_5$ on the total weight of the crosslinked polysaccharides of formula (III) and (IV). In one embodiment, in the crosslinked polysaccharides of formula (III) and (IV), the amount of $R_2$ is lower than 2 ppm on the total weight of the crosslinked polysaccharides of formula (III) and (IV). The amount of $R_2$ is experimentally measured using the quantitative ultrasonication-assisted titration with HCl for the rapid determination of epoxides disclosed in He, Z., et al., "Ultrasonication-assisted rapid determination of epoxide values in polymer mixtures containing epoxy resin". Analytical Methods, 2014, vol. 6(12), pp. 4257-4261.

The polysaccharide of the present invention is a "crosslinked" polysaccharide. The term "crosslinked" refers to a polysaccharide that have three-dimensional crosslink network wherein the network is formed by a starting polysaccharide that has been collapsed by one or more crosslinking agents. The term "crosslinking" refers in the polymer science field to the use of cross-links to promote a difference in the physical properties of the polymers (polysaccharide). The term "crosslink" refers to bonds that is formed by the aperture of the epoxide ring of the hyperbranched PPE crosslinking agent of the present invention by the hydroxyl group of the polymer (polysaccharide). The term "crosslinker" or "crosslinking agent" which is herein used interchangeably refers to a compound having the ability to cross-link one or more polymer chains.

The terms "crosslinking percentage", "percentage (%) of crosslinking", "cross-linking degree" and the abbreviation "C.D." have the same meaning and they are used interchangeable. They refer to the ratio of PPE modified polysaccharide monomeric units to unmodified polysaccharide monomeric units expressed in percentage. Commonly, the measurement of the cross-linking degree (C.D.) of materials could be evaluated using different methods well known in the state of the art. Some methods are direct, such as $^1$H NMR or quantitative GPC analysis of polymer's fragments after enzymatic digestion. Other methods are indirect, by rheological measurements, by compression or by oscillatory tests. Normally all these methods are comparative and allow to distinguish different cross-linking degree inside the same polymer's family. In the present invention, the cross-linking degree value is mathematically calculated from the value of G' obtained by rheological measurements using the following equation 1:

$$C.D.(\%) = \frac{100 * MW_{rep.unit}}{M_e}$$

wherein:

$MW_{rep.\ unit}$ is the molecular weight of the polysaccharide monomeric repeating unit, $MW_{rep.\ unit}$=401 Da for Hyaluronic acid;

$MW_{rep.\ unit}$=162 Da for amylose/glycogen;

$MW_{rep.\ unit}$=242 Da for Sodium Carboxymethyl Cellulose.

Me is mathematically calculated using the inverse formula of the following equation 2:

$$G' \cong \frac{R \cdot T \cdot c}{M_e}\left(1 - 2\frac{M_e}{M_n}\right) \quad \text{(Eq. 2)}$$

Wherein:

G' is experimentally obtained by rheological measurements using rotational rheometer, R·T is the thermal energy, c is the polysaccharide concentration, Mn is the number average molecular mass of the polysaccharide.

In the present invention, the absolute enzymatic and oxidative degradation rate for each crosslinked polysaccharide hydrogel, is mathematically calculated. Depending of the polysaccharidic substrate, three methods are used for monitoring the absolute enzymatic and oxidative degradation rate of the crosslinked polysaccharide hydrogels.

The first method is based on the monitoring of rheological parameters like the storage modulus G' during the degradation, the degradation $rate_{rheo}$ is calculated form eq. 3.

$$\text{degradation } rate_{rheo} = -\frac{G'_t - G'_{t0}}{t - t0} \quad \text{(Eq. 3)}$$

A decrease of storage modulus G' is observed during the degradation of the crosslinked polysaccharide hydrogels, caused by the disruption of the hydrogel network, $G'_t<G'_{t0}$ and the negative sign is required to have a positive degradation rate. This first method is appropriate for determining the absolute enzymatic and oxidative degradation rate of the crosslinked polysaccharide hydrogel containing hyaluronic acid, starch and derivative thereof, glycogen, cellulose and derivative thereof, pectin, lignin, inulin, guar gum, xanthan gum, alginic acids (alginates), glucomannan, galactomannan and carrageenan.

The second method is based on the monitoring of viscous parameters, like the dynamic viscosity η during the degradation, the degradation $rate_{visc}$ is calculated form eq. 4.

$$\text{degradation } rate_{visc} = -\frac{\eta_t - \eta_{t0}}{t - t0} \quad \text{(Eq. 4)}$$

A decrease of the dynamic viscosity η is observed during the degradation of the crosslinked polysaccharide hydrogels, caused by the reduction of the polymeric chains' length, $\eta_t<\eta_{t0}$ and the negative sign is required to have a positive degradation rate. This second method is appropriate for determining the absolute enzymatic and oxidative degradation rate of the crosslinked polysaccharide hydrogel containing hyaluronic acid, starch and derivative thereof, glycogen, cellulose and derivative thereof, pectin, lignin, inulin, guar gum, xanthan gum, alginic acids (alginates), glucomannan, galactomannan and carrageenan.

The third method is based on the colorimetric monitoring of the concentration of uronic acid with the carbazole assay using a spectrophotometer instrument during the degradation, the degradation $rate_{color}$ is calculated form eq. 5.

$$\text{degradation } rate_{color} = \frac{[\text{uronic acid}]_t - [\text{uronic acid}]_{t0}}{t - t0} \quad \text{(Eq. 5)}$$

An increase of the concentration of uronic acid is observed during the degradation of the crosslinked polysaccharide hydrogels, caused by the reduction of the polymeric chains' length and formation of monomeric units of uronic acid, $[\text{uronic acid}]_t>[\text{uronic acid}]_{t0}$ in this case any negative sign is required to have a positive degradation rate. This third method is appropriate for determining the absolute enzymatic and oxidative degradation rate of the crosslinked polysaccharide hydrogel containing hyaluronic acid, pectin, heparin, chondroitin sulphate, dermatan sulphate, xanthan, glucuronan, alginic acids (alginates).

In the present invention, a comparison between the absolute enzymatic and oxidative degradation rate of crosslinked polysaccharide hydrogels is also made. At a fixed period of time, the relative enzymatic and oxidative degradation rate for each crosslinked polysaccharide hydrogel is calculated as percentage of the value of absolute enzymatic and oxidative degradation rate of the crosslinked polysaccharide hydrogel over the value of absolute enzymatic and oxidative degradation rate of the polysaccharide hydrogel crosslinked with GDE known in the state of the art used as reference. Thus, it is calculated form eq. 6.

$$\%\ \text{relative degradation rate} = \frac{\text{degradation } rate_{xl}}{\text{degradation } rate_{GDE}} \cdot 100 \quad \text{(Eq. 6)}$$

wherein:

degradation $rate_{xl}$ is the absolute degradation rate of polysaccharide hydrogel crosslinked with BDDE, PEGDE and PPE degradation $rate_{GDE}$ is the absolute degradation rate of crosslinked polysaccharide hydrogel with GDE known in the state of the art.

In an embodiment, the crosslinked polysaccharide of the present invention has a relative enzymatic degradation rate from 100% to 37% of the enzymatic degradation rate of the comparative GDE cross-linked polysaccharides (which is used as reference value and internal reference). The GDE cross-linked polysaccharide used as internal value is obtained by reacting the polysaccharide with the commercial GDE (as shown in the experimental section). In an embodiment, the crosslinked polysaccharide of the present invention has a relative enzymatic degradation rate from 85 to 40%. In an embodiment, the crosslinked polysaccharide of the present invention has a crosslinking percentage from 0.1528 to 0.1877% and a relative enzymatic degradation rate from 84 to 37%.

In an embodiment, the crosslinked polysaccharide of the present invention has a relative oxidative degradation rate from 100% to 76% of the oxidative degradation rate of the comparative GDE cross-linked polysaccharides (which is used as reference value and internal reference). The GDE cross-linked polysaccharide used as internal value is obtained by reacting the polysaccharide with the commercial GDE (as shown in the experimental section). In an embodiment, the crosslinked polysaccharide of the present invention has a relative oxidative degradation rate from 90 to 75%. In an embodiment, the crosslinked polysaccharide of the present invention has a crosslinking percentage from 0.1528 to 0.1877% and an oxidative degradation rate from 76 to 87%.

As it is mentioned above, the absolute enzymatic and oxidative degradation rates of the crosslinked polysaccharides of the present invention are equal to or lower than the absolute enzymatic and oxidative degradation rate of the comparative GDE cross-linked polysaccharide used as internal reference, and having a lower crosslinking degree. It is advantageous because both the stability of the hydrogel and the patient safety and comfortability are increased.

In an embodiment, the crosslinked polysaccharide of the present invention has an absolute enzymatic degradation rate from 0.8 to 3.5 mmole/h; and an absolute oxidative degradation rate from 3.0 to 4.3 mmole/h. In an embodiment, the crosslinked polysaccharide of the present invention has an absolute enzymatic degradation rate from 0.8 to 2.6 mmole/h; and an absolute oxidative degradation rate from 3.0 to 3.4 mmole/h. In an embodiment, the crosslinked polysaccharide of the present invention has a crosslinking percentage from 0.1528 to 0.1877%, an enzymatic degradation rate from 0.8 to 2.7 mmole/h, and an oxidative degradation rate from 3.0 to 3.4 mmole/h.

In an embodiment, the crosslinked polysaccharide of the present invention is one wherein the average distance ($D_N$) between two crosslinking groups is from 21 nm to 42 nm. In an embodiment, the crosslinked polysaccharide of the present invention is one wherein the average distance ($D_N$) between two crosslinking groups is from 21 nm to lower than 27 nm. In an embodiment, the crosslinked polysaccharide of the present invention is one wherein the average distance ($D_N$) between two crosslinking groups is from equal to or higher than 27 nm to 42 nm.

In an embodiment, the crosslinked polysaccharide of the present invention is one wherein the concentration of the polysaccharide is from 1 to 50 mg/ml. The concentration of the polysaccharide can be measured by any appropriate method disclosed in the state of the art. In the present invention the concentration of the polysaccharide is measured by gravimetric measurement of dry residue obtained after dehydration of the hydrogel in ventilated oven at 105° C. for a suitable time.

In an embodiment, the crosslinked polysaccharide of the present invention is one wherein the viscosity is from 1 to 200 Pa·s measured by viscometer. In an embodiment, the crosslinked polysaccharide of the present invention is one wherein the viscosity is from 10 to 100 Pa·s measured by viscometer.

In an embodiment, the crosslinked polysaccharide of the present invention is one wherein the polysaccharide is selected from the group consisting of hyaluronic acid, starch and a derivative thereof, glycogen, cellulose and a derivative thereof, pectin, lignin, inulin, guar gum, xanthan gum, alginic acids (alginates), heparin, chondroitin sulphate, dermatan sulphate, glucuronan, glucomannan, galactomannan and carrageenans.

In an embodiment, the crosslinked polysaccharide of the present invention is one wherein the polysaccharide is hyaluronic acid. For the purpose of the present invention the term "Hyaluronic acid", "hyaluronan" and the abbreviation "HA" have the same meaning and are used interchangeable. They refer to the natural, non-sulphated anionic form of glycosaminoglycan having the CAS number 9004-61-9, being composed of several repeated disaccharide units of N-acetyl-D-glucosamine and D-glucuronic acid; and also, to its pharmaceutically or cosmetically acceptable salt of hyaluronic acid.

For the purpose of the present invention the term "hyaluronic acid" also encompasses its pharmaceutically or cosmetically acceptable salt of hyaluronic acid. In an embodiment, the crosslinked polysaccharide of the present invention is one wherein the polysaccharide is a pharmaceutically or cosmetically acceptable salt of hyaluronic acid. There is no limitation on the type of hyaluronic acid salt that can be used, as long as they are pharmaceutically or cosmetically acceptable when used for therapeutic purposes. Hyaluronic acid and a salt thereof may differ in some physical properties but they are equivalent for the purposes of the present invention and the skin-friendly properties of hyaluronic acid are extensible to a pharmaceutically or cosmetically acceptable salt, in particular to its sodium salt (or sodium hyaluronate) and potassium salt (potassium hyaluronate). The term "pharmaceutically acceptable salt" refers to the salt appropriate for use in pharmaceutical technology for the preparation of compositions for medical use and, the term "cosmetically acceptable salt" or "dermatologically acceptable salt" used interchangeably in this document refers to the salt appropriate for use in human skin contact without toxicity, incompatibility, instability, inappropriate allergic response, among others. In particular, the term "pharmaceutical or cosmetically acceptable salt" covers commonly used salts such as e.g. alkaline metal salts. The preparation of pharmaceutically acceptable salts of hyaluronic acid can be carried out by methods known in the technique. Non-limiting examples of pharmaceutical or cosmetically acceptable salts of hyaluronic acid appropriate for the present invention include inorganic salts such as sodium hyaluronate, magnesium hyaluronate, potassium hyaluronate, zinc hyaluronate and cobalt hyaluronate, as well as organic salts such as tetrabutylammonium hyaluronate. In an embodiment, the pharmaceutically or cosmetically acceptable salt of hyaluronic acid is a salt of a selected alkaline metal of sodium salt (CAS No: 9067-32-7) or potassium salt (CAS No: 31799-91-4).

In an embodiment, the crosslinked polysaccharide of the present invention is one wherein the polysaccharide is a high molecular weight hyaluronic acid. The term "High molecular weight hyaluronic acid" refers to a hyaluronic acid with a molecular weight of 300 kDa or more. In an embodiment, the crosslinked polysaccharide of the present invention is one wherein the polysaccharide is a high molecular weight hyaluronic acid having a molecular weight from 300 kDa to 5000 kDa; particularly from 500 kDa to 2000 kDa. In a particular embodiment, the crosslinked polysaccharide of the present invention is one wherein the polysaccharide is a high molecular weight hyaluronic acid having a molecular weight from 1000 kDa to 2000 kDa.

In an embodiment, the crosslinked polysaccharide of the present invention is the crosslinked polysaccharide (III)-4 having:

a crosslinking degree of 0.2688% a enzymatic degradation rate of 2.8 mmole/h; and an oxidative degradation rate of 3.3 mmole/h;

wherein:

the polysaccharide is hyaluronic acid, and the hyperbranched PPE used as starting material is the compound (I)-22.

In an embodiment, the crosslinked polysaccharide of the present invention is the crosslinked polysaccharide (III)-9 having:

a crosslinking degree of 0.1127% an enzymatic degradation rate of 3.6 mmole/h; and an oxidative degradation rate of 4.3 mmole/h;

wherein:

the polysaccharide is hyaluronic acid, and the hyperbranched PPE used as starting material is the compound (I)-16.

In an embodiment, the crosslinked polysaccharide of the present invention is the crosslinked polysaccharide (III)-8 having:

a crosslinking degree of 0.1358% an enzymatic degradation rate of 3.5 mmole/h; and an oxidative degradation rate of 4.3 mmole/h;

wherein:

the polysaccharide is hyaluronic acid, and the hyperbranched PPE used as starting material is the compound (I)-22.

In an embodiment, the crosslinked polysaccharide of the present invention is the crosslinked polysaccharide (III)-5 having:

a crosslinking degree of 0.1877% an enzymatic degradation rate of 0.8 mmole/h; and an oxidative degradation rate of 3.0 mmole/h;

wherein:

the polysaccharide is hyaluronic acid, and the hyperbranched PPE used as starting material is the compound (I)-23.

In an embodiment, the crosslinked polysaccharide of the present invention is the crosslinked polysaccharide (III)-6 having:

a crosslinking degree of 0.1528% an enzymatic degradation rate of 2.7 mmole/h; and an oxidative degradation rate of 3.4 mmole/h;

wherein:

the polysaccharide is hyaluronic acid, and the hyperbranched PPE used as starting material is the compound (I)-16.

In an embodiment, the crosslinked polysaccharide of the present invention is the crosslinked polysaccharide (III)-14 having:

a crosslinking degree of 0.3911% an enzymatic degradation rate of 2.8 mmole/h; and an oxidative degradation rate of 2.6 mmole/h;

wherein:

the polysaccharide is hyaluronic acid, and the hyperbranched PPE used as starting material is the compound (I)-22.

In an embodiment, the crosslinked polysaccharide of the present invention is the crosslinked polysaccharide (III)-15 having:

a crosslinking degree of 0.3049% an enzymatic degradation rate of 1.1 mmole/h; and an oxidative degradation rate of 2.3 mmole/h;

wherein:

the polysaccharide is hyaluronic acid, and the hyperbranched PPE used as starting material is the compound (I)-23.

In an embodiment, the crosslinked polysaccharide of the present invention is the crosslinked polysaccharide (III)-16 having:

a crosslinking degree of 0.2723% an enzymatic degradation rate of 2.9 mmole/h; and an oxidative degradation rate of 2.6 mmole/h;

wherein:

the polysaccharide is hyaluronic acid, and the hyperbranched PPE used as starting material is the compound (I)-16.

In an embodiment, the crosslinked polysaccharide of the present invention is one wherein the polysaccharide is starch or a derivative thereof. For the purpose of the present invention the term "Starch" refers to is a polysaccharide carbohydrate consisting of a large number of glucose units joined by glycosidic bonds. Starch is produced by all green plants as an energy store and is a major food source for humans. For the purpose of the invention, the terms "starch derivative" or "modified starch" have the same meaning and are used interchangeable. They refer to starch that has been reacted to modify its properties. Examples of starch derivative are hydroxyalkyl, carboxyalkylated, alkylcarbonylated, phosphated, sulfated, graft derivatized and alkylated starchs. In an embodiment, the starch derivative is selected from the group consisting of hydroxypropyl starch, sodium starch glycolate and carboxymethyl starch.

In an embodiment, the crosslinked polysaccharide of the present invention is one wherein the polysaccharide is cellulose or a derivative thereof. For the purpose of the present invention the term "cellulose" to a polysaccharide having a backbone formed by D-glucopyranose units connected by β-1,4-glycosidic bonding. The terms "modified cellulose" or "cellulose derivative" have the same meaning and are used interchangeable. They refer to any compound that has a cellulose backbone, i.e. a structure of D-glucopyranose units connected by β-1,4-glycosidic bonding, which has been chemically modified by the introduction of pendant moieties not comprised in pure cellulose. Non-limiting examples of cellulose derivative include methylcellulose, hydroxyethyl cellulose, hydroxyethylmethyl cellulose, hydroxypropyl cellulose, L-hydroxypropyl cellulose (low substituted), hydroxypropyl methyl cellulose (HPMC), sodium carboxymethyl cellulose or carboxymethyl hydroxyethyl cellulose.

All the above-mentioned embodiments disclosed for the crosslinked polysaccharide of the present invention, also apply individually for each one of the specifically above-listed polysaccharide, that are hyaluronic acid, starch and a derivative thereof, glycogen, cellulose and a derivative thereof, pectin, lignin, inulin, guar gum, xanthan gum, alginic acids (alginates), heparin, chondroitin sulphate, dermatan sulphate, glucuronan, glucomannan, galactomannan and carrageenans.

It is also an aspect of the invention a process for the preparation of a crosslinked polysaccharide of formula (III) or alternatively of formula (IV) of the present invention.

In an embodiment, the process for the preparation of a crosslinked polysaccharide (III) of the present invention comprises crosslinking the polysaccharide with a compound of formula (I) as defined in the first aspect of the invention.

In an embodiment, the process for the preparation of a crosslinked polysaccharide of formula (III) of the present invention comprises crosslinking the polysaccharide with a compound of formula (I) as defined in the first aspect of the invention; wherein the compound of formula (I) is obtainable by the process which comprises performing steps a) and b) as defined above. Thus, the process for the preparation of the crosslinked polysaccharide of formula (III) the present invention comprises crosslinking the polysaccharide with a compound of formula (I), wherein the compound of formula (I) is obtained by a process comprising: a) providing an alkaline solution containing 1,3-glycerol diglycidyl ether; and b) maintaining the solution obtained in step a) at a temperature from 10 to 80° C. for a period of time from 1 min to 30 days.

In an embodiment, the process for the preparation of a crosslinked polysaccharide (III) of the present invention comprises crosslinking the polysaccharide with a compound of formula (II) as defined in the first aspect of the invention.

In an embodiment, the process for the preparation of a crosslinked polysaccharide of formula (IV) of the present invention comprises crosslinking the polysaccharide with a compound of formula (II); wherein the compound of formula (II) is obtainable by the process which comprises performing steps c) and d) as defined above. Thus, the process for the preparation of the crosslinked polysaccharide of the present invention comprises crosslinking the polysaccharide with a compound of formula (II), wherein the compound of formula (II) is obtained by a process comprising: c) providing an alkaline solution containing 1,2-glycerol diglycidyl ether; and d) maintaining the solution obtained in step c) at a temperature from 10 to 80° C. for a period of time from 1 min to 30 days.

All the embodiments disclosed above for the polysaccharide, the compound of formula (I), the compound of formula (II) and the crosslinking polysaccharide; as well as the reaction conditions of steps a)-d) of the process for the preparation of the crosslinked polysaccharide of the present invention, also apply for the crosslinked polysaccharide obtainable by this process.

In an embodiment, the process for the preparation of the crosslinked polysaccharide of formula (III) which comprises:

e) crosslinking the polysaccharide with a compound of formula (I) as defined in the first aspect of the invention; and optionally g) isolating the crosslinked polysaccharide of formula (III) of the invention.

In an embodiment, step e) of the process for the preparation of the crosslinked polysaccharide of formula (III) comprises:

e1) providing an alkaline solution from 5 to 15 percent by weight of polysaccharide;

e2) providing an alkaline solution comprising the compound of formula (I); and e3) mixing the solution obtained in step e1) and the solution obtained in step e2) to obtain an alkaline solution comprising the polysaccharide and the compound of formula (I); and e4) maintaining the alkaline solution obtained in step e3) at a temperature comprised from 20° c to 50° C. for a period from 1 to 48 hours.

In an embodiment, the process for the preparation of the crosslinked polysaccharide of formula (IV) which comprises:

f) crosslinking the polysaccharide with a compound of formula (II) as defined in the first aspect of the invention, and optionally g) isolating the crosslinked polysaccharide of formula (IV) of the invention.

In an embodiment, step f) of the process for the preparation of the crosslinked polysaccharide of formula (IV) comprises:

f1) providing an alkaline solution from 5 to 15 percent by weight of polysaccharide;

f2) providing an alkaline solution comprising the compound of formula (II); and f3) mixing the solution obtained in step f1) and the solution obtained in step f2) to obtain an alkaline solution comprising the polysaccharide and the compound of formula (II); and f4) maintaining the alkaline solution obtained in step f3) at a temperature comprised from 20° c to 50° C. for a period from 1 to 48 hours.

In an embodiment, the alkaline solution of step e3) or alternatively step f3) comprises a concentration of the polysaccharide from 5 to 15% by weight.

In an embodiment, the alkaline solution obtained in step e3) or alternatively step f3) comprises from 0.25 to 0.75M of alkaline base; particularly from 0.40 to 0.60M of alkaline base.

In an embodiment, the alkaline solution obtained in step e3) or alternatively step f3) comprises from 5 to 15% by weight of polysaccharide; particularly from 8 to 10% by weight of polysaccharide.

In an embodiment, the alkaline solution obtained in step e3) or alternatively step f3) comprises from 0.2 to 1% by weight of compound of formula (I) or alternatively of the compound of formula (II); particularly from 0.3 to 0.5% by weight.

In an embodiment, the alkaline solution obtained in step e3) or alternatively step f3) comprises a weight ratio between the compound of formula (I) and the polysaccharide or alternatively a weight ratio between the compound of formula (II) and the polysaccharide from 2 to 40% w/w; particularly from 2 to 12.5% w/w expressed as weight ratio of PPE to dry polysaccharide. The term "weight ratio" refers to the relation of weights of two ingredients needed to enlarge the stability and increase the bioavailability of the crosslinked polysaccharide of the present invention after its application. Particularly, the relation of polysaccharide and hyperbranched PPE of the present invention needed to decrease the enzymatic/oxidative degradation rate and reducing the crosslinking degree.

In an embodiment, the alkaline solution obtained in step e4) or alternatively step f4) comprises from 1 to 50 mg/mL of polysaccharide.

The isolation steps g) can be performed according to the methods well known for a skilled person disclosed in the state of the art for the isolation of chemical compounds. In an embodiment, the isolation step may include removing them by one or more of the following operations: evaporation, lyophilisation, filtration, decantation and centrifugation, or other suitable techniques as known to a person skilled in the art. In an embodiment, the isolation steps g) comprises adjusting the pH of the alkaline solution obtained in steps e3) or alternatively f3) to 6.5 to 7.4. The adjustment of the pH can be performed by the addition of an acid, such as for example HCl, $H_3PO_3$ or a mixture thereof. The determination of the pH can be performed by any method known in the state of the art. In the case of the present application the pH is determinate by the direct reading of pH value using a pHmeter with its electrode immersed in the hydrogel.

Another aspect of the invention relates to a composition comprising:

one or more of the crosslinked polysaccharides of the present invention, and one or more appropriate excipients or carriers. The appropriate crosslinked polysaccharide as well as the appropriate excipients and/or carriers, and their amounts, can readily be determined by those skilled in the art according to the field and the type of formulation being prepared.

In an embodiment, the composition is a pharmaceutical composition which comprises a therapeutically effective amount of one or more pharmaceutically acceptable crosslinked polysaccharide, and one or more pharmaceutically acceptable excipients or carriers.

The term "pharmaceutical composition" refers to a composition suitable for use in the pharmaceutical technology with medical use. The term "therapeutically effective amount of a pharmaceutically acceptable crosslinked polysaccharide" as used herein, refers to the amount of a crosslinked polysaccharide of the present invention that, when administered, is sufficient to prevent development of, or alleviate to some extent, one or more of the symptoms of the disease which is addressed. The dose of the pharmaceutically acceptable crosslinked polysaccharide administered according to this invention will of course be determined by the particular circumstances surrounding the case, including the compound administered, the route of administration, the particular condition being treated, and the similar considerations. For the purpose of the invention the term "pharmaceutically acceptable crosslinked polysaccharide" refers to the active or central ingredient in the composition which causes the direct (therapeutically) effect on the diagnosis, prevention, treatment, cure or alleviation of a disease or condition.

The pharmaceutical compositions of the present invention comprise one or more pharmaceutically acceptable excipients or carriers. The term "pharmaceutically acceptable excipients or carriers" refers to that excipients or carriers suitable for use in the pharmaceutical technology for preparing compositions with medical use. In an embodiment, the compositions of the present invention comprise one or more pharmaceutically acceptable excipients and/or carriers selected from the group consisting of diluent, binder, glidant, disintegrant, lubricant and mixtures thereof. Additionally, the pharmaceutical compositions of the present invention may contain other ingredients, such as fragrances, colorants, and other components known in the state of the art.

In an embodiment, the pharmaceutical composition comprises one or more pharmaceutically acceptable crosslinked polysaccharide selected from the group consisting of hyaluronic acid, starch and a derivative thereof, glycogen, cellulose and a derivative thereof, pectin, lignin, inulin, guar gum, xanthan gum, alginic acids (alginates), heparin, chondroitin sulphate, dermatan sulphate, glucuronan, glucomannan, galactomannan and carrageenans.

In an embodiment, the composition is a cosmetic composition which comprises a cosmetically effective amount of one or more cosmetically acceptable crosslinked polysaccharide, and one or more cosmetically acceptable excipients or carriers.

The cosmetic composition of the present invention is designed to apply to the body the appropriate amount ("cosmetically effective amount") to improve its appearance or to beautify, preserve, condition, cleanse, color or protect the skin, nails or hair (cf. Academic press Dictionary of Science and Technology, 1992, pp. 531; A terminological Dictionary of the Pharmaceutical Sciences. 2007, pp.190). Therefore, the above cosmetic compositions are adjectivally used for a non-medical application.

The term "cosmetically acceptable" or "dermatological acceptable" which is herein used interchangeably refers to that excipients or carriers suitable for use in contact with human skin without undue toxicity, incompatibility, instability, allergic response, among others.

In an embodiment, the pharmaceutical or cosmetic composition of the present invention is a topical composition, which can be formulated in several forms that include, but are not limited to, solutions, aerosols and non-aerosol sprays, shaving creams, powders, mousses, lotions, gels, sticks, ointments, pastes, creams, shampoos, shower gel, body washes or face washes.

In an embodiment, the pharmaceutical or cosmetic composition is an oral composition. For example, the solid composition is a tablet, granule and capsule.

In an embodiment, the pharmaceutical or cosmetic composition is an injectable composition. In an embodiment, the pharmaceutical or cosmetic composition is an injectable composition selected from the group consisting of intramuscular, subcutaneous, or intravenous application. In an embodiment, the pharmaceutical or cosmetic compositions of the present invention are in form of parenteral compositions suitable for their injection, infusion, or implantation into the body. The parenteral compositions defined above should be sterile, and pyrogen-free, and they can be in form of liquid such as solutions, emulsions, or suspensions, or in solid form packaged in either single-dose or multidose containers suitably diluted before use. Parenteral compositions can comprise appropriate excipients or carriers for parenteral administration that can be pharmaceutical or cosmetic excipients, including, but not limited to, solvents, suspending agents, buffering agents, substances to make the preparation isotonic with blood, stabilizers, or antimicrobial preservatives. The addition of excipients should be kept to a minimum. When excipients are used, they should not adversely affect the stability, bioavailability, safety, or efficacy of the polymers and/or the active agents, or cause toxicity or undue local irritation. There should not be any incompatibility between any of the components of the dosage form.

The topical compositions defined above comprise appropriate excipients or carriers for topical administration that can be pharmaceutical or cosmetic excipients, including, but not limited to, repairing cutaneous barrier function agent, a hydrating agent, an emollient, an emulsifier, a thickener, a humectant, a pH-regulating agent, an antioxidant, a preservative agent, a vehicle, or their mixtures. The excipients or carriers used have affinity for the skin, are well tolerated, stable, and are used in an amount adequate to provide the desired consistency, and ease application. Additionally, the compositions of the present invention may contain other ingredients, such as fragrances, colorants, and other components known in the state of the art for use in topical formulations. The topical compositions of the invention can be formulated in several forms that include, but are not limited to, solutions, aerosols and non-aerosol sprays, creams, powders, mousses, lotions, gels, sticks, ointments, pastes, and emulsions.

In an embodiment, the cosmetic composition comprises one or more pharmaceutically acceptable crosslinked polysaccharide selected from the group consisting of hyaluronic acid, starch and a derivative thereof, glycogen, cellulose and a derivative thereof, pectin, lignin, inulin, guar gum, xanthan gum, alginic acids (alginates), heparin, chondroitin sulphate, dermatan sulphate, glucuronan, glucomannan, galactomannan and carrageenans.

In an embodiment, the composition is an edible composition which comprises one or more edible acceptable crosslinked polysaccharide, and one or more edible acceptable excipients or carriers.

The term "edible" refers to compositions, crosslinked polysaccharides, excipients and carriers that may be consumed by human being or animals without significant deleterious health consequences.

The term "edible acceptable excipients or carriers" refers to excipients or carriers which are substantially neutral from a flavour point of view, insofar as it does not significantly alter the organoleptic properties. Further, they are suitable for use in the preparation of compositions which can be consumed by humans without significant deleterious health consequences.

In an embodiment, the edible composition comprises one or more edible acceptable crosslinked polysaccharide selected from the group consisting of hyaluronic acid, starch and a derivative thereof, glycogen, cellulose and a derivative thereof, pectin, lignin, inulin, guar gum, xanthan gum, alginic acids (alginates), heparin, chondroitin sulphate, dermatan sulphate, glucuronan, glucomannan and carrageenans.

The edible compositions of the invention can be formulated in several forms that include, but are not limited to, solid or liquid forms. Additionally, the edible compositions of the present invention may contain other ingredients, such as colorants and light resistance agents, and other components known in the state of the art for use in edible compositions.

In an embodiment, the edible composition is a human being food or an animal food (feed).

In an embodiment, the composition is an agricultural composition which comprises a biologically effective amount of one or more agricultural acceptable crosslinked polysaccharide, and one or more agricultural acceptable excipients or carriers.

The term "agricultural" refers to compositions, crosslinked polysaccharides, excipients and carriers that may be apply to the basal and/or foliar parts of plants to treat them without significant deleterious health consequences.

In an embodiment, the agricultural composition is selected from the group consisting of fertilizers, macronutrients, micronutrients, pesticides, plant growth regulators, plant hormones and Nod factor.

As used herein the term "biologically effective amount" refers to that amount of the crosslinked polysaccharide of the present invention required to produce a desired effect on a plant, on an insect, or a plant pest. Effective amounts of the substance will depend on several factors, including the treatment method, plant species, pest species, propagating material type and environmental conditions. For example, a biologically effective amount of an insecticide would be the amount of the insecticide that protects a plant from damage. This does not mean that protected plant suffers no damage from the pest, but that the damage is at such a level as to allow the plant to give an acceptable yield of a crop.

The agricultural composition can be formulated in a form selected from a group comprising wettable powders, dusting powders, water dispersible granules, suspension concentrates, emulsifiable concentrates, tablets, pellets, liquids and oil suspensions.

In an embodiment, the agricultural composition comprises one or more agricultural acceptable crosslinked polysaccharide selected from the group consisting of hyaluronic acid, starch and a derivative thereof, glycogen, cellulose and a derivative thereof, pectin, lignin, inulin, guar gum, xanthan gum, alginic acids (alginates), heparin, chondroitin sulphate, dermatan sulphate, glucuronan, glucomannan, galactomannan and carrageenans.

It is also a part of the invention the use of the crosslinked polysaccharides of the present invention. The appropriate crosslinked polysaccharide as well as the appropriate excipients and/or carriers, and their amounts, can readily be determined by those skilled in the art according to the field and the type of formulation being prepared.

The pharmaceutical crosslinked polysaccharides of the invention and the pharmaceutical compositions containing them can be used in the pharmaceutical field. Therefore, it is also a part of the invention the pharmaceutical crosslinked polysaccharides of the present invention or alternatively a pharmaceutical composition containing them of the present invention for use in therapy. In an embodiment, a crosslinked HA of the present invention or a composition containing it for use in therapy.

This aspect could be also formulated as the use of the pharmaceutical crosslinked polysaccharides for the preparation of a medicament. It also relates to a method for the treatment of a mammal suffering from a disease, wherein the method comprises administering to said mammal a pharmaceutical composition comprising a therapeutically effective amount of the pharmaceutical crosslinked polysaccharides of the present invention as defined above. In an embodiment, the pharmaceutical composition of the present invention as defined above is one wherein the pharmaceutical crosslinked polysaccharide is a crosslinked polysaccharide for use in the treatment of soft tissue augmentation. This aspect could be also formulated as the use of the pharmaceutical composition of the invention which comprises a crosslinked HA as defined above for the preparation of a medicament for the treatment of wounds. It also relates to a method for the treatment of a mammal suffering from osteoarthritis. wherein the method comprises administering to said mammal the pharmaceutical composition of the present invention which comprises the crosslinked HA as defined above.

All the embodiments as defined above for the pharmaceutical crosslinked polysaccharides and the pharmaceutical compositions of the present invention also apply for their use in therapy.

The cosmetic crosslinked polysaccharides of the invention and the cosmetic compositions containing them can be used in the cosmetic field. Therefore, it is also a part of the invention the use of cosmetic crosslinked polysaccharides and the cosmetic compositions of the present invention as a skin care agent, where the skin care comprises ameliorating at least one of the following symptoms: roughness, flakiness, dehydration, tightness, chapping, and lack of elasticity.

In an embodiment, the cosmetic crosslinked polysaccharides of the invention and the cosmetic compositions containing them is a moisturizing agent. In an embodiment, the cosmetic crosslinked polysaccharides of the invention and the cosmetic compositions containing them is a skin care agent. In an embodiment, the cosmetic crosslinked polysaccharides of the invention and the cosmetic compositions containing them is a soothing agent. The soothing agent is suitable for allaying, calming, composing, lulling, quieting, settling, stilling, or tranquilizing the skin. In an embodiment, the cosmetic crosslinked polysaccharides of the invention and the cosmetic compositions containing them is a skin barrier recovery agent.

In an embodiment, the cosmetic crosslinked polysaccharides of the invention and the cosmetic compositions containing them is a dermal filler, particularly wherein the polysaccharide is HA.

The edible crosslinked polysaccharides of the invention and the edible compositions containing them can be used in the food field. In an embodiment, the edible crosslinked polysaccharides of the invention and the edible compositions containing them is a food additive. In an embodiment, the edible crosslinked polysaccharides of the invention and the edible compositions containing them is texture modifying agent such as for example gum, thickener, extender, emulsion stabilizer and binder.

In an embodiment, use of an edible crosslinked polysaccharide of the invention and the edible compositions containing them as a food additive; particularly a texture modifying agent, wherein the polysaccharide is HA, starch and derivative thereof, cellulose and derivative thereof, pectin, lignin, inulin, guar gum, xanthan gum, alginic acids (alginates), heparin, chondroitin sulphate, dermatan sulphate, glucuronan, glucomannan and carrageenans.

It is also a part of the invention, the use of a crosslinked polysaccharide of the invention as a carrier, which is as a delivery system of pharmaceutical active ingredients, diagnostic agents, cosmetic compounds, peptides, proteins, antibodies, vaccines and genes.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim and shall not be construed as limiting the scope of the claim. Furthermore, the present invention covers all possible combinations of embodiments described herein.

EXAMPLES

List of Abbreviations

HA: hyaluronic acid
GAG: glycosaminoglycan
C.D.: cross-linking degree
NaCMC: Sodium carboxymethylcellulose
HES: hydroxyethyl starch
GlcA: D-glucuronic acid
GlcNAc: N-acetyl-D-glucosamine
ECM: extracellular matrix
ROS: reacting oxygen species
HYAL: hyaluronidase enzyme
IA: inflammatory arthritis
EDC: carbodiimide
DVS: divinyl sulfone
BDDE: 1,4-butane diol diglycidyl ether
PEGDE: poly (ethylene glycol) diglycidyl ether
GDE: 1,3-glycerol diglycidyl ether
PPE: polyglycerol diglycidyl ether
FDA: Food and Drug Administration
EEW: Epoxy Equivalent Weight
GPC: gel permeation chromatography
SEC: size exclusion chromatography
SANS: Small Angle Neutron Scattering
1H NMR: proton nuclear magnetic resonance
PBS: phosphate buffer solution
IPN: interpenetrating networks
MMPs: metalloproteinases
Mw: weight-average molecular weight
Mn: number-average molecular weight

Materials

Shyalt ultrapure Sodium hyaluronate (Hyaluronic acid) from Altergon Italy.
High amylose starch from Merck.
High amylopectin starch from Merck.
Sodium carboxymethyl Cellulose 0.7 MDa, 0.8-0.9 D.S. AQUALON™, BLANOSE™ and BONDWELL™.
Butane Diol Diglycidyl Ether (BDDE), MW=202 Da from Merck.
Poly Ethylene Glycol Diglycidyl Ether (PEGDE), MW=526 Da from Merck.
1,3-Bis(2-oxiranylmethoxy)-2-propanol which is also known with the following names, tradenames, synonyms and abbreviations: 1,3-Bis(oxiran-2-ylmethoxy)propan-2-ol; 2-Propanol, 1,3-bis(oxiranylmethoxy); Glycerol 1,3-diglycidyl ether; Denacol EX-313, MW=204 Da, EEW=141 g/eq from Nagase Chemtex; 1,3-Glycerol Diglycidyl Ether, MW=204 Da from Merck; and 1,3-GDE has the following structure:

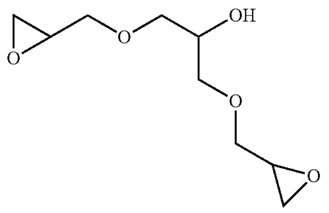 [SMILES: OC(COCC1CO1)COCC1CO1]

2,3-Bis(2-oxiranylmethoxy)-1-propanol which is also known with the following names, tradenames, synonyms and abbreviations: 2,3-bis(oxiran-2-ylmethoxy)propan-1-ol, 1-Propanol, 1,2-bis(oxiranylmethoxy); Glycerol 1,2-diglycidyl ether; 1,2-Glycerol diglycidyl ether, MW=204 Da from Merck; and 1,2-GDE has the following structure:

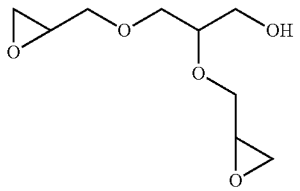 [SMILES: OCC(COCC1CO1)OCC1CO1]

Mixtures of 1,3-GDE and 1,2-GDE are also commercially available with the following trademark names: Denacol EX-314, MW=260 Da, EEW=144 g/eq from Nagase Chemtex;
Sodium Hydroxide pellets (NaOH) from Merck;
Hydrochloric Acid 37% (HCl) from Merck;
Sodium Chloride powder (NaCl) from Merck;
Potassium Chloride powder (KCl) from Merck;
Phosphoric acid 85% ($H_3PO_4$) from Merck;
Phosphate buffer saline (PBS) pellets from Merck;
Distilled water ($H_2O$) from Merck.

Methods

Method for the measurement of the average Mw, Mn and Mw/Mn was evaluated by GPC/SEC analysis using a chromatographic instrument equipped with light scattering detector.

Method for the measurement of the EEW was evaluated by ultrasonic assisted titration.

Method for the measuring pH was calculated by direct reading of pHmeter equipped with an electrode directly immersed in the hydrogel.

1. Hyperbranched Polyglycerol Polyglycidyl Ether

1.1. Using 1,3-GDE as Stating Material

The below-mentioned preparation processes can be also performed by using the Denacol® EX-313 commercially available from Nagase as a source of 1,3-GDE. Nevertheless, these processes can be also performed by using the 1,3-glycerol diglycidyl ether commercially available from Merck or with the trademark Denacol® EX-314 which is a mixture containing 1,3-DGE instead of Denacol® EX-313.

1.1.1. Process 1

Sodium hydroxide pellets (NaOH) were dissolved in water to form an alkaline solution containing a 4 percent of NaOH (1M) by weight based on total solution weight (Solution A).

1,3-GDE (Denacol® EX-313) was dissolved at room temperature in a portion of solution A to form an alkaline solution containing from 1 to 50 percent of 1,3-GDE by weight based on total solution weight (Solution C1). Solution C1 was then left to react at controlled temperature in the range between 50 and 80° C. for a period comprised from 1 to 500 minutes during which self-polymerization of 1,3-GDE take place giving Polyglycerol Polyglycidyl Ethers of the present invention (Solution C3 disclosed in Table 1 (Examples 1-13).

1.1.2. Process 2

Sodium hydroxide pellets (NaOH) were dissolved in water to form an alkaline solution containing a 4 percent of NaOH (1M) by weight based on total solution weight (Solution A).

1,3-GDE (Denacol® EX-313) was dissolved at room temperature in a portion of solution A to form an alkaline solution containing from 1 to 50 percent of 1,3-GDE by weight based on total solution weight (Solution C1). Solution C1 was then left to react at controlled temperature in the range between 10 and 40° C. for a period comprised from 1 to 30 days during which self-polymerization of 1,3-GDE take place giving Polyglycerol Polyglycidyl Ether of the present invention (Solution C2) disclosed in Table 1 (Examples 14-31).

1.1.3. Characterization of the PPE of the Present Invention

The molecular weight and the epoxy content of the obtained PPE, measured as Epoxy Equivalent Weight expressed as percentage of EEW of starting GDE, of the PPE obtained following the processes 1 and 2 were analytically monitored over time using respectively GPC instrument equipped with light scattering detector and quantitative titration with HCl as previously described. Before each analysis, the self-polymerization reaction of GDE was stopped by adding 1M hydrochloric acid solution and PBS to neutralize alkaline catalyst and restore the pH of the Polyglycerol Polyglycidyl Ether solution to 7.0.

Values of the average molecular weight (MW) and EEW of the obtained polyglycerol polyglycidyl ether (PPE) of the present invention for each combination of temperature and time are reported in table 1.

TABLE 1

| Ex. | [1,3-GDE] (% w/w) | [NaOH] (mol/L) | Temp. (° C.) | Time (min) | PPE average MW (g/mol) | PPE EEW (g/eq) | Epoxides (meq/g) |
|---|---|---|---|---|---|---|---|
| 1 | 1.00 | 1.00 | 50 | 180 | 2370 | 792 | 1.263 |
| 2 | 10.00 | 1.00 | 50 | 15 | 900 | 463 | 2.159 |
| 3 | 10.00 | 1.00 | 50 | 30 | 1460 | 1460 | 0.685 |
| 4 | 10.00 | 1.00 | 50 | 60 | 2980 | 2976 | 0.336 |
| 5 | 20.00 | 1.00 | 50 | 30 | 2970 | 2620 | 0.342 |
| 6 | 50.00 | 1.00 | 50 | 30 | 2980 | 1761 | 0.568 |
| 7 | 10.00 | 1.00 | 60 | 15 | 1100 | 1175 | 0.851 |
| 8 | 10.00 | 1.00 | 60 | 30 | 4200 | 4717 | 0.212 |
| 9 | 20.00 | 1.00 | 60 | 15 | 2050 | 2243 | 1.089 |
| 10 | 20.00 | 1.00 | 70 | 15 | 750 | 524 | 1.908 |
| 11 | 50.00 | 1.00 | 70 | 30 | 1260 | 951 | 1.051 |
| 12 | 50.00 | 1.00 | 70 | 60 | 1820 | 1628 | 0.614 |
| 13 | 50.00 | 1.00 | 80 | 10 | 930 | 1046 | 0.956 |
| 14 | 10.00 | 1.00 | 20 | 1 | 940 | 234 | 4.268 |
| 15 | 10.00 | 1.00 | 20 | 2 | 2540 | 423 | 2.365 |
| 16 | 10.00 | 1.00 | 20 | 3 | 3530 | 589 | 1.699 |
| 17 | 10.00 | 1.00 | 20 | 4 | 5820 | 831 | 1.203 |
| 18 | 10.00 | 1.00 | 20 | 5 | 7790 | 1558 | 0.642 |
| 19 | 10.00 | 1.00 | 20 | 6 | 9000 | 9005 | 0.111 |
| 20 | 20.00 | 1.00 | 20 | 4 | 7990 | 7580 | 0.132 |
| 21 | 50.00 | 1.00 | 20 | 2.5 | 4200 | 585 | 1.708 |
| 22 | 10.00 | 1.00 | 30 | 0.5 | 910 | 229 | 4.375 |
| 23 | 10.00 | 1.00 | 30 | 1 | 2400 | 404 | 2.501 |
| 24 | 10.00 | 1.00 | 30 | 2 | 6220 | 889 | 1.125 |
| 25 | 10.00 | 1.00 | 30 | 3 | 15000 | 8028 | 0.127 |
| 26 | 20.00 | 1.00 | 30 | 0.5 | 2200 | 365 | 2.741 |
| 27 | 50.00 | 1.00 | 30 | 2 | 13000 | 7463 | 0.134 |
| 28 | 10.00 | 1.00 | 40 | 0.25 | 990 | 247 | 4.051 |
| 29 | 10.00 | 1.00 | 40 | 0.5 | 1700 | 424 | 2.356 |
| 30 | 10.00 | 1.00 | 40 | 1 | 2700 | 902 | 1.109 |
| 31 | 10.00 | 1.00 | 40 | 1.5 | 10000 | 10152 | 0.099 |

2. Crosslinked Polysaccharides 2.1. Cross-Linked Hyaluronic Acid 2.1.1. PPE Cross-Linked Hyaluronic Acid of the Present Invention 2.1.1.1. Preparation Process The PPE crosslinked hyaluronic acid of Examples 1-13 (see Table 2) were prepared following the processes as defined below. The PPE crosslinked hyaluronic acid of Examples 14-16 (see Table 2) were prepared following the same processes as for Examples 1-13, but using a crosslinker concentration about 2.5-fold than in Examples 1-13, which is a concentration of 1.00.

Process 1

A. Preparation of the Polyglycerol Polyglycidyl Ether of Ex. 1-13 Following the Process Disclosed in Section 1.1.2. Above.

B. Preparation of Crosslinked Polysaccharides

Alternative B1

Hyaluronic acid (HA) dry powder was gently dissolved at room temperature (25° C.) in a portion of solution A (or directly added to solution C3) to form an alkaline solution containing from 5 to 15 percent of hydrated HA by weight based on total solution weight (Solution B).

The solution C3 is then added to the solution B to provide an alkaline solution with a hydroxide concentration in the final solution in the range from 0.25 and 0.75M and with a ratio of HA and PPE from 2 to 12.5% w/w (expressed as weight ratio of PPE to dry polysaccharide).

Alternative B2

The solution C3 is then added to the solution B to provide an alkaline solution with a hydroxide concentration in the final solution in the range from 0.25 and 0.75M, a concentration of HA in the final solution in the range from 8 to 10% by weight in relation to the total weight, and a concentration of PPE in the final solution in the range from 0.2 to 1% by weight in relation to the total weight. The ratio expressed as weight ratio of PPE to dry polysaccharide is from 2 to 40% w/w expressed as weight ratio of PPE to dry polysaccharide.

C. Reaction and Isolation of the Crosslinked Polysaccharide

The resulting alkaline solution consisting of HA, PPE and NaOH is then thoroughly mixed at room temperature. The homogenous solution was then left to react at controlled temperature in the range between 20 and 50° C. for a period comprised from 1 to 48 hours.

The PPE cross-linked hyaluronic acid (hydrogel) was then washed with acidic water solution (1M hydrochloric acid and PBS) from 48 to 120 hours to remove unreacted materials and by-products, to neutralize alkaline catalyst and restore the pH of the PPE cross-linked hyaluronic acid (hydrogel) to 6.5-7.4 by ion exchange and to reach the desired final concentration of HA in the PPE cross-linked hyaluronic acid hydrogel from 1 to 50 mg/mL as shown in Table 2.

The PPE cross-linked hyaluronic acid (hydrogel) was filled into syringes and steam sterilized in autoclave following the pharmacopeia accepted procedures reported in the EN ISO 17665-1, Sterilization of health care products—Moist heat Part 1: requirements for the development, validation and routine control of a sterilization process for medical device (e.g. 15 min at 121° C.).

The PPE cross-linked hyaluronic acid (hydrogel) could be optionally dehydrated under vacuum at 30° C. or lyophilized (freeze-dried) and stored for following use or analysis.

Process 2

A. Preparation of the Polyglycerol Polyglycidyl Ether of Ex. 14-31 Following the Process Disclosed in Section 1.1.3. Above.

B. Preparation of Crosslinked Polysaccharides

Alternative B1

Hyaluronic acid (HA) was gently dissolved at room temperature (25° C.) in a portion of solution A (or directly added to solution C3) to form an alkaline solution containing from 5 to 15 percent of hydrated HA by weight based on total solution weight (Solution B). The solution C3 is then added to the solution B to provide an alkaline solution with a hydroxide concentration in the final solution in the range from 0.25 and 0.75M and with a ratio of HA and PPE from 2 to 12.5% w/w (expressed as weight ratio of PPE to dry polysaccharide).

Alternative B2

The solution C3 is then added to the solution B to provide an alkaline solution with a hydroxide concentration in the final solution in the range from 0.25 and 0.75M, a concentration of HA in the final solution in the range from 8 to 10% by weight in relation to the total weight, and a concentration of PPE in the final solution in the range from 0.2 to 1% by weight in relation to the total weight. The ratio expressed as weight ratio of PPE to dry polysaccharide is from 2 to 40% w/w (expressed as weight ratio of PPE to dry polysaccharide).

C. Reaction and Isolation of the Crosslinked Polysaccharide

The resulting alkaline solution consisting of HA, PPE and NaOH is then thoroughly mixed at room temperature. The homogenous solution was then left to react at controlled temperature in the range between 20 and 50° C. for a period comprised from 1 to 48 hours.

The PPE cross-linked hyaluronic acid (hydrogel) was then washed with acidic water solution (1M hydrochloric acid and PBS) from 48 to 120 hours to remove unreacted materials and by products, to neutralize alkaline catalyst and restore the pH of hydrogel to 6.5+7.4 by ion exchange and to reach the final concentration of HA in the PPE cross-linked hyaluronic acid (hydrogel) from 1 to 50 mg/mL as shown in Table 2.

The PPE cross-linked hyaluronic acid hydrogel) was filled into syringes and steam sterilized in autoclave following the pharmacopeia accepted procedures reported in the EN ISO 17665-1, Sterilization of health care products—Moist heat Part 1: requirements for the development, validation and routine control of a sterilization process for medical device (e.g. 15 min at 121° C.). The PPE cross-linked hyaluronic acid (hydrogel) could be optionally dehydrated under vacuum at 30° C. or lyophilized (freeze-dried) and stored for following use or analysis.

2.1.1.2. Characterization of the PPE Crosslinked Hyaluronic Acid of the Present Invention (PPE Crosslinked Hyaluronic Acid Ex. 1-16)

The mechanical properties of PPE cross-linked hyaluronic acid of the present invention obtained from the PPE of the present invention are disclosed in Table 2. The PPE cross-linked hyaluronic acid disclosed in Examples 1-13 in Table 2 has a concentration of 22.0 mg/mL of hyaluronic acid, meanwhile the Examples 14-16 has a crosslinker concentration about 2.5-fold than Examples 1-13.

TABLE 2

| | Components of the PPE cross-linked HA | | | Crosslinking reaction conditions | | Mechanical parameters of the PPE cross-linked HA | | |
|---|---|---|---|---|---|---|---|---|
| | | PPE | | | | | | |
| Ex. | Conc. HA[(a)] | Cross-linker | Conc. PPE[(b)] | Temp. (° C.) | Time (h) | G' at 0.7 Hz (Pa) | $D_N$ (nm) | C.D. (%) |
| 1 | 8.0 | 22 | 1.00 | 40 | 4 | 13.74 ± 0.73 | 41.15 ± 0.09 | 0.0830 |
| 2 | 8.0 | 23 | 1.00 | 40 | 4 | 7.77 ± 0.80 | 41.90 ± 0.10 | 0.0786 |
| 3 | 8.0 | 16 | 1.00 | 40 | 4 | 5.61 ± 0.55 | 42.19 ± 0.07 | 0.0770 |
| 4 | 10.0 | 22 | 0.40 | 30 | 7 | 266.43 ± 3.20 | 27.81 ± 0.08 | 0.2688 |
| 5 | 10.0 | 23 | 0.40 | 30 | 7 | 156.12 ± 2.90 | 31.35 ± 0.12 | 0.1877 |
| 6 | 10.0 | 16 | 0.40 | 30 | 7 | 108.70 ± 3.77 | 33.57 ± 0.20 | 0.1528 |
| 7 | 10.0 | 22 | 0.30 | 30 | 8 | 134.67 ± 4.65 | 32.28 ± 0.22 | 0.1719 |
| 8 | 10.0 | 23 | 0.30 | 30 | 8 | 85.56 ± 2.94 | 34.92 ± 0.19 | 0.1358 |
| 9 | 10.0 | 16 | 0.30 | 30 | 8 | 54.09 ± 4.07 | 37.17 ± 0.33 | 0.1127 |
| 10 | 10.0 | 22 | 0.20 | 30 | 9 | 27.20 ± 1.73 | 39.63 ± 0.18 | 0.0929 |
| 11 | 10.0 | 23 | 0.20 | 30 | 9 | 15.72 ± 2.06 | 40.91 ± 0.24 | 0.0845 |
| 12 | 10.0 | 16 | 0.20 | 30 | 9 | 11.16 ± 1.10 | 41.47 ± 0.14 | 0.0811 |
| 13 | 5.0 | 22 | 2.00 | 40 | 4 | undetectable | NA | NA |
| 14 | 10.0 | 22 | 1.00 | 30 | 7 | 432.79 ± 4.25 | 24.55 ± 0.07 | 0.3911 |
| 15 | 10.0 | 23 | 1.00 | 30 | 7 | 315.48 ± 4.09 | 26.67 ± 0.09 | 0.3049 |
| 16 | 10.0 | 16 | 1.00 | 30 | 8 | 271.19 ± 4.69 | 27.69 ± 0.12 | 0.2723 |

[(a)]concentration of HA in the PPE cross-linked HA expressed as percentage by weight in relation to the total weight.
[(b)]concentration of PPE of the present invention in the PPE cross-linked HA expressed as percentage by weight in relation to the total weight.

2.1.2. Comparative Cross-Linked Hyaluronic Acid

2.1.2.1. Comparative 1,3-GDE Cross-Linked Hyaluronic Acid (Comparative GDE-HA)

The below-mentioned comparative GDE-HA is prepared by using the Denacol® EX-313 commercially available from Nagase as a source of 1,3-GDE. Nevertheless, these processes can be also performed by using the 1,3-glycerol diglycidyl ether commercially available from Merck or with the trademark Denacol® EX-314 which is a mixture containing 1,3-DGE instead of Denacol® EX-313.

The comparative GDE crosslinked hyaluronic acid of Comparative Examples 1-5 (see Table 4) were prepared following the processes as defined below. The comparative GDE crosslinked hyaluronic acid of Comparative Example 6 (see Table 4) was prepared following the same processes as for Examples 1-5, but using a concentration of crosslinker of 1.00 and having a C.D. of 0.4037%.

Preparation Process

Sodium hydroxide pellets (NaOH) were dissolved in water to form an alkaline solution containing a 4 percent of NaOH (1M) by weight based on total solution weight (Solution A). HA was gently dissolved at room temperature (25° C.) in a portion of solution A to form an alkaline solution containing from 5 to 15 percent of hydrated HA by weight based on total solution weight (Solution B).

GDE was dissolved at room temperature in a distilled water to form a neutral solution containing from 1 to 10 percent of GDE by weight based on total solution weight (Solution C1). Optionally, GDE was dissolved at room temperature in a portion of solution A to form an alkaline solution containing from 0.2 to 2 percent of GDE by weight based on total solution weight (Solution C2). Solution C (C1/C2) is then added to the solution B to provide an alkaline solution with a hydroxide concentration in the final solution in the range from 0.25 and 0.75M and with the desired ratio of HA and GDE. The resulting alkaline solution consisting of HA, GDE and NaOH is then thoroughly mixed at room temperature.

The homogenous solution was then left to react at controlled temperature in the range between 20 and 50° C. for a period comprised from 1 to 48 hours. The comparative GDE cross-linked hyaluronic acid (hydrogel) was then washed with acidic water solution (1M hydrochloric acid and PBS) from 48 to 120 hours to remove unreacted materials and by products, to neutralize alkaline catalyst and restore the pH of hydrogel to 6.5-7.4 by ion exchange and to reach the concentration of HA in the hydrogel from 1 to 50 mg/mL as shown in Table 4 below (Comparative GDE Examples 1-5).

The hydrogel was filled into syringes and steam sterilized in autoclave following the pharmacopeia accepted procedures reported in the EN ISO 17665-1 (e.g. 15 min at 121° C.). The comparative GDE cross-linked hyaluronic acid (hydrogel) could be optionally dehydrated under vacuum at 30° C. or lyophilized (freeze-dried) and stored for following use or analysis.

Characterization of the Comparative GDE Crosslinked Hyaluronic Acid (Comp. GDE-HA. 1-6)

The mechanical properties of the comparative GDE cross-linked hyaluronic acid falling outside the scope of the present invention obtained from commercial 1,3-GDE is disclosed in Table 4 having a concentration of 22.0 mg/mL of hyaluronic acid.

TABLE 4

| Comp. | Components of the GDE cross-linked HA | | Crosslinking reaction conditions | | Mechanical parameters of the GDE cross-linked HA | | |
|---|---|---|---|---|---|---|---|
| GDE-HA Ex. | Conc. HA[(a)] | Conc. GDE[(b)] | Temp. (° C.) | Time (h) | G' at 0.7 Hz (Pa) | $D_N$ (nm) | C.D. (%) |
| 1 | 5.00 | 2.00 | 50 | 3 | undetectable | NA | NA |
| 2 | 8.00 | 1.00 | 40 | 4 | 15.30 ± 2.17 | 40.96 ± 0.26 | 0.0842 |
| 3 | 10.00 | 0.40 | 30 | 7 | 274.17 ± 9.54 | 27.62 ± 0.23 | 0.2745 |
| 4 | 10.00 | 0.30 | 30 | 8 | 141.13 ± 2.66 | 31.99 ± 0.12 | 0.1767 |
| 5 | 10.00 | 0.20 | 30 | 9 | 29.90 ± 2.36 | 39.36 ± 0.24 | 0.0949 |
| 6 | 10.00 | 1.00 | 30 | 8 | 449.89 ± 6.50 | 24.29 ± 0.10 | 0.4037 |

[(a)]concentration of HA in the GDE cross-linked HA expressed as percentage by weight in relation to the total weight.
[(b)]concentration of GDE of the present invention in the GDE cross-linked HA expressed as percentage by weight in relation to the total weight.

2.1.2.2. Comparative BDDE Cross-Linked Hyaluronic Acid (Comparative BDDE-HA)

Preparation Process

Sodium hydroxide pellets (NaOH) were dissolved in water to form an alkaline solution containing a 4 percent of NaOH (1M) by weight based on total solution weight (Solution A). Hyaluronic acid was gently dissolved at room temperature (25° C.) in a portion of solution A to form an alkaline solution containing from 5 to 15 percent of hydrated HA by weight based on total solution weight (Solution B).

BDDE was dissolved at room temperature in a distilled water to form a neutral solution containing from 0.2 to 2 percent of BDDE by weight based on total solution weight (Solution C1). Optionally, BDDE was dissolved at room temperature in a portion of solution A to form an alkaline solution containing from 1 to 10 percent of BDDE by weight based on total solution weight (Solution C2). Solution C (C1 neutral or C2 alkaline) is then added to the solution B to provide an alkaline solution with a hydroxide concentration in the final solution in the range from 0.25 and 0.75M and with the desired ratio of HA and BDDE. The resulting alkaline solution consisting of HA, BDDE and NaOH is then thoroughly mixed at room temperature. The homogenous solution was then left to react at controlled temperature in the range between 20 and 50° C. for a period comprised from 30 min to 48 hours.

The comparative BDDE cross-linked hyaluronic acid (hydrogel) was then washed with acidic water solution (1M hydrochloric acid and PBS) from 48 to 120 hours to remove unreacted materials and by products, to neutralize alkaline catalyst and restore the pH of hydrogel to 6.5-7.4 by ion exchange and to reach the concentration of HA in the comparative BDDE cross-linked hyaluronic acid (hydrogel) from 1 to 50 mg/mL as shown in Table below (Comp. BDDE-HA Ex 1-5).

The comparative BDDE cross-linked hyaluronic acid (hydrogel) was filled into syringes and steam sterilized in autoclave following the pharmacopeia accepted reported in the EN ISO 17665-1 (e.g. 15 min at 121° C.). The comparative BDDE cross-linked hyaluronic acid (hydrogel) could be optionally dehydrated under vacuum at 30° C. and stored for following use or analysis.

Characterization of the Comparative BDDE Crosslinked Hyaluronic Acid

The mechanical properties of the comparative BDDE cross-linked hyaluronic acid falling outside the scope of the present invention obtained from the commercial BDDE is disclosed in Table 5 having a concentration of 22.0 mg/mL of hyaluronic acid.

TABLE 5

| | Components of the BDDE cross-linked HA | | Crosslinking reaction conditions | | Mechanical parameters of the BDDE cross-linked HA | | |
|---|---|---|---|---|---|---|---|
| Comp. BDDE-HA Ex. | Conc. HA[(a)] | Conc. BDDE[(b)] | Temp. (° C.) | Time (h) | G' at 0.7 Hz (Pa) | $D_N$ (nm) | C.D. (%) |
| 1 | 5.00 | 2.00 | 50 | 3 | 14.60 ± 2.17 | 41.05 ± 0.26 | 0.0836 |
| 2 | 8.00 | 1.00 | 40 | 4 | 16.61 ± 0.69 | 40.81 ± 0.08 | 0.0851 |
| 3 | 10.00 | 0.40 | 30 | 7 | 270.22 ± 1.85 | 27.72 ± 0.05 | 0.2716 |
| 4 | 10.00 | 0.30 | 30 | 6 | 140.14 ± 1.76 | 32.03 ± 0.08 | 0.1760 |
| 5 | 10.00 | 0.20 | 30 | 5 | 30.36 ± 2.14 | 39.31 ± 0.22 | 0.0952 |

[(a)]concentration of HA in the GDE cross-linked HA expressed as percentage by weight in relation to the total weight.
[(b)]concentration of BDDE of the present invention in the BDDE cross-linked HA expressed as percentage by weight in relation to the total weight.

2.1.2.3. Comparative PEGDE Cross-Linked Hyaluronic Acid (Comparative PEGDE-HA)

Preparation Process

Sodium hydroxide pellets (NaOH) were dissolved in water to form an alkaline solution containing a 4 percent of NaOH (1M) by weight based on total solution weight (Solution A). HA was gently dissolved at room temperature (25° C.) in a portion of solution A to form an alkaline solution containing from 5 to 15 percent of hydrated HA by weight based on total solution weight (Solution B). PEGDE was dissolved at room temperature in a distilled water to form a neutral solution containing from 0.4 to 4 percent of PEGDE by weight based on total solution weight (Solution C1). Optionally, PEGDE was dissolved at room temperature in a portion of solution A to form an alkaline solution containing from 1 to 10 percent of PEGDE by weight based on total solution weight (Solution C2). Solution C (C1/C2) is then added to the solution B to provide an alkaline solution with a hydroxide concentration in the final solution in the range from 0.25 and 0.75M and with the desired ratio of HA and PEGDE. The resulting alkaline solution consisting of HA, PEGDE and NaOH is then thoroughly mixed at room temperature. The homogenous solution was then left to react at controlled temperature in the range between 20 and 50° C. for a period of time comprised from 1 to 48 hours. The comparative PEGDE cross-linked hyaluronic acid (hydrogel) was then washed with acidic water solution (1M hydrochloric acid and PBS) from 48 to 120 hours to remove unreacted materials and by products, to neutralize alkaline catalyst and restore the pH of the comparative PEGDE cross-linked hyaluronic acid (hydrogel) to 6.5-7.4 by ion exchange and to reach the final concentration of HA in the comparative PEGDE cross-linked hyaluronic acid (hydrogel) from 1 to 50 mg/mL as shown in Table below (Comp. PEGDE-HA Ex1-5).

The comparative PEGDE cross-linked hyaluronic acid (hydrogel) was filled into syringes and steam sterilized in autoclave following the pharmacopeia accepted reported in the EN ISO 17665-1 (e.g. 15 min at 121° C.). The hydrogel could be optionally dehydrated under vacuum at 30° C. and stored for following use or analysis.

Characterization of the Comparative PEGDE Crosslinked Hyaluronic Acid

The mechanical properties of the comparative PEGDE cross-linked hyaluronic acid falling outside the scope of the present invention obtained from the commercial PEGDE is disclosed in Table 6 having a concentration of 22.0 mg/mL of hyaluronic acid.

TABLE 6

| Comp. PEGDE-HA Ex. | Components of the PEGDE cross-linked HA: Conc. HA[a] | Conc. PEGDE[b] | Crosslinking reaction conditions: Temp. (° C.) | Time (h) | Mechanical parameters of the PEGDE cross-linked HA: G' at 0.7 Hz (Pa) | $D_N$ (nm) | C.D. (%) |
|---|---|---|---|---|---|---|---|
| 1 | 5.00 | 5.20 | 50 | 3 | undetectable | NA | NA |
| 2 | 8.00 | 2.60 | 40 | 4 | 13.93 ± 1.55 | 41.13 ± 0.19 | 0.0832 |
| 3 | 10.00 | 1.00 | 30 | 7 | 268.26 ± 6.65 | 27.77 ± 0.17 | 0.2702 |
| 4 | 10.00 | 0.80 | 30 | 6 | 137.60 ± 1.88 | 32.15 ± 0.09 | 0.1741 |
| 5 | 10.00 | 0.50 | 30 | 5 | 29.23 ± 1.56 | 39.31 ± 0.22 | 0.0944 |

[a]concentration of HA in the GDE cross-linked HA expressed as percentage by weight in relation to the total weight.
[b]concentration of PEGDE of the present invention in the PEGDE cross-linked HA expressed as percentage by weight in relation to the total weight.

2.1.3. Assays 2.1.3.1. Viability Assay

MTT assay was used to evaluate the viability of 3T3 mouse fibroblasts grown.

The MTT assays were performed with:

the comparative BDDE cross-linked hyaluronic acid (hydrogel) (Comparative BDDE-HA Ex. 3), comparative PEGDE cross-linked hyaluronic acid (hydrogel) (Comparative PEGDE-HA Ex. 3), PPE cross-linked hyaluronic acid (hydrogel) of the present invention (PPE-HA Ex. 3),

BDDE,

PEGDE, and

PPE (PPE Ex. 22 of the present invention).

a) MTT assay on cells grown in direct contact with tested hydrogel.

The MTT assay was performed on cells grown in direct contact with 100 mg of each tested sample. This MTT assay shows a difference in cell viability among all the three tested hydrogels with respect to control (represented by culture medium), which is attributed to an inhibition of cells proliferation caused mainly by a low space available due to hydrogel presence, rather than toxic or low biocompatibility tissues. In particular, the cell viability in the presence of the PPE cross-linked hyaluronic acid of the present invention is significantly higher in comparison with the control and with the comparative cross-linked hyaluronic acid with BDDE and PEDGE.

b) MTT assay on cells grown in the hydrogel's extract.

The MTT assay was performed on cells grown in the presence of tested hydrogel's extract obtained by immersion of the tested cross-linked hydrogel in culture medium for 24 hours.

The MTT assay, performed on cells grown in presence of extracts of the tested hydrogels shows no difference in cell viability among hydrogels and control, this means that all three tested hydrogels did not release toxic substances in medium when these hydrogels were soaked for 24 hours in culture medium. It is attributed to a good and controlled manufacturing process, in which all unreacted raw materials and by-products are efficiently removed during the cross-linking manufacturing.

c) MTT assay on cells grown in direct contact with the crosslinker

The MTT assay was performed on cells grown in direct contact with a solution containing cross-linker solutions. The solution contains the same epoxy equivalents, following the same steps of the manufacturing process of hydrogels—such as chemical reaction, washing and sterilization, but without the addition of the polysaccharide.

The MTT assay shows that the viability of cells grown in direct contact with PPE is not significantly different with respect to control (culture medium in NaCl 0.9%). The microscopic images confirmed that cells in direct contact with PPE have good shape and viability if compared with cells grown in direct contact with BDDE and PEGDE which instead show significant decrease of cells viability and signs of suffering.

2.1.3.2. Enzymatic Degradation Assay

The evaluation of enzymatic degradation rate was performed with:

the comparative BDDE cross-linked hyaluronic acid (hydrogel) Comp. BDDE-HA Ex. 3, comparative PEGDE cross-linked hyaluronic acid (hydrogel) Comp. PEGDE-HA Ex. 3, comparative GDE cross-linked hyaluronic acid (hydrogel) Comp. GDE-HA Ex. 3, and PPE cross-linked hyaluronic acid (hydrogel) of the present invention PPE-HA Ex. 4, PPE-HA Ex. 5 and PPE-HA Ex 6.

0.2 mL of each tested cross-linked hyaluronic acid (hydrogel) was treated with 10 μL of 0.1 mg/mL hyaluronidase from bovine tests (type IV-S; 1040 units/mg solid). Tested hydrogels were incubated for 16 hours at 37° C. in PBS, uronic acid from degraded hyaluronic acid was evaluated with carbazole assay. The 22 mg/mL tested cross-linked hyaluronic acid hydrogels showed degradation rate in response to hyaluronidase from 74.4% (BDDE cross-linked as control) to 26.3% of free uronic acid from enzymatic degradation.

The comparative BDDE hydrogel (Comp. BDDE-HA Ex. 3), the comparative PEGDE hydrogel (Comp.PEGDE-HA Ex. 3) and comparative GDE hydrogel (Comp. GDE-HA Ex. 3) cross-linked hyaluronic acid shown similar cross-linking degree and therefore, comparable amount of free uronic acid after enzymatic degradation of 74.4, 70.8, and 69.5% respectively.

The PPE hydrogels of the present invention (PPE-HA Ex. 4 and Ex. 5) shown a decreasing of cross-linking degree, therefore should be expected a decrease in the enzymatic degradation resistance, unexpectedly and counterintuitively, the amount of free uronic acid after enzymatic degradation is decreased to 56.7% and 26.3% respectively, indicating a statistical significance increasing of enzymatic degradation resistance.

The PPE cross-linked HA PPE-HA Ex 6 shown an amount of free uronic acid after enzymatic degradation of 58.0%, comparable with free uronic acid derived from PPE cross-linked HA from PPE-HA Ex. 4, indicating that enzymatic degradation resistance is comparable (56.7 and 58.0% respectively) even if the two hydrogel have two different cross-linking degree, in particular the C.D. from PPE-HA Ex 6 is significantly lower than the C.D. of PPE-HA Ex. 4 (0.2688 and 0.1528% respectively).

Therefore, the protective effect of the PPE of the present invention is significative higher against enzymatic degradation than the comparative GDE, BDDE and PEGDE. In particular, the protective effect of PPE with high molecular weight (i.e. from 3000 Da to 15000 Da) is higher than the protective effect of PPE with low molecular weight against enzymatic degradation (i.e. from 750 Da to lower than 3000 Da), even if the low molecular weight PPE give the better mechanical properties. The 22 mg/mL HA from experiment 51 hydrogel showed greater resistance to in vitro enzymatic degradation by hyaluronidase than the others.

The results of the enzymatic degradation assay of the comparative hyaluronic acid cross-linked with BDDE, PEGDE, GDE and the hyaluronic acid cross-linked with PPE of the present invention are summarized in Table below:

TABLE 7

| N° of crosslinked-HA | Crosslinker of the Crosslinked HA | Uronic acid t = 0 (control) (%) | Uronic acid t = 16 h, 37° C. (%) | C.D. (%) | % of relative degradation rate (to GDE) |
|---|---|---|---|---|---|
| Comp. BDDE-HA Ex. 3 | BDDE | 10.6 ± 0.8 | 74.4 ± 1.5 | 0.2716 | 107.1 ± 4.3 |
| Comp. PEGDE-HA Ex. 3 | PEGDE | 12.4 ± 0.9 | 70.8 ± 1.6 | 0.2702 | 101.8 ± 4.4 |
| Comp. GDE-HA Ex. 3 | 1,3-GDE | 13.1 ± 0.7 | 69.5 ± 1.4 | 0.2754[(a)] | 100.0 ± 4.0 |
| PPE-HA Ex. 8 | PPE Ex. 23 | 13.2 ± 0.9 | 69.6 ± 1.6 | 0.1358[(b)] | 100.2 ± 4.3 |
| PPE-HA Ex. 9 | PPE Ex. 16 | 12.8 ± 0.7 | 69.7 ± 1.6 | 0.1127[(c)] | 100.3 ± 4.3 |
| PPE-HA Ex. 4 | PPE Ex. 22 | 12.5 ± 0.8 | 56.7 ± 2.1 | 0.2688 | 81.6 ± 4.7 |
| PPE-HA Ex. 5 | PPE Ex. 23 | 13.1 ± 0.9 | 26.3 ± 3.3 | 0.1877 | 37.9 ± 5.5 |
| PPE-HA Ex 6 | PPE Ex. 16 | 15.4 ± 1.1 | 58.0 ± 1.7 | 0.1528 | 83.4 ± 4.1 |
| Comp. GDE-HA Ex. 6 | 1,3-GDE | 3.7 ± 0.2 | 61.1 ± 0.8 | 0.4037 | 100.0 ± 5.0 |
| PPE-HA Ex. 14 | PPE Ex. 22 | 4.2 ± 0.3 | 49.2 ± 0.9 | 0.3911 | 80.5 ± 6.3 |
| PPE-HA Ex. 15 | PPE Ex. 23 | 3.5 ± 0.2 | 21.3 ± 0.6 | 0.3049 | 34.9 ± 2.6 |
| PPE-HA Ex. 16 | PPE Ex. 216 | 3.8 ± 0.2 | 50.6 ± 0.7 | 0.2723 | 82.8 ± 4.8 |

[(a)]C.D. = 0.2745; G' = 274.17 ± 9.54 and $D_N$ = 27.62 ± 0.23

[(b)]C.D. = 0.1358; G' = 85.56 ± 2.94 and $D_N$ = 34.92 ± 0.19

[(c)]C.D = 0.1127; G' = 54.09 ± 4.07 and $D_N$ = 37. 17 ± 0.33

Therefore, as it is shown in the above results, the cross-linked polysaccharides of the present invention prepared by using the hyperbranched PPE of the present invention as a crosslinker have a better enzymatic degradation resistance (which means a lower percentage of relative enzymatic degradation rate) than crosslinked polysaccharides falling outside the scope of protection of the present invention prepared by using the above-disclosed comparative cross-linkers but having comparable physical properties. In particular, it is demonstrated that crosslinked polysaccharides of the present invention (obtained by using the hyper-branched PPE of the present invention as a crosslinker), having comparable physical properties (numerically expressed by the value of G', and consequently by the value of $D_N$ and C.D.) to the comparative crosslinked polysaccharides falling outside of the scope of protection of the present invention (obtained using commercial GDE, BDDE and PEGDE as a crosslinker) have a greater enzymatic resistance (i.e. lower enzymatic degradation rate).

Furthermore, the above results also show that the cross-linked polysaccharides of the present invention (obtained by using the hyperbranched PPE of the present invention as a crosslinker), have a higher enzymatic degradation rate with a lower amount of crosslinker, which is numerically expressed for having the same degradation rate as the comparative crosslinked polysaccharides but a lower value of G', $D_N$ and C.D. This is advantageous because the lower chemical modification of the polysaccharide due to the lower amount of crosslinked used improve its biocompatibility and safety after its injection in the skin.

2.1.3.3. Oxidative Degradation Assay

Samples:

The evaluation of oxidative degradation rate was performed with:

the comparative BDDE cross-linked hyaluronic acid Comp. BDDE-HA Ex. 3, comparative PEGDE cross-linked hyaluronic acid Comp. PEGDE-HA Ex. 3, comparative GDE cross-linked hyaluronic acid Comp. GDE-HA Ex. 3, and PPE cross-linked hyaluronic acid of the present invention PPE-HA Ex. 4, PPE-HA Ex. 5 and PPE-HA Ex 6.

Method:

The resistance to oxidative degradation was evaluated following the method disclosed in the state of the art (cf. Bitter, T. and H. M. Muir, "*A modified uronic acid carbazole reaction*. Analytical Biochemistry", 1962, vol. 4(4), pp. 330-334):

0.2 mL of each tested cross-linked hyaluronic acid was treated with Fenton's reagent (10 μL of 0.1M $Fe^{+2}/H_2O_2$ and 25 μL 0.1M of ascorbic acid in 5 mL of PBS), incubated for 24 hours at 37° C. Uronic acid from degraded hyaluronic acid was evaluated with carbazole assay. The 22 mg/mL tested cross-linked hyaluronic acid showed degradation rate in response to oxidation from 88.0% (PEGDE cross-linked) to 61.6% of free uronic acid from oxidative degradation.

The comparative BDDE cross-linked hyaluronic acid (Comp. BDDE-HA Ex. 3), the comparative PEGDE cross-linked hyaluronic acid (Comp. PEGDE-HA Ex. 3) and the comparative GDE hydrogel cross-linked hyaluronic acid (Comp. GDE-HA Ex. 3) show comparable cross-linking degree and therefore, comparable amount of free uronic acid after oxidative degradation of 81.2, 88.0 and 80.2 respectively, with the PEGDE cross-linked hyaluronic acid the most sensitive to oxidative degradation.

The PPE crosslinked hyaluronic acid of the present invention (PPE-HA Ex. 4 and PPE-HA Ex. 5) shows a decreasing of cross-linking degree, therefore should be expected a decrease the oxidative degradation resistance, unexpectedly and counterintuitively, the amount of free uronic acid after oxidative degradation is decreased to 65.9 and 61.6 respectively, indicating a statistical significance increasing of oxidative degradation resistance. The PPE cross-linked HA of the present invention from PPE-HA Ex 6 shows an amount of free uronic acid after oxidative degradation of 69.6%, little higher than free uronic acid derived from PPE cross-linked HA from PPE-HA Ex. 4 and PPE-HA Ex. 5, but statistical significant lower than the experiments 3, 8 and 13, indicating that oxidative degradation resistance of PPE cross-linked hyaluronic acid of the present invention is higher than the comparative BDDE, PEGDE and GDE cross-linked polysaccharides falling outside of the scope of the present invention.

Results:

The results of the oxidative degradation assay of the comparative hyaluronic acid cross-linked with BDDE, PEGDE, GDE and the hyaluronic acid cross-linked with PPE of the present invention are summarized in Table below:

TABLE 8

| N° of crosslinked-HA | Cross-linker of the crosslinked HA | Uronic acid t = 0 (control) (%) | Uronic acid t = 24 h, 37° C. (%) | C.D. (%) | % of relative degradation rate$^{color}$ (to GDE) |
|---|---|---|---|---|---|
| Comp. BDDE-HA Ex. 3 | BDDE | 10.6 ± 0.8 | 81.2 ± 2.7 | 0.2716 | 101.2 ± 7.0 |
| Comp. PEGDE-HA Ex. 3 | PEGDE | 12.4 ± 0.9 | 88.0 ± 1.7 | 0.2702 | 109.7 ± 6.1 |
| Comp. GDE-HA Ex. 3 | 1,3-GDE | 13.1 ± 0.7 | 80.2 ± 2.9 | 0.2754[(a)] | 100.0 ± 7.2 |
| PPE-HA Ex. 8 | PPE Ex. 23 | 13.2 ± 0.9 | 81.5 ± 1.9 | 0.1358[(b)] | 101.6 ± 6.0 |
| PPE-HA Ex. 9 | PPE Ex. 16 | 13.1 ± 0.7 | 81.2 ± 2.2 | 0.1127[(c)] | 101.2 ± 6.4 |
| PPE-HA Ex. 4 | PPE Ex. 22 | 12.5 ± 0.8 | 65.9 ± 3.6 | 0.2688 | 82.1 ± 7.0 |
| PPE-HA Ex. 5 | PPE Ex. 23 | 13.1 ± 0.9 | 61.6 ± 2.3 | 0.1877 | 76.8 ± 5.3 |
| PPE-HA Ex 6 | PPE Ex. 16 | 15.4 ± 1.1 | 69.6 ± 2.3 | 0.1528 | 86.7 ± 5.6 |
| Comp. GDE-HA Ex. 6 | 1,3-GDE | 3.7 ± 0.2 | 79.0 ± 0.7 | 0.4037 | 100.0 ± 4.9 |
| PPE-HA Ex. 14 | PPE Ex. 22 | 4.2 ± 0.3 | 65.6 ± 0.5 | 0.3911 | 83.1 ± 6.4 |
| PPE-HA Ex. 15 | PPE Ex. 23 | 3.5 ± 0.2 | 58.9 ± 0.6 | 0.3049 | 75.8 ± 5.3 |
| PPE-HA Ex. 16 | PPE Ex. 216 | 3.8 ± 0.2 | 66.5 ± 0.7 | 0.2723 | 84.1 ± 4.8 |

[(a)]C.D. = 0.2745; G' = 274.17 ± 9.54; and DN = 27.62 ± 0.23

[(b)]C.D. = 0.1358; G' = 85.56 ± 2.94; and DN = 34.92 ± 0.19

[(c)]C.D. = 0.1127; G' = 54.09 ± 4.07; and DN = 37.17 ± 0.33

Therefore, as it is shown in the above results and it is mentioned above for the enzymatic degradation rate, the crosslinked polysaccharides of the present invention prepared by using the hyperbranched PPE of the present invention as a crosslinker have a better oxidative degradation resistance (which means a lower percentage of relative oxidative degradation rate) than crosslinked polysaccharides falling outside the scope of protection of the present invention prepared by using the above-disclosed comparative crosslinkers but having comparable physical properties.

Furthermore, the above results also show that the crosslinked polysaccharides of the present invention (obtained by using the hyperbranched PPE of the present invention as a crosslinker), have a higher oxidative degradation rate with a lower amount of crosslinker. This is advantageous because the lower chemical modification of the polysaccharide due to the lower amount of crosslinked used improve its biocompatibility and safety after its injection in the skin.

2.2. Cross-Linked Amylose Starch

2.2.1. PPE Cross-Linked Amylose Starch of the Present Invention (PPE-AS)

The below-mentioned PPE-AS is prepared by using the Denacol® EX-313 commercially available from Nagase as a source of 1,3-GDE. Nevertheless, these processes can be also performed by using the 1,3-glycerol diglycidyl ether commercially available from Merck or with the trademark Denacol® EX-314 which is a mixture containing 1,3-DGE instead of Denacol® EX-313.

Preparation Process

Sodium hydroxide pellets (NaOH) were dissolved in water to form an alkaline solution containing a 4 percent of NaOH (1M) by weight based on total solution weight (Solution A). 1,3-GDE was dissolved at room temperature in a portion of solution A to form an alkaline solution containing from 1 to 50 percent of GDE by weight based on total solution weight (Solution C1). Solution C1 was then left to react at controlled temperature in the range between 10 and 40° C. for a period comprised from 1 to 30 days or alternatively at controlled temperature in the range between 20 and 50° C. for a period comprised from 1 to 48 hours during which self-polymerization of 1,3-GDE take place giving the Polyglycerol Polyglycidyl Ether with a the molecular weight and/or specific epoxy content disclosed in Table 1 (Solution C3).

High content amylose starch was gently dispersed at room temperature (25° C.) in a portion of solution A to form an alkaline solution containing from 5 to 15 percent of hydrated high content amylose starch by weight based on total solution weight (Solution B). The solution C3 is then added to the solution B to provide an alkaline solution with a hydroxide concentration in the final solution in the range from 0.25 and 0.75M and with the ratio of high content amylose starch and PPE. The resulting alkaline solution consisting of high content amylose starch, PPE and NaOH is then thoroughly mixed at room temperature. The homogenous solution was then left to react at controlled temperature in the range between 20 and 50° C. for a period comprised from 1 to 48 hours.

The PPE cross-linked high content amylose starch (hydrogel) was then washed with acidic water solution (1M hydrochloric acid and PBS) from 48 to 120 hours to remove unreacted materials and by-products, to neutralize alkaline catalyst and restore the pH of hydrogel to 6.5-7.4 by ion exchange and to reach the concentration of high content amylose starch in the PPE cross-linked amylose starch (hydrogel) from 1 to 50 mg/mL as shown in Table below (PPE-AS Ex. 1-3).

The PPE cross-linked amylose starch hydrogel was filled into syringes and steam sterilized in autoclave following the pharmacopeia accepted reported in the EN ISO 17665-1 (e.g. 15 min at 121° C.). The PPE cross-linked amylose starch hydrogel could be optionally dehydrated by freeze-drying and stored for following use or analysis.

2.2.2. Comparative GDE Cross-Linked Amylose Starch (Comp. GDE-AS)

The comparative GDE cross-linked amylose starch was prepared following the process as disclosed above in section 2.1.2.1. for the comparative 1,3-GDE cross-linked hyaluronic acid but using amylose starch instead of hyaluronic acid.

2.2.3. Characterization of the Cross-Linked Amylose Starch

The mechanical properties of the PPE cross-linked amylose starch of the present invention (PPE-AS) and the comparative GDE cross-linked amylose starch (Comp. GDE-AS) obtained above are disclosed in Table below.

TABLE 9

| | Components of the cross-linked amylose starch | | | Crosslinking reaction conditions | | Mechanical parameters of the cross-linked polysaccharide | | |
|---|---|---|---|---|---|---|---|---|
| N° of crosslinked amylose | Conc. Amylose[(a)] | Cross-linker | Conc. cross-linker[(b)] | T[a] (° C.) | Time (h) | G' at 0.7 Hz (Pa) | $D_N$ (nm) | C.D. (%) |
| Comp GDE-AS Ex.1 | 10.00 | 1,3-GDE | 0.4 | 30 | 7 | 250.78 ± 2.26 | 22.54 ± 0.02 | 0.2041 |
| PPE-AS Ex. 1 | 10.00 | PPE Ex. 22 | 0.4 | 30 | 7 | 230.63 ± 2.14 | 22.76 ± 0.02 | 0.1981 |
| PPE-AS Ex. 2 | 10.00 | PPE Ex. 23 | 0.4 | 30 | 8 | 111.04 ± 2.60 | 24.31 ± 0.04 | 0.1626 |
| PPE-AS Ex. 3 | 10.00 | PPE Ex. 16 | 0.4 | 30 | 9 | 84.76 ± 2.75 | 24.71 ± 0.07 | 0.01548 |

[(a)]concentration of amylose in the cross-linked hydrogel expressed as percentage by weight in relation to the total weight.

[(b)]concentration of the crosslinker of the present invention in the cross-linked amylose expressed as percentage by weight in relation to the total weight.

2.2.4 Assay 2.2.4.1 Enzymatic Degradation Assay

Samples:

The evaluation of enzymatic degradation rate was performed with:

the comparative GDE cross-linked amylose starch (hydrogel) Comp. GDE-AS Ex. 1, and PPE cross-linked amylose starch (hydrogel) of the present invention PPE-AS Ex. 1, PPE-AS Ex. 2 and PPE-AS Ex. 3.

Method:

0.2 mL of each tested cross-linked amylose starch (hydrogel) was treated with 10 μL of 0.1 mg/mL α-amylases from *Bacillus licheniformis* (lyophilized powder, 500-1,500 units/mg protein). Tested hydrogels were incubated for 16 hours at 37° C. in PBS, hexoses monomers from degraded amylose starch hydrogel was evaluated with carbazole assay. The 22 mg/mL tested cross-linked amylose starch hydrogels showed relative enzymatic degradation rate in response to α-amylases from 80.3% to 41.7%.

Results:

The comparative GDE cross-linked amylose starch (Comp. GDE-AS Ex. 1) and the PPE cross-linked amylose starch of the present invention (PPE-AS Ex. 1) show comparable cross-linking degree, the PPE hydrogels of the present invention (PPE-AS Ex. 2 and PPE-AS Ex. 3) shown a decreasing of cross-linking degree, therefore should be expected a decrease in the enzymatic degradation resistance, unexpectedly and counterintuitively, the amount of free hexoses monomers after enzymatic degradation is decreased to 41.7% and 80.0% respectively, indicating a statistical significance increasing of enzymatic degradation resistance.

The PPE cross-linked HA PPE-AS Ex 3 shown an amount of free hexoses monomers after enzymatic degradation comparable with the amount of free hexoses monomers derived from PPE cross-linked starch from PPE-AS Ex. 1, indicating that enzymatic degradation resistance is comparable (80.0% and 80.3 respectively) even if the two hydrogel have two different cross-linking degree, in particular the C.D. from PPE-AS Ex 3 is significantly lower than the C.D. of PPE-AS Ex. 1 (0.1548 and 0.1981% respectively).

Therefore, the protective effect of the PPE of the present invention is significative higher against enzymatic degradation than the comparative GDE. In particular, the protective effect of PPE with high molecular weight (i.e. from 3000 Da to 15000 Da) is higher than the protective effect of PPE with low molecular weight against enzymatic degradation (i.e. from 750 Da to lower than 3000 Da), even if the low molecular weight PPE give the better mechanical properties. The 22 mg/mL AS from PPE-AS Ex. 2 showed greater resistance to in vitro enzymatic degradation by hyaluronidase than the others.

The results of the enzymatic degradation assay of the comparative amylose starch cross-linked with GDE and the amylose starch cross-linked with PPE of the present invention are summarized in Table below:

TABLE 10

| N° of crosslinked-AS | Crosslinker of the Crosslinked AS | Hexoses t = 0 (control) (%) | Hexoses t = 16 h, 37° C. (%) | C.D. (%) | % of relative degradation rate (to GDE) |
|---|---|---|---|---|---|
| Comp. GDE-AS Ex. 1 | 1,3-GDE | 10.8 ± 0.7 | 70.5 ± 0.7 | 0.2041 | 100.0 ± 6.6 |
| PPE-AS Ex. 1 | PPE Ex. 22 | 10.6 ± 0.8 | 56.6 ± 0.8 | 0.1981 | 80.3 ± 6.1 |
| PPE-AS Ex. 2 | PPE Ex. 23 | 11.0 ± 0.9 | 29.4 ± 0.7 | 0.1626 | 41.7 ± 3.5 |
| PPE-AS Ex. 3 | PPE Ex. 16 | 1.8 ± 0.9 | 56.4 ± 0.7 | 0.1548 | 80.0 ± 5.7 |

Therefore, as it is shown in the above results, the crosslinked polysaccharides of the present invention prepared by using the hyperbranched PPE of the present invention as a crosslinker have a better enzymatic degradation resistance (which means a lower percentage of relative enzymatic degradation rate) than crosslinked polysaccharides falling outside the scope of protection of the present invention prepared by using the above-disclosed comparative crosslinkers but having comparable physical properties. In particular, it is demonstrated that crosslinked polysaccharides of the present invention (obtained by using the hyperbranched PPE of the present invention as a crosslinker) have a greater enzymatic resistance (i.e. lower enzymatic degradation rate). Furthermore, the above results also show that the crosslinked polysaccharides of the present invention (obtained by using the hyperbranched PPE of the present invention as a crosslinker), have a higher enzymatic degradation rate with a lower amount of crosslinker.

2.2.4.2 Oxidative Degradation Assay

Samples:

The evaluation of oxidative degradation rate was performed with:

the comparative GDE cross-linked amylose starch Comp. GDE-AS Ex. 1, and

PPE cross-linked amylose starch of the present invention PPE-AS Ex. 1, PPE-AS Ex. 2 and PPE-AS Ex. 3.

Method:

The resistance to oxidative degradation was evaluated following the method disclosed in the state of the art (cf. Bitter, T. and H. M. Muir, "*A modified uronic acid carbazole reaction*. Analytical Biochemistry", 1962, vol. 4(4), pp. 330-334):

0.2 mL of each tested cross-linked amylose starch was treated with Fenton's reagent (10 μL of 0.1M $Fe^{+2}/H_2O_2$ and 25 μL 0.1M of ascorbic acid in 5 mL of PBS), incubated for 24 hours at 37° C. The free hexoses monomers from degraded amylose starch hydrogel was evaluated with carbazole assay. The 22 mg/mL tested cross-linked amylose starch showed degradation rate in response to oxidation from 83.8% to 77.4%.

Results:

The comparative GDE cross-linked amylose starch (Comp. GDE-AS Ex. 1) and the PPE cross-linked amylose starch of the present invention (PPE-AS Ex. 1) show comparable cross-linking degree, the PPE crosslinked amylose starch of the present invention (PPE-AS Ex. 2 and PPE-AS Ex. 3) shows a decreasing of cross-linking degree, therefore should be expected a decrease the oxidative degradation resistance, unexpectedly and counterintuitively, the amount of free hexoses monomers after oxidative degradation is decreased to 83.8, 77.4 and 81.0 respectively for PPE-AS Ex. 1, PPE-AS Ex. 2 and PPE-AS Ex. 3, indicating a statistical significance increasing of oxidative degradation resistance.

Therefore, as it is shown in the above results and it is mentioned above for the oxidative degradation rate, the crosslinked polysaccharides of the present invention prepared by using the hyperbranched PPE of the present invention as a crosslinker have a better oxidative degradation resistance (which means a lower percentage of relative oxidative degradation rate) than crosslinked polysaccharides falling outside the scope of protection of the present invention prepared by using the above-disclosed comparative crosslinkers but having comparable physical properties.

The results of the oxidative degradation assay of the comparative amylose starch cross-linked with GDE and the amylose starch cross-linked with PPE of the present invention are summarized in Table below:

TABLE 11

| N° of crosslinked-AS | Cross-linker of the crosslinked AS | Hexoses t = 0 (control) (%) | Hexoses t = 24 h, 37° C. (%) | C.D. (%) | % of relative degradation rate (to GDE) |
|---|---|---|---|---|---|
| Comp. GDE-AS Ex. 1 | 1,3-GDE | 10.8 ± 0.7 | 70.8 ± 0.8 | 0.2041 | 100.0 ± 6.6 |
| PPE-AS Ex. 1 | PPE Ex. 22 | 10.6 ± 0.8 | 59.4 ± 0.8 | 0.1981 | 83.8 ± 6.4 |
| PPE-AS Ex. 2 | PPE Ex. 23 | 11.0 ± 0.9 | 54.8 ± 0.7 | 0.1626 | 77.4 ± 6.4 |
| PPE-AS Ex. 3 | PPE Ex. 16 | 1.8 ± 0.9 | 57.4 ± 0.7 | 0.1548 | 81.0 ± 5.9 |

Therefore, as it is shown in the above results and it is mentioned above for the enzymatic degradation rate, the crosslinked polysaccharides of the present invention prepared by using the hyperbranched PPE of the present invention as a crosslinker have a better oxidative degradation resistance (which means a lower percentage of relative oxidative degradation rate) than crosslinked polysaccharides falling outside the scope of protection of the present invention prepared by using the above-disclosed comparative crosslinkers but having comparable physical properties. Furthermore, the above results also show that the crosslinked polysaccharides of the present invention (obtained by using the hyperbranched PPE of the present invention as a crosslinker), have a higher oxidative degradation rate with a lower amount of crosslinker.

2.3. Cross-Linked Amylopectin Starch/Glycogen

2.3.1. PPE Cross-Linked Amylopectin Starch/Glycogen of the Present Invention (PPE-ASG)

The below-mentioned PPE-ASG is prepared by using the Denacol® EX-313 commercially available from Nagase as a source of 1,3-GDE. Nevertheless, these processes can be also performed by using the 1,3-glycerol diglycidyl ether commercially available from Merck or with the trademark Denacol® EX-314 which is a mixture containing 1,3-DGE instead of Denacol® EX-313.

Preparation Process

Sodium hydroxide pellets (NaOH) were dissolved in water to form an alkaline solution containing a 4 percent of NaOH (1M) by weight based on total solution weight (Solution A). 1,3-GDE was dissolved at room temperature in a portion of solution A to form an alkaline solution containing from 1 to 50 percent of GDE by weight based on total solution weight (Solution C1). Solution C1 was then left to react at a temperature in the range between 10 and 40° C. for a period comprised from 1 to 30 days or alternatively at controlled temperature in the range between 20 and 50° C. for a period comprised from 1 to 48 hours during which self-polymerization of 1,3-GDE take place giving the Polyglycerol Polyglycidyl Ether of the present invention with a molecular weight and/or specific epoxy content disclosed in Table 1 (Solution C3).

High content amylopectin starch/glycogen was gently dispersed at room temperature (25° C.) in a portion of solution A to form an alkaline solution containing from 5 to 15 percent of hydrated high content amylopectin starch/glycogen by weight based on total solution weight (Solution B). The solution C3 is then added to the solution B to provide an alkaline solution with a hydroxide concentration in the final solution in the range from 0.25 and 0.75M and with the ratio of high content amylopectin starch/glycogen and PPE. The resulting alkaline solution consisting of high content amylopectin starch/glycogen, PPE and NaOH is then thoroughly mixed at room temperature. The homogenous solution was then left to react at controlled temperature in the range between 20 and 50° C. for a period comprised from 1 to 48 hours.

The PPE cross-linked high content amylopectin starch/glycogen (hydrogel) of the present invention (PPE-ASG Ex. 1-3) was then washed with acidic water solution (1M hydrochloric acid and PBS) from 48 to 120 hours to remove unreacted materials and by-products, to neutralize alkaline catalyst and restore the pH of hydrogel to 6.5-7.4 by ion exchange and to reach the concentration of high content amylopectin starch/glycogen crosslinked with PPE (hydrogel) of the present invention from 1 to 50 mg/mL as shown in Table below (PPE-ASG Ex. 1-3).

The amylopectin starch/glycogen crosslinked with PPE (hydrogel) was filled into syringes and steam sterilized in autoclave following the pharmacopeia reported in the EN ISO 17665-1 (e.g. 15 min at 121° C.). The amylopectin starch/glycogen crosslinked with PPE (hydrogel) of the present invention could be optionally dehydrated in a ventilated oven at 50° C. and stored for following use or analysis.

2.3.2. Comparative GDE Cross-Linked Amylopectin Starch/Glycogen (Comp. GDE-ASG)

The comparative GDE cross-linked amylopectin starch/glycogen (Comp. GDE-ASG) was prepared following the process as disclosed above in section 2.1.2.1. for the comparative GDE cross-linked hyaluronic acid but using amylopectin starch/glycogen instead of hyaluronic acid.

2.3.3. Characterization of the Cross-Linked Amylopectin Starch/Glycogen

The mechanical properties of the PPE cross-linked amylopectin starch/glycogen of the present invention (PPE-ASG) and the comparative GDE cross-linked amylopectin starch/glycogen (Comp. GDE-ASG) obtained above are disclosed in Table below, having a concentration of 22.0 mg/mL:

TABLE 12

| | Components of the cross-linked amylopectin starch/glycogen | | | Cross-linking reaction conditions | | Mechanical parameters of the cross-linked polysaccharide | | |
|---|---|---|---|---|---|---|---|---|
| N° of crosslinked amylopectin starch/glycogen | Conc. Amylopectin starch/glycogen[(a)] | Cross-linker | Conc. Crosslinker[(b)] | T[a] (° C.) | Time (h) | G' at 0.7 Hz (Pa) | $D_N$ (nm) | C.D. (%) |
| Comp GDE-ASG Ex.1 | 10.00 | 1,3-GDE | 0.4 | 30 | 7 | 299.98 ± 4.13 | 23.43 ± 0.05 | 0.1817 |
| PPE-ASG Ex. 1 | 10.00 | PPE Ex. 22 | 0.4 | 30 | 7 | 262.16 ± 1.92 | 23.93 ± 0.03 | 0.1704 |
| PPE-ASG Ex. 2 | 10.00 | PPE Ex. 23 | 0.4 | 30 | 8 | 144.91 ± 2.81 | 25.83 ± 0.05 | 0.1356 |
| PPE-ASG Ex. 3 | 10.00 | PPE Ex. 16 | 0.4 | 30 | 9 | 105.98 ± 2.79 | 26.61 ± 0.06 | 0.1241 |

[(a)]concentration of amylopectin starch/glycogen in the cross-linked hydrogel expressed as percentage by weight in relation to the total weight.
[(b)]concentration of crosslinker in the cross-linked amylopectin starch/glycogen expressed as percentage by weight in relation to the total weight.

2.3.4 Assay

2.3.4.1 Enzymatic Degradation Assay

Samples:

The evaluation of enzymatic degradation rate was performed with:

the comparative GDE cross-linked amylopectin starch/glycogen (hydrogel) Comp. GDE-ASG Ex. 1, and PPE cross-linked amylopectin starch/glycogen (hydrogel) of the present invention PPE-ASG Ex. 1, PPE-ASG Ex. 2 and PPE-ASG Ex. 3.

Method:

The resistance to enzymatic degradation was evaluated following the method disclosed in the previous section 2.2.4.1 Enzymatic degradation assay.

Results:

The PPE hydrogels of the present invention (PPE ASG Ex. 2 and PPE-ASG Ex. 3) shown a decreasing of cross-linking degree, therefore should be expected a decrease in the enzymatic degradation resistance, unexpectedly and counterintuitively, the amount of free hexoses monomers after enzymatic degradation is decreased to 76.0% and 89.4% respectively, indicating a statistical significance increasing of enzymatic degradation resistance.

The comparative GDE cross-linked amylopectin starch/glycogen (Comp. GDE-ASG Ex. 1) and the PPE cross-linked amylopectin starch/glycogen of the present invention (PPE-ASG Ex. 1) show comparable cross-linking degree, the PPE crosslinked amylopectin starch/glycogen of the present invention (PPE-ASG Ex. 2 and PPE-ASG Ex. 3) shows a decreasing of cross-linking degree, therefore should be expected a decrease the oxidative degradation resistance, unexpectedly and counterintuitively, the PPE cross-linked HA PPE-ASG Ex 3 shown an amount of free hexoses monomers after enzymatic degradation comparable with the amount of free hexoses monomers derived from PPE cross-linked starch from PPE-ASG Ex. 1, indicating that enzymatic degradation resistance is comparable (89.4% and 85.7 respectively) even if the two hydrogel have two different cross-linking degree, in particular the C.D. from PPE-ASG Ex 3 is significantly lower than the C.D. of PPE-ASG Ex. 1 (0.1241 and 0.1708% respectively).

Therefore, the protective effect of the PPE of the present invention is significative higher against enzymatic degradation than the comparative GDE. In particular, the protective effect of PPE with high molecular weight (i.e. from 3000 Da to 15000 Da) is higher than the protective effect of PPE with low molecular weight against enzymatic degradation (i.e. from 750 Da to lower than 3000 Da), even if the low molecular weight PPE give the better mechanical properties. The 22 mg/mL AS from PPE-AS Ex. 2 showed greater resistance to in vitro enzymatic degradation by hyaluronidase than the others.

The results of the enzymatic degradation assay of the comparative amylopectin starch/glycogen cross-linked with GDE and the amylopectin starch/glycogen cross-linked with PPE of the present invention are summarized in Table below:

TABLE 13

| N° of crosslinked ASG | Crosslinker of the Crosslinked ASG | Hexoses t = 0 (control) (%) | Hexoses t = 16 h, 37° C. (%) | C.D. (%) | % of relative degradation rate (to GDE) |
|---|---|---|---|---|---|
| Comp. GDE-ASG Ex. 1 | 1,3-GDE | 11.0 ± 0.6 | 76.3 ± 0.4 | 0.1817 | 100.0 ± 5.5 |
| PPE-ASG Ex. 1 | PPE Ex. 22 | 12.2 ± 0.9 | 65.4 ± 0.4 | 0.1708 | 85.7 ± 6.5 |
| PPE-ASG Ex. 2 | PPE Ex. 23 | 11.9 ± 0.8 | 57.9 ± 1.0 | 0.1356 | 76.0 ± 5.3 |
| PPE-ASG Ex. 3 | PPE Ex. 16 | 11.0 ± 0.8 | 68.2 ± 0.3 | 0.1241 | 89.4 ± 6.4 |

Therefore, as it is shown in the above results, the cross-linked polysaccharides of the present invention prepared by using the hyperbranched PPE of the present invention as a crosslinker have a better enzymatic degradation resistance (which means a lower percentage of relative enzymatic degradation rate) than crosslinked polysaccharides falling outside the scope of protection of the present invention prepared by using the above-disclosed comparative cross-linkers but having comparable physical properties. In particular, it is demonstrated that crosslinked polysaccharides of the present invention (obtained by using the hyper-branched PPE of the present invention as a crosslinker) have a greater enzymatic resistance (i.e. lower enzymatic degradation rate). Furthermore, the above results also show that the crosslinked polysaccharides of the present invention (obtained by using the hyperbranched PPE of the present invention as a crosslinker), have a higher enzymatic degradation rate with a lower amount of crosslinker.

2.3.4.2 Oxidative Degradation Assay

Samples:

The evaluation of oxidative degradation rate was performed with:

the comparative GDE cross-linked amylopectin starch/glycogen Comp. GDE-ASG Ex. 1, and PPE cross-linked amylopectis starch/glycogen of the present invention PPE-ASG Ex. 1, PPE-ASG Ex. 2 and PPE-ASG Ex. 3.

Method:

The resistance to oxidative degradation was evaluated following the method disclosed in the previous section 2.2.4.2 Oxidative degradation assay.

Results:

The comparative GDE cross-linked amylopectin starch/glycogen (Comp. GDE-ASG Ex. 1) and the PPE cross-linked amylopectin starch/glycogen of the present invention (PPE-ASG Ex. 1) show comparable cross-linking degree, the PPE crosslinked amylose starch of the present invention (PPE-ASG Ex. 2 and PPE-ASG Ex. 3) shows a decreasing of cross-linking degree, therefore should be expected a decrease the oxidative degradation resistance, unexpectedly and counterintuitively, the amount of free hexoses monomers after oxidative degradation is decreased to 81.2, 74.5 and 87.0 respectively for PPE-ASG Ex. 1, PPE-ASG Ex. 2 and PPE-ASG Ex. 3, indicating a statistical significance increasing of oxidative degradation resistance.

Therefore, as it is shown in the above results and it is mentioned above for the oxidative degradation rate, the crosslinked polysaccharides of the present invention prepared by using the hyperbranched PPE of the present invention as a crosslinker have a better oxidative degradation resistance (which means a lower percentage of relative oxidative degradation rate) than crosslinked polysaccharides falling outside the scope of protection of the present invention prepared by using the above-disclosed comparative crosslinkers but having comparable physical properties.

The results of the oxidative degradation assay of the comparative amylopectin starch/glycogen cross-linked with GDE and the amylopectin starch/glycogen cross-linked with PPE of the present invention are summarized in Table below:

TABLE 14

| N° of crosslinked ASG | Cross-linker of the crosslinked ASG | Hexoses t = 0 (control) (%) | Hexoses t = 24 h, 37° C. (%) | C.D. (%) | % of relative degradation rate (to GDE) |
|---|---|---|---|---|---|
| Comp. GDE-ASG Ex. 1 | 1,3-GDE | 11.0 ± 0.6 | 87.3 ± 1.1 | 0.1817 | 100.0 ± 5.6 |
| PPE-ASG Ex. 1 | PPE Ex. 22 | 12.2 ± 0.9 | 70.9 ± 1.2 | 0.1708 | 81.2 ± 6.3 |
| PPE-ASG Ex. 2 | PPE Ex. 23 | 11.9 ± 0.8 | 65.0 ± 1.0 | 0.1356 | 74.5 ± 5.2 |
| PPE-ASG Ex. 3 | PPE Ex. 16 | 11.0 ± 0.8 | 75.9 ± 0.4 | 0.1241 | 87.0 ± 6.3 |

Therefore, as it is shown in the above results and it is mentioned above for the enzymatic degradation rate, the crosslinked polysaccharides of the present invention prepared by using the hyperbranched PPE of the present invention as a crosslinker have a better oxidative degradation resistance (which means a lower percentage of relative oxidative degradation rate) than crosslinked polysaccharides falling outside the scope of protection of the present invention prepared by using the above-disclosed comparative crosslinkers but having comparable physical properties. Furthermore, the above results also show that the crosslinked polysaccharides of the present invention (obtained by using the hyperbranched PPE of the present invention as a crosslinker), have a higher oxidative degradation rate with a lower amount of crosslinker.

2.4. Cross-Linked Sodium Carboxymethyl Cellulose

2.4.1. PPE Cross-Linked Sodium Carboxymethyl Cellulose of the Present Invention (PPE-CMC)

The below-mentioned PPE-CMC is prepared by using the Denacol® EX-313 commercially available from Nagase as a source of 1,3-GDE. Nevertheless, these processes can be also performed by using the 1,3-glycerol diglycidyl ether commercially available from Merck or with the trademark Denacol® EX-314 which is a mixture containing 1,3-DGE instead of Denacol® EX-313.

Preparation Process

Sodium hydroxide pellets (NaOH) were dissolved in water to form an alkaline solution containing a 4 percent of NaOH (1M) by weight based on total solution weight (Solution A). 1,3-GDE was dissolved at room temperature in a portion of solution A to form an alkaline solution containing from 1 to 50 percent of GDE by weight based on total solution weight (Solution C1). Solution C1 was then left to react at a temperature in the range between 10 and 40° C. for a period comprised from 1 to 30 days or alternatively at controlled temperature in the range between 20 and 50° C. for a period comprised from 1 to 48 hours during which self-polymerization of 1,3-GDE take place giving the Polyglycerol Polyglycidyl Ether of the present invention with a molecular weight and/or specific epoxy content as disclosed in Table 1 (Solution C3).

Sodium carboxymethyl cellulose (NaCMC) was gently dispersed at room temperature (25° C.) in a portion of solution A to form an alkaline solution containing from 5 to 15 percent of hydrated NaCMC by weight based on total solution weight (Solution B). The solution C3 is then added to the solution B to provide an alkaline solution with a hydroxide concentration in the final solution in the range from 0.25 and 0.75M and with the desired ratio of NaCMC and PPE. The resulting alkaline solution consisting of NaCMC, PPE and NaOH is then thoroughly mixed at room temperature. The homogenous solution was then left to react at controlled temperature in the range between 20 and 50° C. for a period comprised from 1 to 48 hours. The PPE cross-linked NaCMC (hydrogel) of the present invention (PPE-CMC) was then washed with acidic water solution (1M hydrochloric acid and PBS) from 48 to 120 hours to remove unreacted materials and by-products, to neutralize alkaline catalyst and restore the pH of hydrogel to 6.5-7.4 by ion exchange and to reach the concentration of NaCMC in the PPE cross-linked NaCMC (hydrogel) of the present invention from 1 to 50 mg/mL as shown in Table below (PPE-CMC).

The PPE cross-linked NaCMC (hydrogel) of the present invention was filled into syringes and steam sterilized in autoclave following the pharmacopeia reported in the EN ISO 17665-1 (e.g. 15 min at 121° C.). The hydrogel could be optionally dehydrated by freeze-drying and stored for following use or analysis.

2.4.2. Comparative GDE Cross-Linked Sodium Carboxymethyl Cellulose (Comp. GDE-CMC)

The comparative GDE cross-linked NaCMC was prepared following the process as disclosed above in section 2.1.2.1. for the comparative GDE cross-linked hyaluronic acid but using NaCMC instead of hyaluronic acid.

2.4.3. Characterization of the Cross-Linked NaCMC

The mechanical properties of the PPE cross-linked NaCMC of the present invention (PPE-CMC Ex. 1-3) and the comparative GDE cross-linked NaCMC (Comp. GDE Ex 1) obtained above are disclosed in Table below, having a concentration of 22.0 mg/mL:

TABLE 15

| | Components of the cross-linked NaCMC | | | Cross-linking reaction conditions | | Mechanical parameters of the cross-linked NaCMC | | |
|---|---|---|---|---|---|---|---|---|
| N° of crosslinked CMC | Conc. NaCMC[(a)] | Cross-linker | Conc. crosslinker[(b)] | T[a] (° C.) | Time (h) | G' at 0.7 Hz (Pa) | $D_N$ (nm) | C.D. (%) |
| Comp GDE-CMC Ex.1 | 10.00 | 1,3-GDE | 0.4 | 30 | 7 | 401.54 ± 3.80 | 24.17 ± 0.05 | 0.2473 |
| PPE-CMC Ex. 1 | 10.00 | PPE Ex. 22 | 0.4 | 30 | 7 | 361.78 ± 7.23 | 24.77 ± 0.12 | 0.2297 |
| PPE-CMC Ex. 2 | 10.00 | PPE Ex. 23 | 0.4 | 30 | 8 | 220.57 ± 4.68 | 27.55 ± 0.11 | 0.1670 |
| PPE-CMC Ex. 3 | 10.00 | PPE Ex. 16 | 0.4 | 30 | 9 | 159.63 ± 5.17 | 29.22 ± 0.16 | 0.1400 |

[(a)]concentration of NaCMC in the cross-linked hydrogel expressed as percentage by weight in relation to the total weight.
[(b)]concentration of the crosslinker of the present invention in the cross-linked NaCMC expressed as percentage by weight in relation to the total weight.

2.4.4 Assay 2.4.4.1 Enzymatic Degradation Assay

Samples:

The evaluation of enzymatic degradation rate was performed with:

the comparative GDE cross-linked sodium carboxymethylcellulose (hydrogel) Comp. GDE-CMC Ex. 1, and PPE cross-linked sodium carboxymethylcellulose (hydrogel) of the present invention PPE-CMC Ex. 1, PPE-CMC Ex. 2 and PPE-CMC Ex. 3.

Method:

0.2 mL of each tested cross-linked sodium carboxymethylcellulose (hydrogel) was treated with 10 μL of 0.1 mg/mL Pectinase from Aspergillus Niger. Tested hydrogels were incubated for 16 hours at 37° C. in PBS, hexoses monomers from degraded sodium carboxymethylcellulose hydrogel was evaluated with carbazole assay.

Results:

The comparative GDE cross-linked sodium carboxymethylcellulose (Comp. GDE-CMC Ex. 1) and the PPE cross-linked sodium carboxymethylcellulose of the present invention (PPE-CMC Ex. 1) show comparable cross-linking degree. The PPE hydrogels of the present invention (PPE-CMC Ex. 2 and PPE-CMC Ex. 3) shown a decreasing of cross-linking degree, therefore should be expected a decrease in the enzymatic degradation resistance, unexpectedly and counterintuitively, the amount of free hexoses monomers after enzymatic degradation is decreased to 64.6% and 85.4% for the PPE-CMC Ex. 2 and PPE-CMC Ex. 3 respectively, indicating a statistical significance increasing of enzymatic degradation resistance.

Therefore, the protective effect of the PPE of the present invention is significative higher against enzymatic degradation than the comparative GDE. In particular, the protective effect of PPE with high molecular weight (i.e. from 3000 Da to 15000 Da) is higher than the protective effect of PPE with low molecular weight against enzymatic degradation (i.e. from 750 Da to lower than 3000 Da), even if the low molecular weight PPE give the better mechanical properties. The 22 mg/mL AS from PPE-AS Ex. 2 showed greater resistance to in vitro enzymatic degradation by hyaluronidase than the others.

The results of the enzymatic degradation assay of the comparative sodium carboxymethylcellulose cross-linked with GDE and the sodium carboxymethylcellulose cross-linked with PPE of the present invention are summarized in Table below:

TABLE 16

| N° of crosslinked-CMC | Crosslinker of the Crosslinked NaCMC | Hexoses t = 0 (control) (%) | Hexoses t = 16 h, 37° C. (%) | C.D. (%) | % of relative degradation rate (to GDE) |
|---|---|---|---|---|---|
| Comp. GDE-CMC Ex. 1 | 1,3-GDE | 11.5 ± 0.5 | 87.4 ± 1.1 | 0.2473 | 100.0 ± 4.5 |
| PPE-CMC Ex. 1 | PPE Ex. 22 | 11.8 ± 0.2 | 69.3 ± 1.4 | 0.2297 | 79.3 ± 2.2 |
| PPE-CMC Ex. 2 | PPE Ex. 23 | 10.6 ± 0.7 | 56.5 ± 1.9 | 0.1670 | 64.6 ± 4.7 |
| PPE-CMC Ex. 3 | PPE Ex. 16 | 10.6 ± 0.2 | 74.6 ± 1.0 | 0.1400 | 85.4 ± 1.8 |

Therefore, the protective effect of the PPE of the present invention is significative higher against enzymatic degradation than the comparative GDE. In particular, the protective effect of PPE with high molecular weight (i.e. from 3000 Da to 15000 Da) is higher than the protective effect of PPE with low molecular weight against enzymatic degradation (i.e. from 750 Da to lower than 3000 Da), even if the low molecular weight PPE give the better mechanical properties.

2.4.4.2 Oxidative Degradation Assay

Samples:

The evaluation of oxidative degradation rate was performed with:

the comparative GDE cross-linked sodium carboxymethylcellulose Comp. GDE-CMC Ex. 1, and PPE cross-linked sodium carboxymethylcellulose of the present invention PPE-CMC Ex. 1, PPE-CMC Ex. 2 and PPE-CMC Ex. 3.

Method:

The resistance to oxidative degradation was evaluated following the method disclosed in the previous section 2.2.4.2 Oxidative degradation assay.

Results:

The comparative GDE cross-linked sodium carboxymethylcellulose (Comp. GDE-CMC Ex. 1) and the PPE cross-linked sodium carboxymethylcellulose of the present invention (PPE-CMC Ex. 1) show comparable cross-linking degree, the PPE crosslinked sodium carboxymethylcellulose of the present invention (PPE-CMC Ex. 2 and PPE-CMC Ex. 3) shows a decreasing of cross-linking degree, therefore should be expected a decrease the oxidative degradation resistance, unexpectedly and counterintuitively, the amount of free hexoses monomers after oxidative degradation is decreased to 92.6, 83.7 and 82.5 respectively for PPE-CMC Ex. 1, PPE-CMC Ex. 2 and PPE-CMC Ex. 3, indicating a statistical significance increasing of oxidative degradation resistance.

Therefore, as it is shown in the above results and it is mentioned above for the oxidative degradation rate, the crosslinked polysaccharides of the present invention prepared by using the hyperbranched PPE of the present invention as a crosslinker have a better oxidative degradation resistance (which means a lower percentage of relative oxidative degradation rate) than crosslinked polysaccharides falling outside the scope of protection of the present invention prepared by using the above-disclosed comparative crosslinkers but having comparable physical properties.

The results of the oxidative degradation assay of the comparative sodium carboxymethylcellulose cross-linked with GDE and the sodium carboxymethylcellulose cross-linked with PPE of the present invention are summarized in Table below:

TABLE 17

| N° of crosslinked-CMC | Cross-linker of the crosslinked NaCMC | Hexoses t = 0 (control) (%) | Hexoses t = 24 h, 37° C. (%) | C.D. (%) | % of relative degradation rate (to GDE) |
|---|---|---|---|---|---|
| Comp. GDE-CMC Ex. 1 | 1,3-GDE | 11.5 ± 0.5 | 94.8 ± 1.8 | 0.2473 | 100.0 ± 4.7 |
| PPE-CMC Ex. 1 | PPE Ex. 22 | 11.8 ± 0.2 | 87.8 ± 1.7 | 0.2297 | 92.6 ± 2.5 |
| PPE-CMC Ex. 2 | PPE Ex. 23 | 10.6 ± 0.7 | 79.3 ± 0.9 | 0.1670 | 83.7 ± 5.5 |
| PPE-CMC Ex. 3 | PPE Ex. 16 | 10.6 ± 0.2 | 78.2 ± 0.8 | 0.1400 | 82.5 ± 1.6 |

3. Determination of Injection Force Through Needle from Prefilled Syringes of PPE Cross-Linked Polysaccharides of the Present Invention This test allows determining the injection force through needle. In particular the peak injection force refers to the force required by the compound or composition to overcome static friction. Regarding the crosslinked polysaccharide, this value depends on its homogeneity, the quality of the syringe and also its barrel lubrication. Usually this value is representative of the whole quality of the system (compound, syringe and needle). Thus, a lower value of the injection force renders a lower pain perception without increasing the injection speed.

Tested samples:

the comparative BDDE cross-linked hyaluronic acid (hydrogel) Comp. BDDE-HA Ex. 5, comparative PEGDE cross-linked hyaluronic acid (hydrogel) Comp. PEGDE-HA Ex. 5, comparative GDE cross-linked hyaluronic acid (hydrogel) Comp. GDE-HA Ex. 5, and PPE cross-linked hyaluronic acid (hydrogel) of the present invention PPE-HA Ex. 10, PPE-HA Ex. 11 and PPE-HA Ex. 12.

The effect of injection through needle was evaluated by performing the test on injected samples. Gauge lengths 27G and 30G, and in general chose of right needle is strongly affected by physiochemical and mechanical properties of the hydrogels. The injection force was measured on a Texture Analyzer (Stable Micro Systems, TA. XT Plus) as the force (in N) needed to inject the hydrogel through a 27G and 30G needles over a distance of 50 mm at a speed of 10 mm/min (0.2 mL/min) using 1 mL syringes.

The comparison of the peak injection force and the average injection force through 27G needle of comparative hyaluronic acid (hydrogel) cross-linked with BDDE, PEGDE and GDE using the standard method and the hyaluronic acid (hydrogel) cross-linked with the PPE of the present invention (all cross-linkers have the same equivalent epoxy content when added to polysaccharide) are disclosed in Table below:

TABLE 18

| N° of crosslinked | cross-linker | Needle gauge | C.D. (%) | Peak Injection force (N) | Average Injection force (N) |
|---|---|---|---|---|---|
| Comp. BDDE-HA Ex. 5 | BDDE | 27G | 0.0952 | 40.2 ± 3.1 | 37.1 ± 3.6 |
| Comp. PEGDE-HA Ex. 5 | PEGDE | 27G | 0.0944 | 44.4 ± 3.3 | 35.9 ± 5.5 |
| Comp. GDE-HA Ex. 5 | 1,3-GDE | 27G | 0.0949 | 36.5 ± 5.4 | 34.7 ± 4.0 |
| PPE-HA Ex. 10 | PPE Ex. 22 | 27G | 0.0929 | 34.6 ± 2.2 | 32.1 ± 2.4 |
| PPE-HA Ex. 11 | PPE Ex. 23 | 27G | 0.0845 | 24.5 ± 1.9 | 21.2 ± 2.1 |
| PPE-HA Ex. 12 | PPE Ex. 16 | 27G | 0.0811 | 25.2 ± 2.1 | 18.8 ± 1.9 |

As it is shown in the above-mentioned results, the crosslinked polysaccharides of the present invention have a lower value of the peak injection force than the comparative crosslinked polysaccharides falling outside the scope of the present invention. It is advantageous because without compromising (increasing) the injection speed, the crosslinked polysaccharides of the present invention are easier to inject reducing the pain perception and the skin trauma. Furthermore, it is also advantageous because the handiness of the crosslinked polysaccharides of the invention for the practitioner is increased.

Citation List

He, Z., et al., "Ultrasonication-assisted rapid determination of epoxide values in polymer mixtures containing epoxy resin". Analytical Methods, 2014, vol. 6(12), pp. 4257-4261.

For reasons of completeness, various aspects of the invention are set out in the following numbered clauses:

Clause 1. A compound of formula (I), (I)

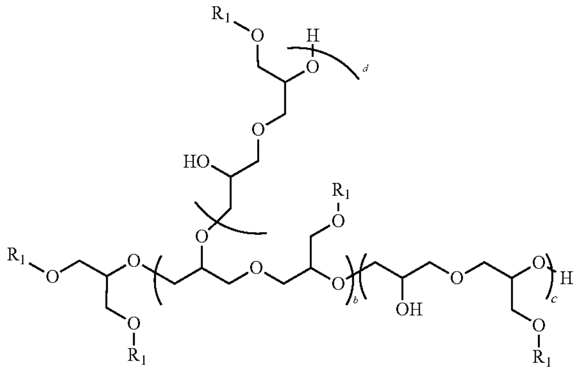

or alternatively, a compound of formula (II)

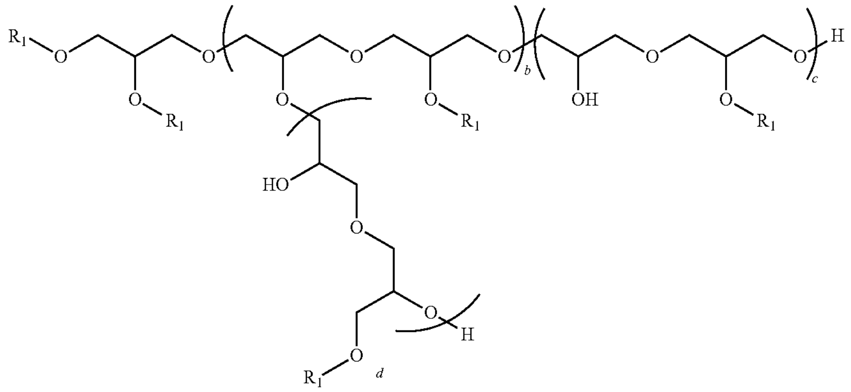

wherein each $R_1$ is independently selected from the group consisting of $R_2$ and $R_3$;

$R_2$ is

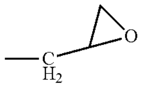

$R_3$ is

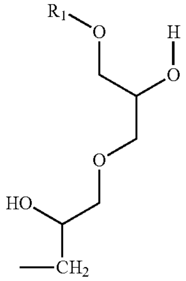

b is an integer selected from the group consisting of 1 to 70;

c is an integer selected from the group consisting of 1 to 70;

d is an integer selected from the group consisting of 1 to 70;

having a molecular weight ($M_w$) from 750 to 15.000 Da measured by the method by liquid chromatography; and an epoxy equivalent weight from 183 to 7.000 g/eq measured by ultrasonication-assisted rapid titration with HCl.

Clause 2. The compound according to clause 1, wherein:

the molecular weight ($M_w$) is from 800 to 7000 Da measured by the method by liquid chromatography; and the epoxy equivalent weight is from 195 to 700 g/eq measured by ultrasonication-assisted rapid titration with HCl.

Clause 3. The compound according to any of the clauses 1 or 2, wherein:

the molecular weight ($M_w$) is from 900 to 4500 Da measured by the method by liquid chromatography; and the epoxy equivalent weight is from 200 to 600 g/eq measured by ultrasonication-assisted rapid titration with HCl.

Clause 4. The compound according to any of the clauses 1-3, which has a polydispersity index ($M_w/M_n$) equal to or less than 1.8 measured by liquid chromatography.

Clause 5. A crosslinked polysaccharide of formula (III)

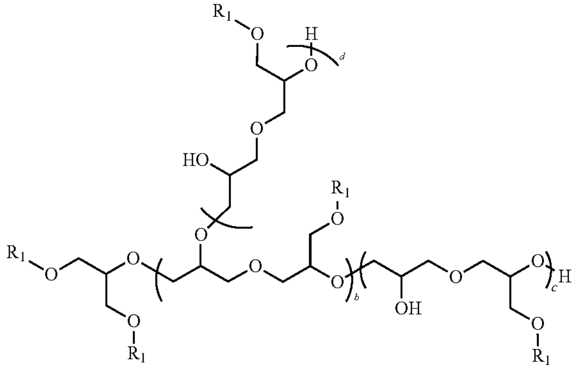

or alternatively, a crosslinked polysaccharide of formula (IV)

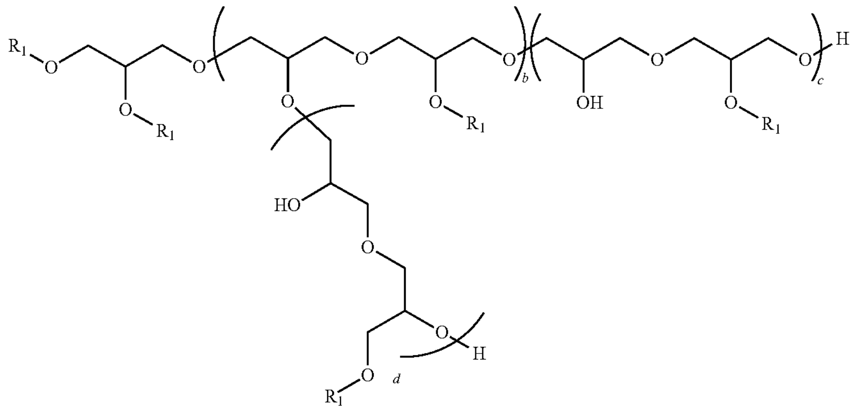

wherein each $R_1$ is independently selected from the group consisting of $R_2$, $R_3$, $R_4$ and $R_5$;

$R_2$ is

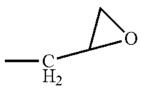

$R_3$ is

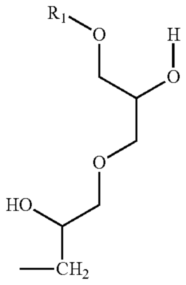

$R_4$ is

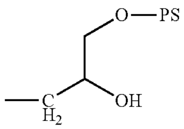

$R_5$is

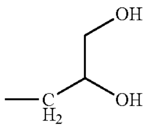

PS is a polysaccharide; and the crosslinked polysaccharide has a crosslinking percentage from 0.077 to 0.269%.

Clause 6. The crosslinked polysaccharide according to clause 5, wherein:

the relative enzymatic degradation rate is from 100% to 37.9%; and the relative oxidative degradation rate is from 100% to 76.8%.

Clause 7. The crosslinked polysaccharide according to any of the clauses 5-6, wherein the polysaccharide is selected from the group consisting of hyaluronic acid, starch and derivative thereof, glycogen, cellulose and derivative thereof, pectin, lignin, inulin, guar gum, xanthan gum, alginic acids (alginates), glucomannan, galactomannan and carrageenans; preferably hyaluronic acid.

Clause 8. The crosslinked polysaccharide according to any of the clauses 5-7, wherein the average distance ($D_N$) between two crosslinking groups is from 27 nm to 42 nm.

Clause 9. The crosslinked polysaccharide according to any of the clauses 5-8, wherein the concentration of the polysaccharide is from 1 to 50 mg/ml.

Clause 10. The crosslinked polysaccharide according to any of the clauses 5-9, which is obtainable by a process which comprises: crosslinking the polysaccharide with a compound selected from the group consisting of a compound of formula (I), a compound of formula (II) and a mixture thereof as defined in any of the clauses 1-4.

Clause 11. The crosslinked polysaccharide according to clause 10, which is obtainable by a process which comprises crosslinking the polysaccharide with a compound of formula (I), wherein the compound of formula (I) is obtained by a process comprising:

a) providing an alkaline solution containing 1,3-glycerol diglycidyl ether; and b) maintaining the solution obtained in step a) at a temperature from 10 to 80° C. for a period of time from 1 min to 30 days;

or alternatively, obtainable by a process which comprises crosslinking the polysaccharide with a compound of formula (II), wherein the compound of formula (II) is obtained by a process comprising:

c) providing an alkaline solution containing 1,2-glycerol diglycidyl ether; and d) maintaining the solution obtained in step c) at a temperature from 10 to 80° C. for a period of time from 1 min to 30 days;

or alternatively, obtainable by a process which comprises crosslinking the polysaccharide with a mixture of a compound of formula (I) and a compound of formula (II), wherein:

the compound of formula (I) is obtained by a process comprising:

a) providing an alkaline solution containing 1,3-glycerol diglycidyl ether; and b) maintaining the solution obtained in step a) at a temperature from 10 to 80° C. for a period of time from 1 min to 30 days; and the compound of formula (II) is obtained by a process comprising:

c) providing an alkaline solution containing 1,2-glycerol diglycidyl ether; and d) maintaining the solution obtained in step c) at a temperature from 10 to 80° C. for a period of time from 1 min to 30 days.

Clause 12. The crosslinked polysaccharide according to clause 11, wherein:

in step a) the alkaline solution comprises from 1 to 50 percent by weight of 1,3-glycerol diglycidyl ether; and in step c) the alkaline solution comprises from 1 to 50 percent by weight of 1,2-glycerol diglycidyl ether.

Clause 13. A process for the preparation of a compound (I) or alternatively of a compound of formula (II) as defined in any of the clauses 1-4; wherein:

when the compound is a compound of formula (I), then the process comprises:

a) providing an alkaline solution containing 1,3-glycerol diglycidyl ether; and b) maintaining the solution obtained in step a) at a temperature from 10 to 80° C. for a period of time from 1 min to 30 days;

or alternatively, when the compound is a compound of formula (II), then the process comprises:

c) providing an alkaline solution containing 1,2-glycerol diglycidyl ether; and d) maintaining the solution obtained in step c) at a temperature from 10 to 80° C. for a period of time from 1 min to 30 days.

Clause 14. A composition comprising:

one or more of the crosslinked polysaccharides as defined in any of the clauses 5-12, and one or more appropriate excipients or carriers.

Clause 15. A composition according to clause 14, which is a pharmaceutical composition comprising a therapeutically effective amount of one or more pharmaceutically acceptable crosslinked polysaccharides as defined in any of the clauses 5-12, and one or more pharmaceutically acceptable excipients or carriers for use in therapy.

Clause 16. Use of a composition according to clause 14, which is a cosmetic composition comprising a cosmetically effective amount of one or more cosmetically acceptable crosslinked polysaccharide as defined in any of the clauses 5-12, and one or more cosmetically acceptable excipients or carriers as skin care agent; particularly as dermal filler.

The invention claimed is:

1. A crosslinked polysaccharide of formula (III) or formula (IV)

(III)

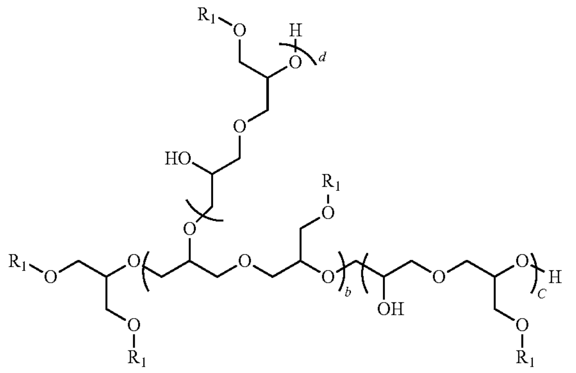

(IV)

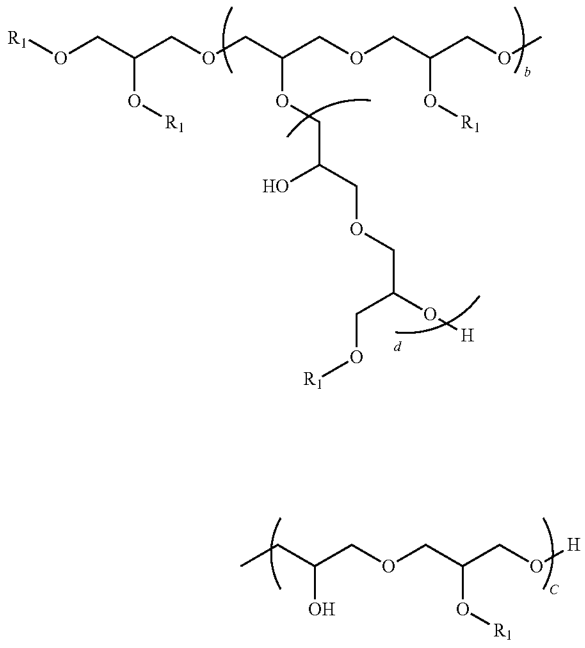

wherein the crosslinked polysaccharide is in the form of a hydrogel composition, wherein each $R_1$ is independently selected from the group consisting of $R_2$, $R_3$, $R_4$ and $R_5$, wherein at least two $R_1$ are $R_4$;

$R_2$ is

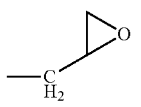

$R_3$ is

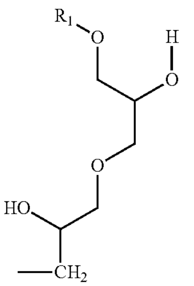

$R_4$ is

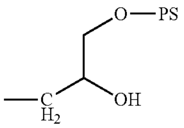

$R_5$ is

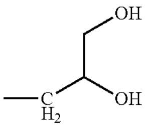

PS is a polysaccharide selected from the group consisting of hyaluronic acid, starch or a derivative thereof, glycogen, cellulose or a derivative thereof, pectin, lignin, inulin, guar gum, xanthan gum, alginic acids (alginates), heparin, chondroitin sulphate, dermatan sulphate, glucuronan, glucomannan, galactomannan and carrageenan;

b is an integer selected from the group consisting of 1 to 70;

c is an integer selected from the group consisting of 1 to 70;

d is an integer selected from the group consisting of 1 to 70; and wherein the crosslinked polysaccharide has a crosslinking percentage from 0.077 to 0.450%.

2. The crosslinked polysaccharide according to claim 1, wherein the crosslinked polysaccharide has a crosslinking percentage from 0.077 to 0.269%.

3. The crosslinked polysaccharide according to claim 1, wherein the amount of $R_2$ is lower than 2 ppm based on the total weight of the crosslinked polysaccharides of formula (III) and (IV).

4. The crosslinked polysaccharide according to claim 1, wherein:

the relative enzymatic degradation rate is from 100% to 37.9%; and the relative oxidative degradation rate is from 100% to 76.8%.

5. The crosslinked polysaccharide according to claim 1, wherein the average distance ($D_N$) between two crosslinking groups is from 27 nm to 42 nm.

6. The crosslinked polysaccharide according to claim 1, wherein the concentration of the polysaccharide in the hydrogel composition is from 1 to 50 mg/ml.

7. The crosslinked polysaccharide according to claim 1, wherein the crosslinked polysaccharide is prepared by a process comprising:

crosslinking a polysaccharide with a compound selected from the group consisting of a compound of formula (I), a compound of formula (II) and a mixture thereof;

wherein the compound of formula (I) is of formula:

(I)

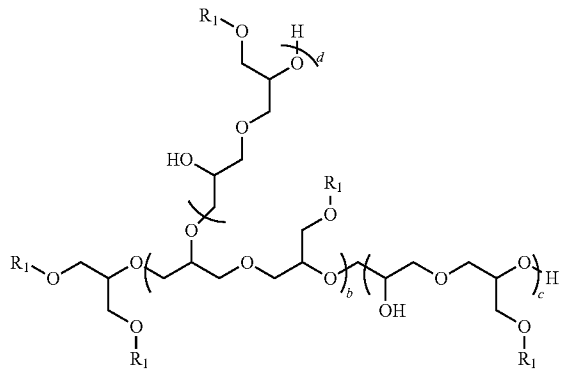

wherein the compound of formula (II) is of formula:

(II)

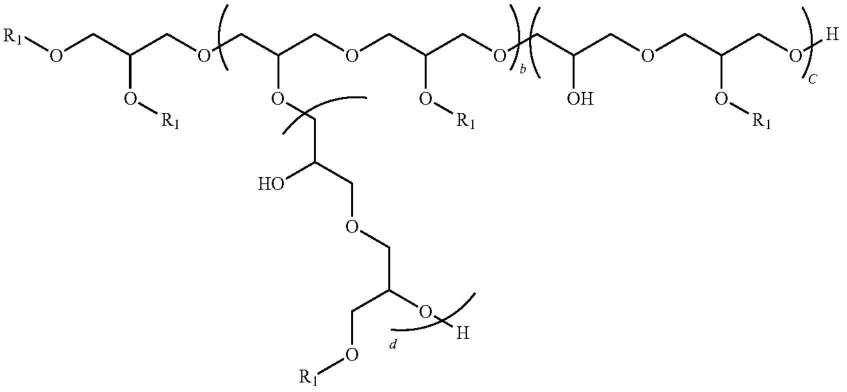

wherein each $R_1$ is independently selected from the group consisting of $R_2$ and $R_3$;

$R_2$ is

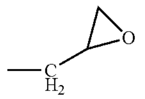

$R_3$ is

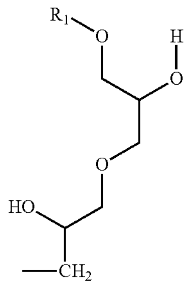

b is an integer selected from the group consisting of 1 to 70;

c is an integer selected from the group consisting of 1 to 70;

d is an integer selected from the group consisting of 1 to 70;

wherein the compound has a molecular weight ($M_w$) from 750 to 15,000 Da measured by the method of liquid chromatography; and wherein the compound has an epoxy equivalent weight from 183 to 7,000 g/eq measured by the method of ultrasonication-assisted rapid titration with HCl.

8. The crosslinked polysaccharide according to claim 7, wherein the process comprises crosslinking the polysaccharide with a compound of formula (I), wherein the compound of formula (I) is obtained by a process comprising:

a) providing an alkaline solution containing 1,3-glycerol diglycidyl ether; and b) maintaining the solution obtained in step a) at a temperature from 10 to 80° C. for a period of time from 1 min to 30 days; or wherein the process comprises crosslinking the polysaccharide with a compound of formula (II), wherein the compound of formula (II) is obtained by a process comprising:

c) providing an alkaline solution containing 1,2-glycerol diglycidyl ether; and d) maintaining the solution obtained in step c) at a temperature from 10 to 80° C. for a period of time from 1 min to 30 days;

or wherein the process comprises crosslinking the polysaccharide with a mixture of a compound of formula (I) and a compound of formula (II), wherein the compound of formula (I) is obtained by a process comprising:

a) providing an alkaline solution containing 1,3-glycerol diglycidyl ether; and b) maintaining the solution obtained in step a) at a temperature from 10 to 80° C. for a period of time from 1 min to 30 days; and wherein the compound of formula (II) is obtained by a process comprising:

c) providing an alkaline solution containing 1,2-glycerol diglycidyl ether; and d) maintaining the solution obtained in step c) at a temperature from 10 to 80° C. for a period of time from 1 min to 30 days.

9. The crosslinked polysaccharide according to claim 8, wherein:

in step a) the alkaline solution comprises from 1 to 50 percent by weight of 1,3-glycerol diglycidyl ether; and in step c) the alkaline solution comprises from 1 to 50 percent by weight of 1,2-glycerol diglycidyl ether.

10. The crosslinked polysaccharide according to claim 1, wherein the hydrogel composition is a pharmaceutical composition further comprising one or more pharmaceutically acceptable excipients or carriers, wherein the crosslinked polysaccharides is present in a therapeutically effective amount.

11. The crosslinked polysaccharide according to claim 1, wherein the hydrogel composition is a cosmetic composition further comprising one or more cosmetically acceptable excipients or carriers, wherein the crosslinked polysaccharides is present in a cosmetically effective amount.

12. The composition according to claim 11, wherein the cosmetic composition is a dermal filler.

13. The crosslinked polysaccharide according to claim 1, wherein the polysaccharide is hyaluronic acid.

* * * * *